(12) United States Patent
Behforouz et al.

(10) Patent No.: US 6,444,684 B1
(45) Date of Patent: Sep. 3, 2002

(54) LAVENDAMYCIN ANALOGS, QUINOLINE-5,8-DIONES AND METHODS OF USING THEM

(75) Inventors: Mohammad Behforouz; Nancy C. Behforouz, both of Muncie, IN (US)

(73) Assignee: Ball State University, Muncie, IN (US)

( * ) Notice: Subject to any disclaimer, the term of this patent is extended or adjusted under 35 U.S.C. 154(b) by 0 days.

(21) Appl. No.: 09/515,785

(22) Filed: Feb. 29, 2000

Related U.S. Application Data

(60) Division of application No. 08/962,427, filed on Oct. 31, 1997, now Pat. No. 6,030,983, which is a continuation-in-part of application No. 08/476,213, filed on Jun. 7, 1995, now Pat. No. 5,712,289, which is a continuation-in-part of application No. 08/345,509, filed on Nov. 28, 1994, now Pat. No. 5,646,150, which is a continuation-in-part of application No. 08/071,648, filed on Jun. 4, 1993, now Pat. No. 5,525,611.

(51) Int. Cl.[7] .................. A61K 31/47; C07D 215/20
(52) U.S. Cl. .................. 514/311; 546/171; 546/169
(58) Field of Search .................. 546/155, 156, 546/171, 169; 514/312, 313, 311

(56) References Cited

PUBLICATIONS

Liao, T.K. et al. : Synthetic studies of the Antitumor antibiotic streptonigrin. J. Heterocyc. Chem. vol. 13, pp. 1063–1065, 1976.*

* cited by examiner

*Primary Examiner*—Charanjit S. Aulakh

(74) *Attorney, Agent, or Firm*—Brinks Hofer Gilson & Lione

(57) ABSTRACT

The invention provides novel lavendamycin analogs having the following general formula:

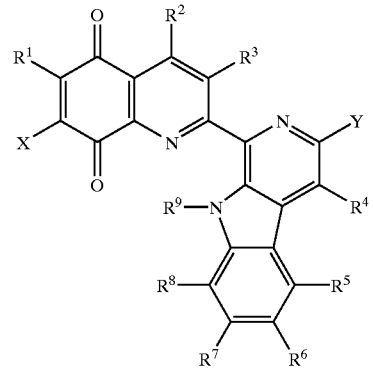

and quinoline-5,8-diones having the following formula:

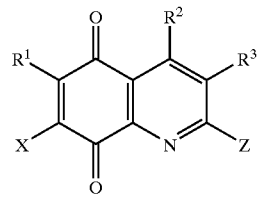

Methods of making and using and compositions containing these compounds are also disclosed.

6 Claims, 1 Drawing Sheet

LAVENDAMYCIN ANALOGS, QUINOLINE-5,8-DIONES AND METHODS OF USING THEM

This application is a division of application Ser. No. 08/962,427 filed on Oct. 31, 1997, issued on Feb. 29, 2000 as U.S. Pat. No. 6,030,983, which was a continuation-in-part of application Ser. No. 08/476,213, filed Jun. 7, 1995, issued Jan. 27, 1998 as U.S. Pat. No. 5,712,289, which was in turn a continuation in part application of application Ser. No. 08/345,509, filed Nov. 28, 1994, issued Jul. 8, 1997 as U.S. Pat. No. 5,646,150, which was a continuation-in-part of application Ser. No. 08/071,648, filed Jun. 4, 1993; issued Jun. 11, 1996 as U.S. Pat. No. 5,525,611. 5,525,611.

This invention was made in part with Government support (NIH grants 1-R15-CA54517 and 1-R15-GM37491). The Government has certain rights in the invention.

BACKGROUND OF THE INVENTION

Lavendamycin (A) was isolated from the fermentation broth of Streptomyces lavendulae by Doyle and co-workers. See Doyle et al., Tetrahedron Letters, 22, 4595 (1981) and Gould et al., Fortschr. Chem. Org. Naturst., 41, 77 (1982). Lavendamycin has broad spectrum antitumor, antibacterial and antiviral activity. See, e.g., Shibata et al., J. Antibiot., 33, 1231 (1980); Balitz et al., J. Antibiot., 35, 259 (1982); Boger et al., J. Med. Chem., 30, 1918 (1987).

Lavendamycin methyl ester (B) is also known. It can be prepared by esterification of lavendamycin. Doyle et al., Tetrahedron Letters, 22, 4595 (1981). The first total synthesis of lavendamycin methyl ester was reported by Kende and Ebetino in 1984. See Kende et al., Tetrahedron Letters, 25, 923 (1984) and Kende et al., Heterocycles, 21, 91 (1984). They accomplished the synthesis of lavendamycin methyl ester through a Bischler-Napieralski condensation of a substituted quinaldic acid with $^b$-methyltryptophan methyl ester followed by cyclization and functionalization of the A ring. Boger and his co-workers have synthesized lavendamycin methyl ester by a Friedlander condensation of a functionalized aminoaldehyde with a b-carboline followed by other transformations. Boger et al., J. Org. Chem, 50, 5790 (1985). Formal syntheses of lavendamycin methyl ester have been reported in Hibino et al., Heterocycles, 23, 261 (1985) and Rao et al., Tetrahedron, 42, 5065 (1986). For a recent review of lavendamycin syntheses, see Rao, in Recent Progress In Chemical Synthesis Of Antibiotics, 497–531 (Lukacs et al. eds., 1990).

Hibino's group has reported the synthesis of demethyllavendamycin methyl ester (C) in Hibino et al., Heterocycles, 20, 1957 (1983). Hibino's group synthesized demethyllavendamycin methyl ester by a Pictet-Spengler type cyclization of 8-benzyloxyquinoline-2-aldehyde with tryptophan methyl ester, followed by aromatization and hydrogenation to give an 8-hydroxyquinoline intermediate. This intermediate was brominated to give the 5,7-dibromo-8-hydroxyquinoline. Oxidation of the 5,7-dibromo-8-hydroxyquinoline yielded the 7-bromoquinolinequinone, and replacement of the bromine with sodium azide, followed by reduction of the azide with sodium hydrosulfite, yielded demethyllavendamycin methyl ester.

This synthetic scheme based on a Pictet-Spengler type cyclization was also used by Hibino's group for the formal synthesis of lavendamycin methyl ester mentioned above. Hibino et al. indicate that lavendamycin ethyl ester can be prepared using this same synthetic scheme. See Hibino et al., Heterocycles, 23, 261 (1985).

The Pictet-Spengler cyclization approach has further been used by Hibino's group to synthesize desaminodesmethyl-lavendamycin methyl ester (D) and eight other lavendamycin analogs. See Hibino et al., Chem. Pharm. Bull., 34, 1376 (1986). This article reports that the relative mutagenic potency of the lavendamycin analogs was drastically influenced by the nature of the substituent (e.g., methyl and/or bromine) and that lavendamycin analogs having a methyl group at the 3' position were more mutagenic.

The structures of lavendamycin and analogs B–D are presented below:

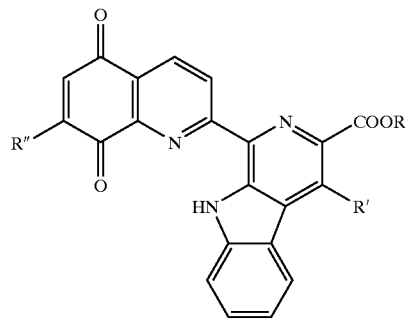

A: R=H, R'=CH$_3$, R"=NH$_2$

B: R=CH$_3$, R'=CH$_3$, R"=NH$_2$

C: R=CH$_3$, R'=H, R"=NH$_2$

D: R=CH$_3$, R'=H, R"=H

During preliminary work aimed at the total synthesis of lavendamycin, Rao et al. synthesized two additional analogs (E) and (F) of lavendamycin. See Rao et al., Indian J. Chem., 23B, 496 (1984). The structures of lavendamycin analogs E–F are presented below:

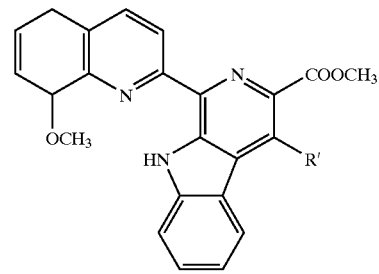

E: R'=CH$_3$

F: R'=H

Lavendamycin is similar structurally to streptonigrin (G). Streptonigrin also has a broad spectrum of antitumor, antibacterial and antiviral activity. Balitz et al., J. Antibiot., 35, 259 (1982); Rao et al., J. Am. Chem. Soc., 85, 2532 (1986); Boger et al., J. Med. Chem., 30, 1918 (1987). With notable exceptions, lavendamycin has been found to be comparable to, although less potent than, streptonigrin in its observed spectrum of activity. Id.; Balitz et al., J. Antibiot., 35, 259 (1982). The structure of streptonigrin is presented below:

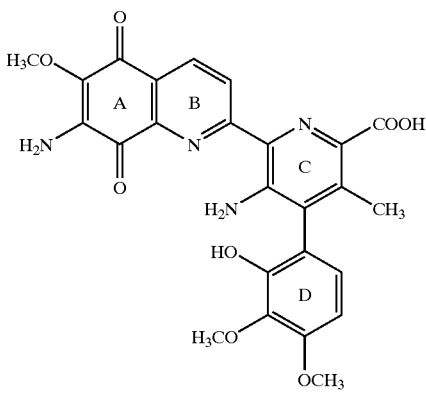

G

Streptonigrin and several streptonigrin derivatives have been synthesized. See Driscoll et al., *Cancer Chemother. Rep. (Part 2)*, 4, 1(1974) (four streptonigrin derivatives and 1500 quinones including several quinolinequinone analogs of streptonigrin having various substituents at positions 2, 6 and 7); Rao, *Cancer Chemother. Rep. (Part 2)*, 4, 11 (1974) (streptonigrin derivatives and AB and ABC ring analogs thereof); Kende et al., *Tetrahedron Lett.*, 4775 (1978) (tetracyclic aminoquinone possessing full streptonigrin carbon skeleton but with different substituents on the C and D rings); Basha et al., *J. Am. Chem. Soc.*, 102, 3962 (1980) (streptonigrin); Kende et al., *J. Am. Chem. Soc.*, 103, 1271 (1981) (streptonigrin); Weinreb et al., *J. Am. Chem. Soc.*, 104, 536–44 (1982) (streptonigrin); Panek et al., *Diss. Abs. Int'l*, 46, 1176B (1985) (streptonigrin); Miyasaka et al., *J. Chem. Soc. Perkin Trans.*, 1, 479 (1986) (streptonigrin 2'-amide derivatives; also mentions a 7-position amide obtained by high-yield microbial synthesis of *Streptomyces griseus*); Tolstikov et al., *J. Antibiot.*, 45, 1020 (1992) (2'-amide, aminodicarboxylic acid and amino sugar derivatives of streptonigrin); Tolstikov et al., *J. Antibiot.*, 45, 1002 (1992) (2'-decarboxy-2'-amino streptonigrin); Preobrazhenskaya et al., *J. Antibiot.*, 45, 227 (1992) (streptonigrone from streptonigrin, streptonigrin and streptonigrone 8'-alkyl ethers, and other streptonigrin and streptonigrone derivatives); U.S. Pat. No. 3,372,090 (ester, 2'-amide, 2'-hydrazide, ether, dihydro, desamino and acetyl (O-acetyl, N-acetyl, tetraacetyl) derivatives of streptonigrin); U.S. Pat. No. 3,804,947 (isopropylidene azastreptonigrin, streptonigrin monoxime and esters and other derivatives thereof); and JP 61-280490 (streptonigrin 2'-amides).

The biological activities of several 2'-position streptonigrin derivatives have been studied. The derivatives include 2'-esters, 2'-amides, 2'-hydrazides, and 2-'amino acid derivatives. The effects of the substituents on the biological activity of streptonigrin varied depending on the substituent and the type of activity being studied. See Rivers et al., *Cancer Chemotherapy Rep.*, 46, 17 (1965); Harris et al., *Cancer*, 18, 49 (1965); Kremer et al., *Biochem. Pharmacol.*, 15, 1111 (1966); Kaung et al., *Cancer*, 23, 1280 (1969); Inouye et al., *J. Antibiot.*, 38, 1429 (1985); Okada et al., *J. Antibiot.*, 39, 306 (1986); Inouye et al., *J. Antibiot.*, 39, 550 (1986); Okada et al., *J. Antibiot.*, 40, 230 (1987); Take et al., *J. Antibiot.*, 42, 968 (1989); Tolstikov et al., *J. Antibiot.*, 45, 1020 (1992).

The biological properties of streptonigrin, streptonigrin methyl ester and isopropylidene azastreptonigrin have been compared. See Kremer et al., *Cancer Chemother. Rep.*, 51, 19 (1967); Mizuno, *Biochem. Pharmacol.*, 16, 933 (1967); Chaube et al., *Cancer Chemother. Rep. (Part 1)*, 53, 23 (1969) and Chirigos et al., *Cancer Chemother. Rep. (Part 1)*, 57, 305 (1973). Again, the effects of the substituents varied depending on the activity being investigated.

The antibacterial activity of streptonigrin, streptonigrin methyl ester and streptonigrin 8'-alkyl ethers has been studied. See Preobrazhenskaya et al., *J. Antibiot.*, 45, 227 (1992). The 8'-alkyl ethers exhibited slightly greater antibacterial activity than streptonigrin methyl ester, but less than streptonigrin.

A naturally-occurring analog of streptonigrin, 10'-desmethoxystreptonigrin, has been discovered. U.S. Pat. No. 5,158,960; Liu et al., *J. Antibiot.*, 45, 454–57 (1992). In addition to 10'-desmethoxystreptonigrin, U.S. Pat. No. 5,158,960 discloses salts, esters and amides of 10'-desmethoxystreptonigrin. Exemplary esters and amides are those prepared by esterifying the 2'-carboxyl or by forming an amide group at the 2'-position. 10'-Desmethoxystreptonigrin was found to have anticancer and antimicrobial, particularly broad spectrum antibacterial, activity. U.S. Pat. No. 5,158,960; Liu et al., *J. Antibiot.*, 45, 454–57 (1992). It was also found to be three times more active than streptonigrin in an assay for the inhibition of the farnesylation of ras oncogene p21 protein. Id. U.S. Pat. No. 5,158,960 teaches that, since 10'-desmethoxystreptonigrin inhibits the farnesylation of ras oncogene p21 protein, it may be expected to block the neoplastic effect of ras oncogenes in tumor cells.

EP application 185 979 discloses another naturally-occurring streptonigrin analog which has a hydroxyl group in place of the methoxy group at the 6-position of streptonigrin. This compound is reported to exhibit only slightly less antitumor activity than streptonigrin, but to exhibit much lower cytotoxicity. This EP application also discloses derivatives synthesized by making use of the 6-position hydroxyl.

A third naturally-occurring analog of streptonigrin is streptonigrone. Herit et al., *J. Antibiot.*, 38, 516 (1985). Streptonigrone has also been synthesized from streptonigrin, and streptonigrone 8'-alkyl ethers and other streptonigrone derivatives have been prepared. Preobrazhenskaya et al., *J. Antibiot.*, 45, 227 (1992). Also, 2'-decarboxy-2'-aminostreptonigrin, considered to be an analog of streptonigrone, has been synthesized. Tolstikov et al., *J. Antibiot.*, 45, 1002 (1992). Streptonigrone and its derivatives have generally been found to be inactive or much less active than streptonigrin. See Herlt et al., *J. Antibiot.*, 38, 516 (1985); Preobrazhenskaya et al., *J. Antibiot.*, 45, 227 (1992); Tolstikov et al., *J. Antibiot.*, 45, 1002 (1992).

Finally, a number of streptonigrin and lavendamycin partial structures have been synthesized and their biological activities studied in an attempt to determine the minimum potent pharmacophore of streptonigrin and lavendamycin. See Driscoll et al., *Cancer Chemother. Rep. (Part 2)*, 4, 1 (1974) (1500 quinones including several quinolinequinone analogs of streptonigrin having various substituents at positions 2, 6 and 7; also four streptonigrin derivatives); Rao, *Cancer Chemother. Rep. (Part 2)*, 4, 11 (1974) (streptonigrin derivatives and AB and ABC ring analogs thereof); Rao, *J. Heterocyclic Chem.*, 12, 725 (1975) (2-phenyl- and 2,2-pyridyl-quinoline-5,8-diones); Rao, *J. Heterocyclic Chem.*, 14, 653 (1977) (ABC ring portion of streptonigrin and derivatives thereof); Lown et al., *Can. J. Chem.*, 54, 2563 (1976) (2-(o-nitrophenyl)- and 2-(o-aminophenyl)-5,8-quinolinediones); Lown et al., *Can. J. Biochem.*, 54, 446 (1976) (substituted 5,8-quinolinequinones related to streptonigrin); Liao et al., *J. Heterocyclic Chem.*, 13, 1283 (1976) (CD ring portion of streptonigrin); Rao et al., *J.*

Heterocyclic Chem., 16, 1241 (1979) (ABC ring portion of streptonigrin and analogs); Shaikh et al., Diss. Abs. Inter., 44, 1464B (1983) (2,3-disubstituted-1,4-naphthalenediones, 6,7-disubstituted 5,8-quinoline, isoquinoline, quinoxoline, quinazoline, phthalazinediones, and 2-(o-nitrophenyl)-6,7-disubstituted-5,8-quinolinediones related to streptonigrin); Boger et al., J. Org. Chem., 50, 5782 (1985) (AB and CDE ring portions of lavendamycin); Panek et al., Diss. Abs. Inter., 46, 1176B (1985) (streptonigrin and lavendamycin carbon framework); Renault et al., J. Am. Chem. Soc., 104, 1715 (1985) (5,8-quinazolinediones); Shaikh et al., J. Med. Chem., 29, 1329 (1986) (a series of aza and diaza bicyclic quinones related to the AB ring system of streptonigrin); Boger et al., Heterocycles, 24, 1067 (1986) (streptonigrin and lavendamycin AB ring systems); Inouye et al., J. Antibiot., 40, 105 (1987) (6-methoxy-5,8-dihydroquinoline-5,8-dione and 6-methoxy-7-methyl-5,8-dihydroquinoline-5,8-dione); Boger et al., J. Med. Chem., 30, 1918 (1987) (various streptonigrin and lavendamycin partial structures are discussed, including the AB, ABC, CD and CDE rings and derivatives thereof); Take et al., J. Antibiot., 40, 679 (1987) (quinoline quinones, 7-isoquinoline quinones, indole quinone); Yasuda et al., J. Antibiot., 24, 1253 (1987) (7-amino-2-(2'-pyridyl) quinoline-5,8-quinone-6'-carboxylic acid); Beach, Diss. Abs. Inter., 49, 3204-B (streptonigrin isoquinoline analogs); Kitahara et al., Chem. Pharm. Bull., 38, 2841 (1990) (8-amino-5,6-quinolinediones); Rao et al., J. Med. Chem., 34, 1871 (1991) (streptonigrin isoquinoline analogs).

Of particular note is Rao, Cancer Chemother. Rep. (Part 2), 4, 11 (1974). This article reports the results of a study of the activity of several streptonigrin derivatives and AB ring analogs which led the author to propose a structure (H) for the minimum potent pharmacophore of streptonigrin.

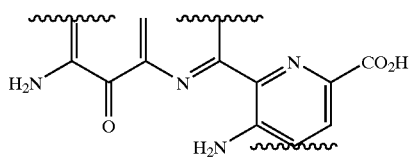

H

A tricyclic analog of H (corresponding to the ABC rings of streptonigrin) was synthesized and found to be active. Results of interest reported in this article are that replacement of the amine function at position 7 of streptonigrin by OH or $OCH_3$ led to loss of activity, and streptonigrin derivatives produced by reductive acetylation or methylation of the amine group at position 7 were inactive. Esterification of the carboxyl of streptonigrin with a series of alcohols gave esters which reportedly showed significant activity.

The fully elaborated streptonigrin CD and lavendamycin CDE ring systems, as well as a number of related synthetic structures, have reportedly proved inactive in antimicrobial and cytotoxic assays. Boger et al., J. Med. Chem., 30, 1918 (1987). However, none of the AB and ABC ring analogs of streptonigrin and lavendamycin have been reported to possess cytotoxic, antimicrobial or antitumor activity comparable to streptonigrin. See id.; Driscoll et al., Cancer Chemother. Rep. Part 2, 4, 1 (1974). This suggests a role for the CD rings in the activity of streptonigrin. See Kende et al., Tetrahedron Lett., 48, 4775 (1978).

The following references also describe the synthesis of streptonigrin and lavendamycin partial structures, but do not discuss the activity of the resulting compounds. Liao et al., Angew. Chem. Intern. Edit., 6, 82 (1967) (AB ring portion of streptonigrin); Rao et al., J. Heterocyclic Chem., 12, 731 (1975) (streptonigrin C ring precursors); Liao et al., J. Heterocyclic Chem., 13, 1063 (1976) (the AB ring portion of streptonigrin and the 2-methyl homolog); Hibino et al., J. Org. Chem., 42, 232 (1977) (the AB ring portion of streptonigrin); Wittek et al., J. Org. Chem., 44, 870 (1979) (CD ring portion of streptonigrin); Boger et al., Tetrahedron Lett., 25, 3175 (1984) (the CDE ring portion of lavendamycin); Erickson, Diss. Abs. Inter., 49, 747-B (1988) (4-aminoanthranilic acid, 7-aminoquinaldinic acid, 7-amino-5-hydroxyquinaldinic acid); Molina et al., Tetrahedron Lett., 33, 2891 (1992) (1-substituted-$^b$-carbolines). See also, Kaiya et al., Heterocycles, 27, 645–49 (1988) (6- and 7-acetylaminoquinoline-5,8-diones); Yanni, Collect. Czech. Chem. Commun., 56, 1919–25 (1991) (6-chloro-7-acylamino-5,8-diones); Klimovich et al., Khim. Geterotsikl. Soedin., 1539–41 (1975) (N-acetyl and N-propyl derivatives of 7-amino-6-chloro-5,8-quinolinedione); and U.S. Pat. No. 3,933,828.

Reverse transcriptase (RT) of retroviruses are RNA dependent DNA polymerases and play a vital role in the integration of the viral genome into host cell DNA and allow for their subsequent replication and pathogenesis. Temin, H., The RNA tumor viruses-background and foreground, Proc. Natl. Acad. Sci. USA, 1972, 69, 1016. Thus, RT is a potential therapeutic target. Nucleoside analog inhibitors of RT, such as 3'-azido-3'-deoxythymidine (AZT) and dideoxyinosine (ddI), are clinically effective drugs for treating human immunodeficiency virus (HIV) infection. Mitsuya, H.; Broder, S., Toward the rational design of antiretroviral therapy for HIV infection in "The Human Retroviruses", Gallo, R.; Jay, G., Eds.; Academic Press, Inc.: San Diego, 1991, pp. 335–338. Their effectiveness is however, limited by toxicities, which may reflect inhibition of cellular polymerases and/or alteration of nucleoside pools and the emergence of AZT-resistant viral isolates from AIDS patents. Mitsuya, H.; Yarchoan, R.; Broder, S., Molecular targets for AIDS therapy, Science, 1990, 249, 1553. Yarchoan, R.; Broder, S. Anti-retroviral therapy of AIDS and related disorders: general principles and specific development of dideoxynucleosides, Pharmocol. Ther., 1989, 40 329. Larder, B.; Darby, G.; Richman, D., HIV with reduced sensitivity to Zidovudine (AZT) isolated during prolonged therapy, Science, 1989, 243, 1731. There is a definite and urgent need to develop selective RT inhibitors that can be used either alone or in combination with nucleoside analogs.

Recent efforts in the search for new drugs that can be used to treat (HIV) disease or AIDS have resulted in the identification of several families of nonnucleoside inhibitors active against this virus by selective binding to the viral reverse transcriptase. Baba, M.; Declereq, E.; Tanaka, H.; Ubasawa, M.; Takashima, H.; Sekiya, K.; Nitta, I.; Umezu, K.; Nakashima, H.; Mori, S.; Shigeta, S.; Walker, R.; Miyasaka, T., Potent and selective inhibition of human immunodeficiency virus type 1 (HIV-1) by 5-ethyl-6-phenylthiouracil derivatives through their interaction with the HIV-1 reverse transcriptase. Proc. Natl. Acad. Sci. USA, 1991, 88, 2356. Goldman, M.; Nunberg, J.; O'Brien, J.; Quintero, J.; Schleif, W.; Freund, K.; Gaul, S.; Saari, S.; Wai, j.; Hoffman, J.; Anderson, P.; Hupe, D.; Emini, E.; Stern, A., Pyridinone derivatives: specific human immunodeficiency virus type I reverse transcriptase inhibitors with antiviral activity. Proc. Natl. Acad. Sci. USA, 1991, 88, 6863. Pauwels, R.; Andries, K.; Desmyter, J.; Schols, D.; Kukla, M.; Breslin, H.; Raeymaekers, A.; VanGelder, J.; Woestenborghs, R.; Heykants, J.; Schellekens, K.; Janssen, M.; DeClereq, E.; Janssen, P., Potent and selective inhibition of HIV-1 replication in vitro by a novel series of TIBO derivatives, *Nature* (London), 1990, 343,470. Okada, H.; Inouye, Y.; Nakamura, S., Kinetic analysis of inhibition of reverse transcriptase by streptonigrin, *J. Antibiotics*, 1987, 40, 230. One of these families of nonnucleoside inhibitors includes streptonigrin and lavendamycin. Rao, K.; Cullen, W., Streptonigrin, an antitumor substance I. Isolation and characterization in "Antibiotics Annual 1959–1960", Welch, H.; Marti-Ibanez, F., Eds.; Medical Encyclopedia, Inc.: New York, 1960, pp. 950–953. Doyle T.; Balitz, D.; Grulich, R.; Nettleton, D.; Gould, S.; Tann, C.; Moens, A., Structure determination of lavendamycin—A new antitumor antibiotic from *Streptomyces lavendulae, Tetrahedron Lett.*, 1981, 22, 4595. Streptonigrin, an aminoquinoline quinone produced by several Streptomyces species, has a wide spectrum of antimicrobial, antitumor and anti-viral activities. Inouye, Y.; Okada, H.; Uno, J.; Arai T.; Nakamura, S., Effects of streptonigrin derivatives and sakymicin A on the respiration of isolated rat liver mitochondria, *J. of Antibiotics*, 1986, 39, 550. This potent antibiotic is a strong inhibitor of the reverse transcriptase of both avian myeloblastosis virus (AMV) and human immunodeficiency virus reverse transcriptases. Take, Y.; Inouye, S.; Nakamura, S.; Allaudeen, H.; Kubo, A., Comparative studies of the inhibitory properties of antibiotics on human immunodeficiency virus and avian myeloblastosis virus reverse transcriptases and cellular DNA polymerases, *J. Antibiotics*, 1989, 42, 107. Unfortunately, the clinical use of streptonigrin for treating human malignancies has been discontinued because of toxicity, primarily bone marrow depression. Tolstikov, V.; Koziova, N.; Oreskina, T.; Osipova, T.; Preobrazhenskaya, M.; Sztaricshai, F.; Balzarini, J.; DeClereq, E., Amides of antibiotic streptonigrin and amino dicarboxylic acids or amino sugars. Synthesis and biologic evaluation, *J. Antibiotics*, 1992, 45, 1020. Hackethal, C.; Golbey, R.; Tan, C.; Karofsky, D.; Burchenal, J.; Clinical observation on the effects of streptonigrin in patients with neoplastic disease, *Antibiot. Chemother.*, 1961 11, 178. More recently, another the biosynthetically related Streptomyces metabolite, lavendamycin described above has been shown in limited studies to be comparable in several of its biological activities to streptonigrin. Balitz, D; Bush, J.; Bradner, W.; Doyle, T.; O'Herron, T.; Nettleton, F., Lavendamycin isolation and antimicrobial and antitumor testing, *J. Antibiotic*, 1982, 35, 259. Unfortunately, lavendamycin itself also appears to be toxic and will probably not be clinically useful either. Boger, D.; Yasuda, M.; Mitscher, L.; Drake, S.; Kitos, P.; Thompson, S., Streptonigrin and lavendamycin partial structures. Probes for the minimum, potent pharmacophore of stretonigrin, lavendamycin and synthetic quinoline-5,8-diones, *J. Med. Chem.*, 1987, 30, 1918.

SUMMARY OF THE INVENTION

The invention provides a lavendamycin analog having the following formula (I):

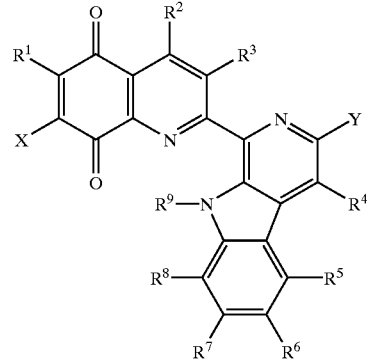

Formula I wherein,

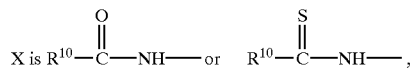

Y is H, $OR^{11}$, $SR^{11}$, $N(R^{11})_2$, $NR^{11}N(R^{11})_2$, a halogen atom, $NO_2$, CN,

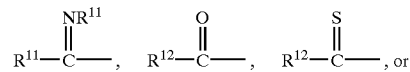

an alkyl, aryl, cycloalkyl, alkynyl, alkenyl or heterocyclic residue, each of which may be substituted or unsubstituted, $R^1$, $R^2$, $R^3$, $R^4$, $R^5$, $R^6$, $R^7$, and $R^8$, which may be the same or different, each is independently H, a halogen atom, $NO_2$, CN, $OR^{13}$, $SR^{13}$, $N(R^{13})_2$,

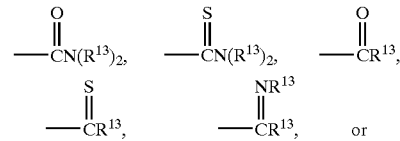

an alkyl, aryl, cycloalkyl, alkenyl, alkynyl, heteroalkyl, heterocyclic, heteroalkenyl or heteroalkynyl residue, each of which may be substituted or unsubstituted, $R^9$ is H, 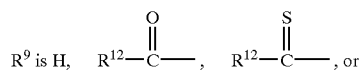

an alkyl, cycloalkyl, aryl, alkenyl, alkynyl or heterocyclic residue, each of which may be substituted or unsubstituted, $R^{10}$, $R^{11}$ and $R^{13}$, which may be the same or different, each is independently H or an alkyl, cycloalkyl, alkenyl, alkynyl, aryl or heterocyclic residue, each of which may be substituted or unsubstituted, $R^{12}$ is H, $N(R^{11})_2$, $OR^{11}$, $SR^{11}$, $NR^{11}N(R^{11})_2$, $OR^{14}N(R^{11})_2$, or an alkyl, cycloalkyl, aryl, alkenyl, alkynyl or heterocyclic residue, each of which may be substituted or unsubstituted, and $R^{14}$ is an alkylene residue, and salts of these lavendamycin analogs.

In one aspect of the invention, $R^1$ is halogen atom, preferably Cl.

In another aspect of the invention, the compound has the following formula:

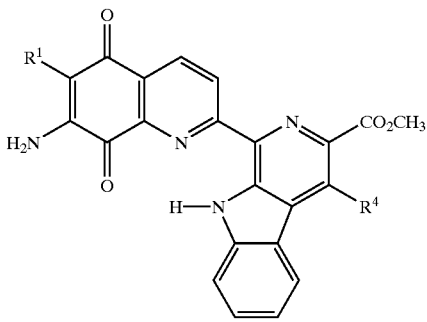

wherein

R1 is a halogen atom, and $R^4$ is H, a halogen atom, $NO_2$, CN, an alkyl, aryl, cycloalkyl, alkenyl, alkynyl, heteroalkyl, heterocyclic, heteroalkenyl or heteroalkynyl residue, each of which may be substituted or unsubstituted. Preferably, $R^1$ is Cl and $R^4$ is $CH_3$.

The invention also provides a method of preparing these lavendamycin analogs which comprises reacting an aldehyde having the following formula (K):

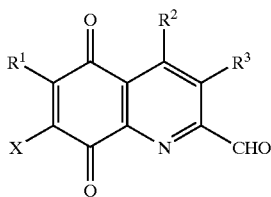

Formula K with a tryptophan analog of the formula (L):

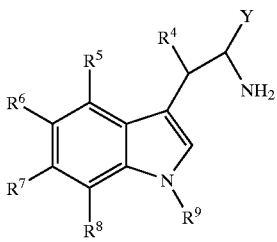

Formula L wherein X, Y and $R^1$ through $R^9$ are as defined above.

The lavendamycin analogs of the invention have antitumor and antimicrobial (antibacterial, antiviral and antiparasitic) activity. In particular, certain of the lavendamycin analogs of the invention have unexpected selective activity against $ras^K$ tumor cells.

The invention, therefore, provides methods of treating animals having a tumor or suffering from a microbial infection which comprises administering to the animals an effective amount of a lavendamycin analog of the invention or a pharmaceutically-acceptable salt thereof. The invention also provides the use of the above-described lavendamycin compounds in treating cancer. The invention also provides pharmaceutical compositions comprising a lavendamycin analog, or a pharmaceutically-acceptable salt thereof, in combination with a pharmaceutically-acceptable carrier.

The lavendamycin analogs of the invention also have anti-HIV Reverse Transcriptase (HIV-RT) activity by themselves and preferably in combination with 3'-azido-3'-deoxythymidine (AZT). Accordingly, the invention provides the use of the lavendamycin analogs in treating HIV infection and a method and composition for treating HIV infection with the lavendamycin analogs and with combinations of the lavendamycin analogs in combination with AZT.

The invention also provides a method of inhibiting the growth of microbes comprising contacting the microbe with a lavendamycin analog of the invention, or a salt thereof. For instance, the lavendamycin analogs of the invention may be added to liquids to inhibit microbial growth in them. The lavendamycin analogs may also be formulated into disinfectant preparations useful for inhibiting microbial growth on surfaces.

The invention further provides quinoline-5,8-diones having the following formula (V):

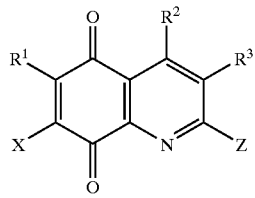

Formula V wherein, X, $R^1$, $R^2$ and $R^3$ are as defined above and Z is $CH_3$ or CHO.

In one aspect of the invention $R^1$ is a halogen atom, preferably Cl.

In another aspect of the invention, the compound has the following formula:

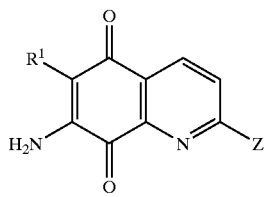

wherein $R^1$ is a halogen atom, preferably Cl, and Z is either CHO or $CH_3$.

The invention also provides a method of preparing these quinolinediones which comprises reacting a 1-silyloxy-azadiene having the following formula (N):

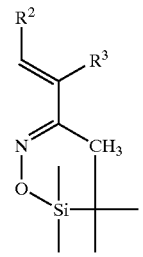

Formula N with a bromoquinone of the formula (O):

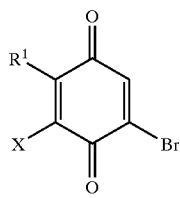

Formula O wherein X, $R^1$, $R^2$, and $R^3$ are as defined above.

The quinolinediones of the invention have antitumor activity. They are also useful for the synthesis of the lavendamycin analogs of the invention.

The invention, therefore, provides methods of treating animals having a tumor which comprises administering to the animals an effective amount of a quinolinedione of the invention or a pharmaceutically-acceptable salt thereof. The invention also provides pharmaceutical compositions comprising a quinoline dione, or a pharmaceutically-acceptable salt thereof, in combination with a pharmaceutically-acceptable carrier.

The invention also provides methods of treating cancer using lavendamycin methyl ester and its analogs, preferably 6-chlorolavendamycin methyl ester.

Finally, the invention provides methods of treating an animal suffering from HIV infection with the lavendamycin analogs and quinoline-5,8-diones described above.

DETAILED DESCRIPTION OF THE PRESENTLY PREFERRED EMBODIMENTS

Figure 1A:
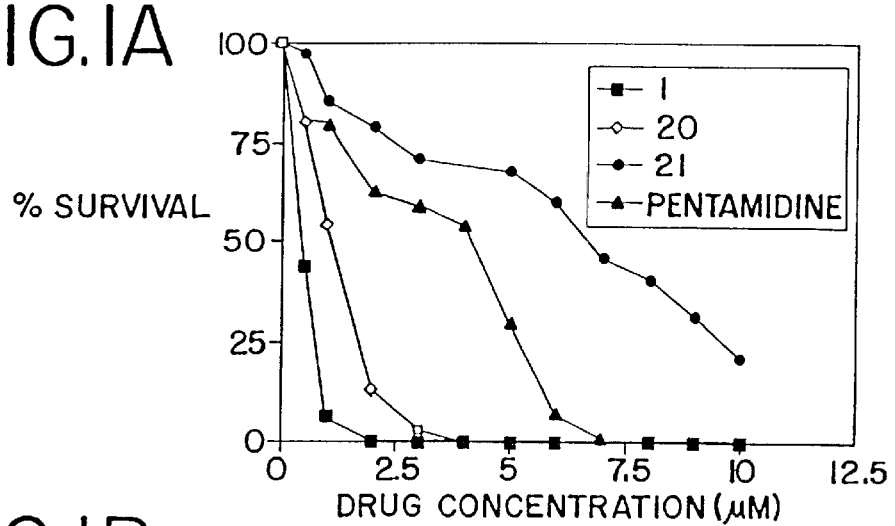
FIGS. 1A–1B: Graphs of percent survival versus drug concentration.

The lavendamycin analogs of the invention have general formula I given above. The quinolinediones of the invention have general formula V given above. In the definition of substituents X, Y and $R^1$ through $R^9$ of formulas I and V, the following terms have the following meanings.

"Alkyl" refers to straight or branched chain alkyl residue containing from 1 to 20 carbon atoms. Alkyl residues include methyl, ethyl, n-propyl, isopropyl, n-butyl, isobutyl, sec-butyl, tert-butyl, n-pentyl, 2-methylbutyl, 2,2-dimethylpropyl, isoamyl, n-hexyl, 2-methylpentyl, 2,2-dimethylbutyl, n-heptyl, 2-methylhexyl, n-octyl, etc.

"Aryl" refers to a residue comprising at least one aromatic ring of 5 or 6 carbon atoms. Aryl residues include phenyl, tolyl, biphenyl, naphthyl, etc.

"Cycloalkyl" refers to an aliphatic ring having from 3 to 8 carbon atoms. Cycloalkyl residues include cyclopropyl, cyclopentyl, cyclohexyl, etc.

"Alkenyl" refers to a straight or branched chain alkyl residue which contains from 1 to 20 carbon atoms and at least one carbon-carbon double bond. Alkenyl residues include vinyl, allyl, 1,1-dimethyl allyl, etc.

"Alkynyl" refers to a straight or branched chain alkyl residue which contains from 1 to 20 carbon atoms and at least one carbon-carbon triple bond. Alkynyl residues include ethynyl, propenyl, etc.

"Alkylene" refers to a straight or branched chain alkylene residue containing from 1 to 20 carbon atoms. Alkylene radicals include methylene, ethylene, propylene, etc.

"Heteroalkyl" refers to an alkyl containing one or more heteroatoms selected from oxygen, sulfur and nitrogen.

"Heterocyclic" refers to a cycloalkyl or aryl containing one or more heteroatoms selected from oxygen, sulfur and nitrogen. Heterocyclic residues include thienyl, furyl, pyrrolyl, imidazolyl, pyrazolyl, pyridyl, pyrazinyl, pyrimidinyl, pyridazinyl, oxazolyl, isothiazolyl, isoxazolyl, thiazolyl, oxadiazolyl, thiadiazolyl, etc.

"Heteroalkenyl" refers to an alkenyl containing one or more heteroatoms selected from oxygen, sulfur and nitrogen.

"Heteroalkynyl" refers to an alkynyl containing one or more heteroatoms selected from oxygen, sulfur and nitrogen.

The alkyl, aryl, cycloalkyl, alkenyl, alkynyl, heteroalkyl, heterocyclic, heteroalkenyl and heteroalkynyl residues may be unsubstituted or substituted with one or more substituents. Suitable substituents include $R^x$, $NH_2$, $R^xNH$, $(R^x)_2N$, CN, $N_3$, $NO_2$, OH, halogen (Cl, Br, F, I), SH, $R^xS$, $R^xSO_2$, $R^xSO$, $R^xO$, COOH, $COOR^x$, $COR^x$, CHO, and $CON(R^x)_2$, wherein $R^x$ is an alkyl, cycloalkyl, aryl, alkenyl, alkynyl or heterocyclic residue. Preferred substituents are halogen atoms.

Preferred lavendamycin analogs of the invention are those having the formula (J):

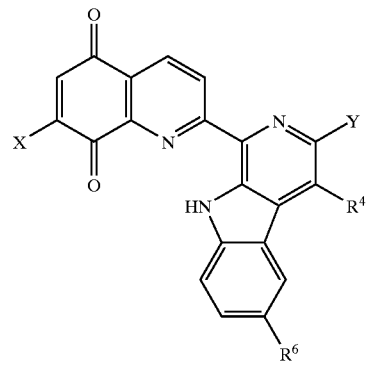

Formula J wherein X, Y, $R^4$ and $R^6$ are defined above.

More preferred are lavendamycin analogs of formula J wherein:

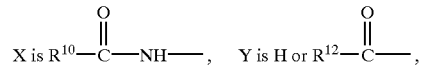

$R^4$ is H or an alkyl, and $R^6$ is H, a halogen atom or $OR^{13}$, wherein $R^{10}$, $R^{12}$ and $R^{13}$ are defined above. $R^{10}$ is preferably an alkyl or substituted alkyl. Y is preferably

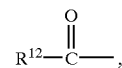

and when Y is so defined, $R^{12}$ is preferably $N(R^{11})_2$, $OR^{11}$ or $OR^{14}N(R^{11})_2$. When $R^{12}$ is so defined, $R^{11}$ is preferably H or an alkyl or cycloalkyl. When $R^{11}$ is an alkyl, it preferably contains from 2 to 20 carbon atoms, most preferably from 4 to 20 carbon atoms.

Preferred quinolinediones are those of formula V wherein

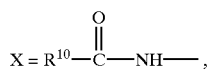

$R^{10}$ is an alkyl or substituted alkyl,
$R^1$=H,
$R^2$=H, and
$R^3$=H.

Certain lavendamycin analogs and quinoline-diones of the present invention may contain a basic functional group, such as amino or alkylamino, and are, thus, capable of forming pharmaceutically-acceptable salts with pharmaceutically-acceptable acids. The term "pharmaceutically-acceptable salts" in these instances refers to the relatively non-toxic, inorganic and organic acid addition salts of compounds of the present invention. These salts can be prepared by reacting a purified compound of the invention in its free base form with a suitable organic or inorganic acid and isolating the salt thus formed. Representative salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like. Other salts of the lavendamycin analogs and quinolinediones containing a basic functional group may be used for non-therapeutic uses.

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can be prepared by reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Other salts of the lavendamycin analogs and quinolinediones containing an acidic functional group may be used for non-therapeutic uses.

The lavendamycin analogs I of the invention may be synthesized by an efficient procedure, the final step of which is a Pictet-Spengler condensation of an aldehyde of the following formula K:

Formula K

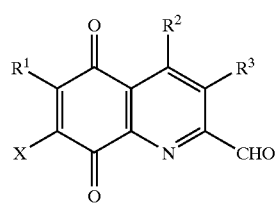

with a tryptophan analog of the formula (L):

Formula L

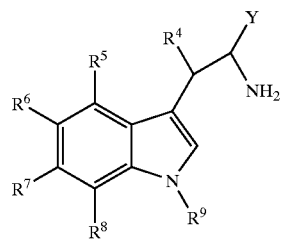

wherein X, Y and $R^1$ through $R^9$ are as defined above. See Equation 1 below:

Equation 1

K + L $\xrightarrow{\text{solvent}}$ I
$\phantom{K + L \xrightarrow{}}$ heat

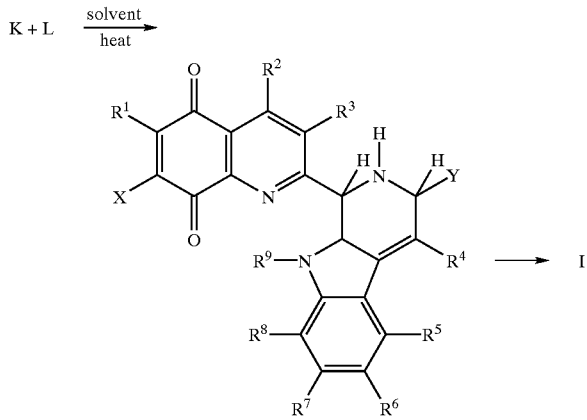

Typical reactions involve the combination of equimolar amounts of K and L in a solvent. Suitable solvents include aromatic hydrocarbons such as xylene, toluene, mesitylene, and anisole. The reactants are heated until the reaction is complete. Generally, the temperature will be about 60° C. or higher, and the reaction will take about 1 hour or more to reach completion. The lavendamycin analog is obtained in the form of a solid by: (1) cooling the reaction mixture; (2) concentrating the solution and then cooling; or (3) concentration and treatment with other solvents in which the lavendamycin analogs are not soluble. Such solvents include ethyl acetate, pentane, hexane, cyclohexane, petroleum ether, diethyl ether, and acetone.

Aldehyde K can be prepared by the selenium dioxide oxidation of the corresponding 2-methylquinoline-5,8-dione (M) in refluxing dioxane-$H_2O$.

Formula M

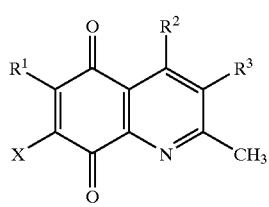

The 2-methylquinoline-5,8-diones M can be prepared by the Diels-Alder condensation of a I-silyloxy-azadiene (N) with a bromoquinone (O) in refluxing chlorobenzene for 24 hours. See Equation 2 below. Bromoquinone (O) can be prepared according to the method described in Kelly et al., *J. Org. Chem.*, 48, 3849 (1983) (see Example 27)

Equation 2

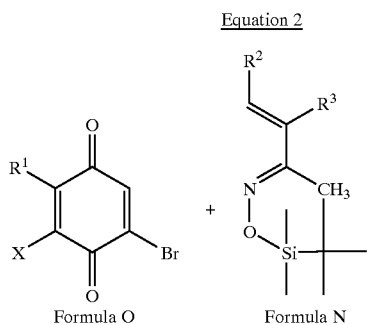

The azadiene N can be prepared by the reaction of a silyloxyamine (P) with a ketone (Q) in dichloromethane at room temperature for 48 hours in the presence of molecular sieves. See Equation 3 below.

Equation 3

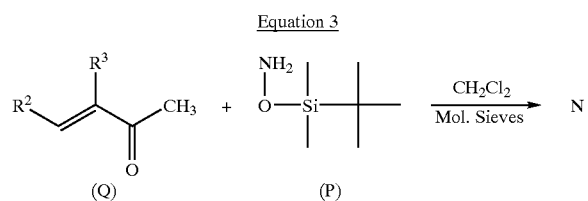

Some of the 2-methylquinoline-5,8-diones M can also be prepared by the oxidation of the corresponding acylamido compounds (R) with potassium dichromate in glacial acetic acid. See Equation 4 below.

Equation 4

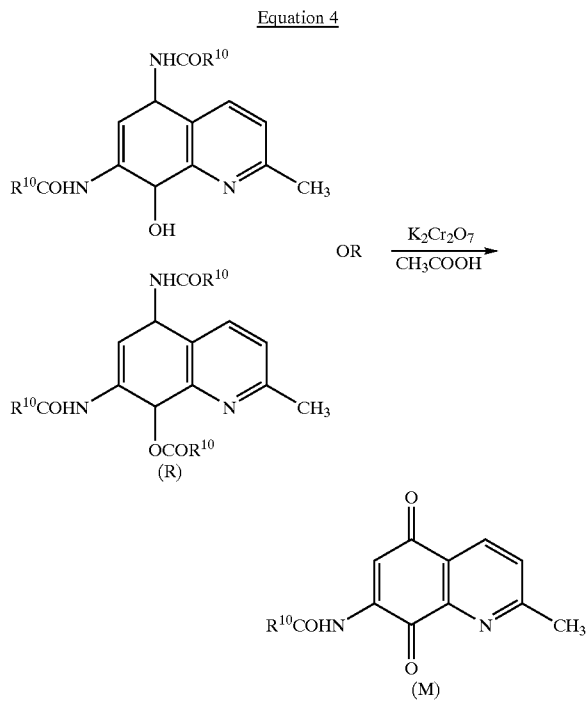

The acylamido compounds R may be prepared by the reduction of the 5,7-dinitro-8-hydroxy-2-methylquinolines (S) by molecular hydrogen in the presence of palladium on carbon followed by treatment with the desired anhydride (T). See Equation 5.

Equation 5

$$\text{S} \xrightarrow{\substack{1.\ H_2/PdC,\ HCl\text{—}H_2O \\ 2.\ (R^{10}CO)_2O,\ Na_2SO_3,\ CH_3COONa}} \text{R}$$

Tryptophan and its analogs suitable for use in the method of the invention are available commercially or can be made by methods known in the art. For instance, tryptophan analogs 35, 38, 42 and 43 (see Table VI) are commercially available in their salt forms. Also, the following tryptophan analogs useful in the practice of the invention are commercially available from Sigma Chemical Co., St. Louis, Mo.: N-t-BOC-L-tryptophan p-nitrophenyl ester; N-CBZ-L-tryptophan p-nitrophenyl ester; DL-tryptophanamide hydrochloride; L-tryptophan benzyl ester hydrochloride; DL-tryptophan butyl ester hydrochloride; DL-tryptophan ethyl ester hydrochloride; L-tryptophan ethyl ester; D-tryptophan methyl ester hydrochloride; L-tryptophan methyl ester; DL-tryptophan octyl ester hydrochloride; 5-methoxy-DL-tryptophan; 5-fluorotryptamine hydrochloride; 6-fluorotryptamine; DL-4-fluorotryptophan; 5-fluoro-DL-tryptophan; 6-fluoro-DL-tryptophan; 5-hydroxy-D-tryptophan; 5-hydroxy-DL-tryptophan; 5-hydroxy-L-tryptophan; 5-hydroxy-DL-tryptophan ethyl ester hydrochloride. Other tryptophan analogs are available from other sources or can be made by methods known in the art.

For instance, tryptophan esters can be prepared by reacting tryptophan or an appropriately functionalized tryptophan with an alcohol to give the desired ester. See Equation 6 below.

Equation 6

Alkylaminoalkyl esters can be prepared by protecting the amine on the tryptophan (or functionalized tryptophan analog) and then reacting the protected tryptophan with the appropriate alkylaminoalkyl halide as described in Matao Kanaoka et al., *J. Phar. Soc. of Japan*, 95, 231 (1975). See Equation 7 below.

Equation 7

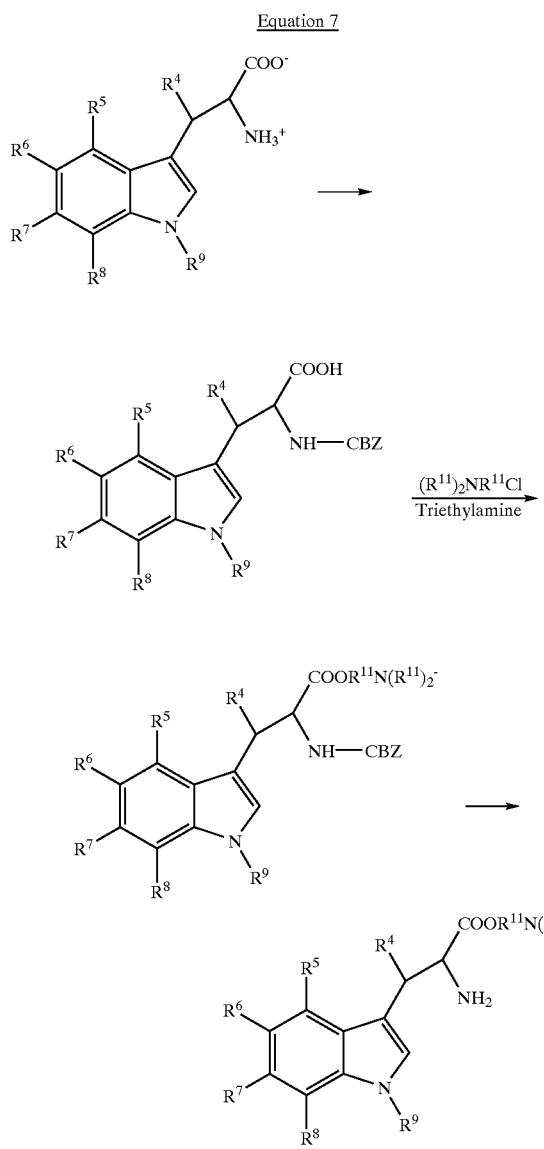

Tryptophan esters of tertiary alcohols can be prepared by the method of Rosowsky et al., *J. Med. Chem.*, 24, 1450 (1981) as shown in Equation 8:

Equation 8

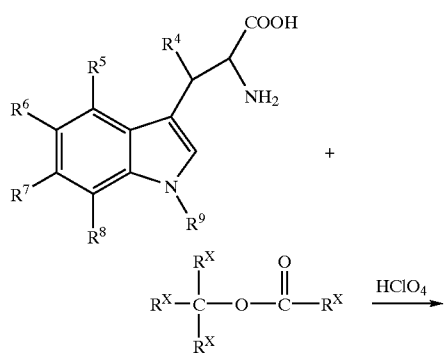

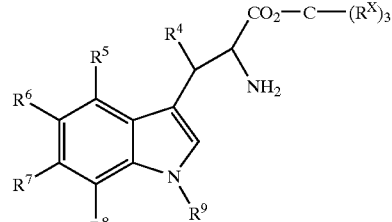

wherein $R^x$ is an alkyl, and each $R^x$ may be the same or different.

Tryptophan aryl esters can be prepared by the methods of Castro et al. *Synthesis*, 413 (1977) and Rosowsky et al. *J. Med. Chem.*, 24, 1450 (1981) as shown in Equation 9:

Equation 9

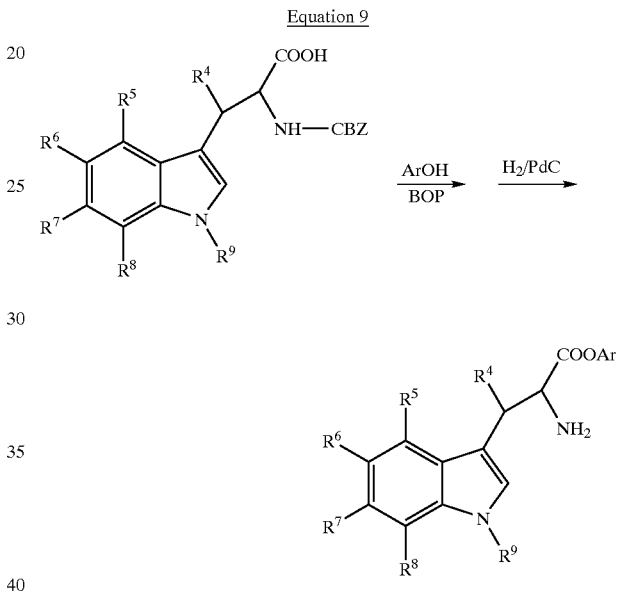

Finally, tryptophan esters and amides can be prepared by the neutralization of the commercially available salts with, e.g., ammonium hydroxide, followed by extraction.

In addition to the method of preparing the lavendamycin analogs of the invention just described, the lavendamycin analogs can also be prepared by means of a Bischer-Napieralski condensation of an appropriately functionalized quinoline-2-carboxylic acid (U) with an appropriately functionalized tryptophan L. This method is similar to the method described in Kende et al., *Tetrahedron Letters*, 25, 923 (1984).

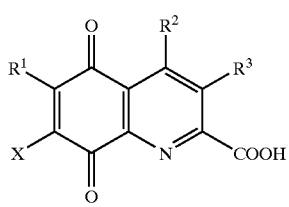

The lavendamycin analogs of the invention are useful as antitumor, antibacterial, antiviral and antiparasitic agents. For instances, they can be used to treat bacterial infections caused by both gram-positive and gram-negative bacteria, for example, bacteria of the genus Staphylococcus (such as *Staphylococcus aureus*), Streptococcus (such as *Streptococcus agalactine* and *Streptococcus faecalis*), Micrococcus (such as *Micrococcus luteus*), Bacillus (such as *Bacillus subtilis*), Listerella (such as *Listerella monocytogenes*), Escherichia (such as *Escherichia coli*), Klebsiella (such as *Klebsiella pneumoniae*), Proteus (such as *Proteus mirabilis* and *Proteus vulgaris*), Salmonella (such as *Salmonella typhosa*), Shigella (such as *Shigella sonnei*), Enterobacter (such as *Enterobacter aerogenes*), Serratia (such as *Serratia marcescens*), Pseudomonas (such as *Pseudomonas aeruginosa*), Acinetobacter such as *Acinetobacter anitratus*), Nocardia (such as *Nocardia autotrophica*), and Mycobacterium (such as *Mycobacterium fortuitum*).

The lavendamycin analogs of the invention also have antiviral activity. For instance, they can be used to treat viral infections caused by the Retroviridae (e.g., HIV-1, HIV-2, HTLV-I and HTLV-II), Herpesviridae (e.g., herpes simplex, varicella zoster, Epstein-Barr virus, and herpes genitalia), Hepadnaviridae (e.g., hepatitis B), Picornaviridae (e.g., hepatitis A virus and poliomyelitis virus), hepatitis non A non B virus, Orthomyxoviridae (e.g., influenza virus), Poxviridae (e.g., variola virus and vaccinia virus), Flaviviridae (e.g., yellow fever virus), Rubiviridae (e.g, rubella virus), Paramyxoviridae (e.g., measles, parainfluenza, mumps and canine distemper viruses), Rhabdoviridae (e.g., rabies virus), Papovaviridae, and Adenoviridae.

Moreover, some of the lavendamycin analogs, namely compounds B described above, and compounds 1, 2, 12, 16, 17, 20 and 21 described below, have been shown to have anti-HIV reverse transcriptase activity (See Example 57 below). These compounds were shown to have relatively low toxicity. These compounds were also shown to have remarkable additive effectiveness when combined with 3'-azido-3'deoxythymidine.

The lavendamycin analogs can also be used to treat parasitic infections, including those caused by Amoeba, Giardia, Babesia, Balantidium, Eimeriorina, Entamoeba, Histomonas, Naegleria, Nosema, Plasmodium, Toxoplasma, Trypanosoma and Trypanosomatidae.

The lavendamycin analogs also have antitumor activity. They may be used to treat a variety of tumors, including ovarian, colon, breast, cervical, esophageal, glioblastoma, neuroblastoma, stomach, kidney, skin, lung, pancreatic, seminoma, melanoma, bladder, thyroid, myeloid and lymphoid tumors. They have been found to be especially effective against solid tumors and malignant tumors.

In particular, certain of the lavendamycin analogs of the invention have unexpectedly been found to be selectively active against $ras^K$ tumor cells. By "selectively active," it is meant that these lavendamycin analogs are more cytotoxic towards the $ras^K$ tumor cells than towards normal cells. Example 47 describes a method of determining which lavendamycin analogs are selectively active against $ras^K$ tumor cells. Other methods are known in the art.

The lavendamycin analogs of the invention which have been found to be selectively active against $ras^K$ tumor cells are those compounds of formula J wherein:

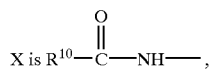

$R^{10}$ is an alkyl,

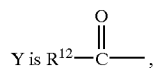

$R^{12}$ is $OR^{11}$ or $OR^{14}N(R^{11})_2$,
$R^{11}$ is an alkyl,
$R^4$ is H or an alkyl, and
$R^6$ is H.

Three of these compounds have been found to exhibit unprecedented highly selective activity against $ras^K$ tumor cells. They are compounds of formula J wherein:

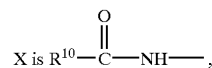

$R^{10}$ is $CH_3$,

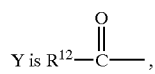

$R^{12}$ is $OR^{11}$,
$R^{11}$ is methyl, isoamyl, or n-octyl,
$R^4$ is $CH_3$ when $R^{11}$ is methyl, and $R^4$ is H when $R^{11}$ is isoamyl or n-octyl, and
$R^6$ is H.

The $ras^K$ oncogene has been associated with the causation of a large number of human solid tumors, including 90% of pancreatic cancers, 60% of colon cancers and 30% of breast cancers. Prior to the present invention there were no effective drugs available to treat patients with solid tumors whose malignant phenotype was maintained by the $ras^K$ oncogene.

One lavendamycin analog, namely 6-chlorolavendamycin methyl ester has also shown activity in the NCI Hollow Fiber Assay For Preliminary In Vivo Testing (see Example 56 below).

The quinolinediones also have antitumor activity. They may be used to treat a variety of tumors, including ovarian, colon, breast, kidney, lung, prostate, central nervous system, melanoma, and lymphoid tumors. They have been found to be especially effective against solid tumors and malignant tumors.

Treatment of bacterial, viral and parasitic infections according to the invention includes both mitigation, as well as elimination, of the infection. Treatment of tumors includes maintaining or reducing the size of, or eliminating, the tumor.

To treat an animal suffering from a microbial (bacterial, viral or parasitic) infection, an effective amount of a lavendamycin analog of the invention, or a pharmaceutically-acceptable salt thereof, is administered to the animal. Animals treatable according to the invention include mammals such as dogs, cats, other domestic animals, and humans.

To treat an animal suffering from an HIV infection, an effective amount of a lavendamycin analog, or a pharmaceutically-acceptable salt thereof, is administered to the animal, preferably in combination with other compounds such as nucleoside analog inhibitors of HIV reverse transcriptase, most preferably in combination with 3'-azido'3'-deoxythymidine (AZT).

To treat an animal having a tumor, an effective amount of a lavendamycin analog or quinoline dione of the invention, or pharmaceutically-acceptable salts thereof, is administered to the animal. Animals treatable according to the invention include mammals such as dogs, cats, other domestic animals, and humans.

Effective dosage forms, modes of administration and dosage amounts of the lavendamycin analogs and quinolinediones may be determined empirically, and making such determinations is within the skill of the art. It is understood by those skilled in the art that the dosage amount will vary with the activity of the particular lavendamycin analog or quinolinedione employed, the severity of the microbial infection or tumor, the route of administration, the rate of excretion of the lavendamycin analog or quinolinedione, the duration of the treatment, the identity of any other drugs being administered to the animal, the age, size and species of the animal, and like factors well known in the medical and veterinary arts. In general, a suitable daily dose of a compound of the present invention will be that amount of the compound which is the lowest dose effective to produce a therapeutic effect. Exemplary daily dosages of the lavendamycin analogs are those within the range of from about 1 mg/kg/day to about 3 g/kg/day, preferably from 10 mg/kg/day to 500 mg/kg/day. Exemplary daily dosages of the quinoline diones are those within the range of from about 1 mg/kg/day to about 3 g/kg/day, preferably from 10 to 500 mg/kg/day. However, the total daily dosage of the lavendamycin analog or quinolinedione will be determined by an attending physician or veterinarian within the scope of sound medical judgment. If desired, the effective daily dose of a lavendamycin analog or a quinoline-dione, or pharmaceutically-acceptable salts thereof, may be administered as two, three, four, five, six or more sub-doses, administered separately at appropriate intervals throughout the day.

The compounds of the present invention may be administered to an animal patient for therapy by any suitable route of administration, including orally, nasally, rectally, intravaginally, parenterally, intracisternally and topically, as by powders, ointments or drops, including buccally and sublingually. The preferred routes of administration are orally and parenterally.

While it is possible for a compound of the present invention to be administered alone, it is preferable to administer the compound as a pharmaceutical formulation (composition). The pharmaceutical compositions of the invention comprise one or more of the compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the compounds of the present invention, are formulated into pharmaceutically-acceptable dosage forms by conventional methods known to those of skill in the art.

The amount of active ingredient (a lavendamycin analog, quinolinedione, or pharmaceutically-acceptable salts thereof which will be combined with a carrier material to produce a single dosage form will vary depending upon the host being treated, the particular mode of administration and all of the other factors described above. The amount of active ingredient which will be combined with a carrier material to produce a single dosage form will generally be that amount of the compound which is the lowest dose effective to produce a therapeutic effect.

Methods of preparing pharmaceutical formulations or compositions include the step of bringing into association a compound of the present invention with the carrier and, optionally, one or more accessory ingredients are known in the art. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as bolus, electuary or paste.

In solid dosage forms of the invention for oral administration (capsules, tablets, pills, dragees, powders, granules and the like), the active ingredient (a lavendamycin analog, a quinolinedione, or pharmaceutically-acceptable salts thereof is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract and/or in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient (a lavendamycin analog, a quinolinedione, or pharmaceutically-acceptable salts thereof, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

The lavendamycin analogs of the invention may also be employed as antimicrobial (antibacterial, antiviral, antiparasitic) agents useful in inhibiting the growth of microbes. "Inhibition of growth" as used herein includes killing of the microbes. For instance, the compounds of the invention may be used to inhibit the growth of microbes present on a surface or in a medium outside a living host. The invention, therefore, provides a method for inhibiting the growth of a bacterium, virus or parasite comprising the step of contacting the microbe with a lavendamycin analog of the invention, or a salt thereof, in an amount effective for the inhibition. Thus, the lavendamycin analogs of the invention may be employed, for example, as disinfectants for surface treatments or as preservatives for a variety of solid and liquid media susceptible to microbial growth. Effective amounts of a lavendamycin analog for such uses may be determined empirically by methods known to the skilled artisan.

EXAMPLES

Examples 1–46

Synthesis of Lavendamycin Analogs

Examples 1–46 describe the synthesis of 22 lavendamycin analogs. The synthesis of 8 quinoline-diones is also described. The following general procedures were utilized in Examples 1–46. Melting points (uncorrected) were determined on a Thomas Hoover capillary apparatus and are in degrees Celsius. Infrared (IR) spectra were obtained with a Nicolet 5ZDX spectrophotometer. Proton magnetic resonance ($^1$H NMR) spectra were obtained with a Varian Gemini-200 spectrophotometer in CDCl$_3$ or DMSO-d$_6$ with tetramethylsilane (TMS) as internal standard. Mass spectra (MS) were obtained with a Hewlett-Packard 5980A instrument fitted with a vacummetrics solid probe or with a Kratos MS 50. Elemental analyses were performed by Midwest Microlabs, Ltd.

Examples 1–22

Synthesis of 7-N-Acyllavendamycins

The 22 lavendamycin analogs which were prepared have formula J:

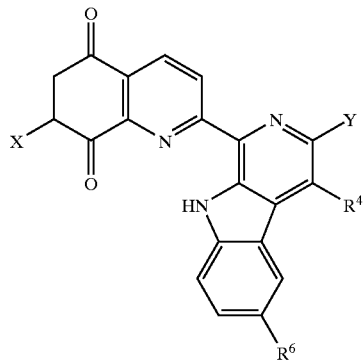

Formula J wherein:

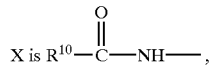

$R^{10}$ is an alkyl or substituted alkyl,

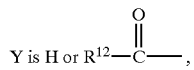

$R^4$ is H or an alkyl,
$R^6$ is H, a halogen atom or $OR^{13}$,
$R^{12}$ is $N(R^{11})_2$, $OR^{11}$ or $OR^{14}N(R^{11})_2$,
$R^{11}$ is H, an alkyl or a cycloalkyl,
$R^{13}$ is an alkyl, and
$R^{14}$ is an alkylene.

Table I contains a list of the lavendamycin analogs and specifies the substituents for each analog.

The lavendamycin analogs were prepared by reacting an appropriately functionalized aldehyde K with an appropriately functionalized tryptophan analog L as described above (see Equation 1 above). The reaction conditions and yields for the 22 lavendamycin analogs are listed in Table I, and the procedures used to make 11 of the analogs are described in detail below. Table II gives the $^1$H NMR, MS and high resolution MS (HRMS) values for the 22 analogs.

7-N-Acetyllavendamycin Methyl Ester (Compound 1, Table I): A stirred mixture of aldehyde 23 (prepared as described in Example 23) (12.02 mg, 0.05 mmol) and tryptophan ester 39 (prepared as described in Behforouz et al., *J. Heterocycl. Chem.*, 25, 1627 (1988); see Example 39 below) (11.6 mg, 0.05 mmol) and dry xylene (16 mL) under argon was slowly heated (3 hours) to boiling and then refluxed for 19 hours. The solution was concentrated to 5 mL and then cooled. The pure orange crystals of the 7-N-acetyllavendamycin methyl ester were filtered. A yield of 17.8 mg, 78.4%, was obtained. The melting point (mp) was >300° C. IR (KBr) 3473 (br), 3310, 3121, 1728, 1708, 1680, 1645, 1588, 1504, 1398, 1335, 1307, 1229, 1124, 738 cm$^{-1}$; $^1$H NMR (CDCl$_3$)*2.38 (s,3,COCH$_3$), 3.19 (s,3,ArCH$_3$), 4.07 (s,3,CO$_2$CH$_3$), 7.39 (t,1,J=8 Hz.,H—11'), 7.65 (t,1,J=8 Hz.,H—10'), 7.74 (d,1,J=8 Hz., H—9'), 8.00 (s,1,H—6), 8.35 (d,1,J=8 Hz., H—12'), 8.41 (br s,1,CONH), 8.5 (d,1, J=7 Hz.,H—3), 9.1 (d,1,J=7.5 Hz.,H—4); 11.85 (br s,1,NH); MS m/e (relative intensity) 454 (M$^+$,68), 396 (14), 394 (25), 352 (17), 106 (36), 91 (100), 77 (14), 54 (14); HRMS, m/e for C$_{25}$H$_{18}$N$_4$O$_5$ calculated 454.1277, found 454.1277.

7-N-ACETYLDEMETHYLLAVENDAMYCIN (Compound 2, Table I): L-tryptophan (20.4 mg, 0.1 mmol) and anisole were stirred and heated in a 60–70° C. oil bath. Then, a mixture of 7-N-acetamido-2-formylquinoline-5,8-dione (23) (prepared as described in Example 23) (24.4 mg, 0.1 mmol) and 20 ml anisole was added dropwise over a one-hour period. The mixture was heated in the oil bath at 120° C. for 23.5 hr. and rotoevaporated to dryness. The residue was chromato-graphed on a silicon gel column (4 g silica gel, column 13 cm×10 cm), and eluted with $CH_2Cl_2$ (50 ml), methanol: $CH_2Cl_2$ (2.5:100, 100 ml) to give orange crystals (0.6 mg., yield 1.4%).

7-N-CHLOROACETYLLAVENDAMYCIN METHYL ESTER (Compound 7, Table I): In a 40 ml. round-bottomed flask equipped with a reflux condenser, argon-filled balloon and a magnetic bar, 7-chloroacetamido-2-formylquinoline-5,8-dione (24) (prepared as described in Example 24) (0.0278 g., 0.10 mmol), b-methyltryptophan methyl ester (39) (prepared as described in Behforouz et al., *J. Heterocycl. Chem.*, 25, 1627 (1988); see Example 39 below) (0.0232 g., 0.10 mmol), and 40 ml. of dried, distilled xylene were slowly heated to 135° C. over a three-hour period. The mixture was heated at this temperature for an additional 16 hours. A light brown precipitate began to form at the maximum temperature. The completion of the reaction was monitored by TLC. The mixture was filtered hot to remove the precipitated impurities, and the filtrate was allowed to cool, resulting in the formation of an orange-red solid. This solid was filtered, collected, and dried under vacuum. The yield of the product was 0.0226 g. (46%): mp >300° C.; $^1$H NMR (DMSO-$d_6$)*3.08 (3H, s, ArCH$_3$), 3.97 (3H, s, COCH$_3$), 4.64 (2H, s, C—7NHCO$\underline{CH}_2$Cl), 7.42 (1H, dd, J=8.4 Hz., J=8.4 Hz., C—11'H), 7.69 (1H, dd, J=8.4 Hz., J=8.4 Hz., C—10'H), 7.71 (1H, d, J=8.4 Hz., C—9'H), 7.75 (1H, s, C—6H), 8.40 (1H, d, J=8.4 Hz., C—12'H), 8.50 (1H, d, J=8.4 Hz., C—3H), 8.64 (1H, d, J=8.4 Hz., C—4H), 10.58 (1H, br s, C—7NH), 11.94 (1H, br s, NH); IR (KBr) $v_{max}$3342, 3106, 3010, 2950, 1679, 1652, 1589, 1507, 1492, 1339, 1307, 742 cm$^{-1}$; electron impact MS (EIMS), m/e (relative intensity) 488/490 (M$^+$, 2.25/1, 16), 454 (96), 412 (base), 394 (36), 380 (20), 352 (88), 335 (29); HRMS, m/e for $C_{25}H_{17}ClN_4O_5$ calculated 488.088748, found 488.087100.

7-N-CHLOROACETYLDEMETHYLLAVENDAMYCIN ISOAMYL ESTER (Compound 9, Table I): In a 100 ml. three-necked, round-bottomed flask equipped with a reflux condenser, flowing argon and a magnetic bar, 7-chloro-acetamido-2-formylquinoline-5,8-dione (24) (prepared as described in Example 24) (0.0500 g., 0.18 mmol), L-tryptophan isoamyl ester (37) (prepared as described in Example 37) (0.0490 g., 0.18 mmol), and 75 ml. of dried and distilled xylene were slowly heated to 76 EC over a five-hour period. Upon the first detection of the formation of a light-colored precipitate, the mixture was filtered hot. The filtrate was concentrated under reduced pressure to about 10 ml. The filtrate was stored in a refrigerator overnight during which a considerable amount of a dark orange-brown solid formed. This was filtered and washed with cold ethyl acetate giving 25.5 mg. of the crude product (a yield of 27%). The filtrate was further concentrated which, upon cooling, yielded an additional 15 mg. of the product (16% yield, total yield 43%): mp. 280–284 EC; $^1$H NMR (CDCl$_3$)*1.05 (6H, d, J=6.3 Hz., ($\underline{CH}_3$)$_2$), 1.76–1.95 (3H, m, COOCH$_2$$\underline{CH}_2$$\underline{CH}$), 4.29 (2H, s, C—7NHCO$\underline{CH}_2$Cl), 4.52 (2H, t, J=6.8 Hz., COOCH$_2$), 7.39 (1 H, dd, J=8.0 Hz., J=8.0 Hz., C—11'H), 7.66 (1H, dd, J=8.0 Hz., J=8.0 Hz., C—10'H), 7.78 (1H, d, J=8.0 Hz., C—9'H), 7.95 (1H, s, C—6H), 8.23 (1H, d, J=8.0 Hz., C—12'H), 8.54 (1H, d, J=8.3 Hz., C—3H), 8.93 (1H, s, C—3'H), 9.18 (1H, d, J=8.3 Hz., C—4H), 9.56 (1H, brs, C—7NH), 11.76 (1H, brs, NH); IR (KBr) $v_{max}$ 3336, 2957, 2929, 2908, 2871, 1713, 1680, 1651, 1588, 1520, 1337, 1308, 1265, 1219, 1119, 738 cm$^{-1}$; EIMS, m/e (relative intensity) 530/532 (M$^+$, 2.4/1, 45), 496 (58), 480 (6), 454 (39), 416 (83), 382 (95), 366 (15), 340 (base); HRMS, m/e for $C_{28}H_{23}ClN_4O_5$ calculated 530.135698, found 530.135781.

7-N-CHLOROACETYLDEMETHYLLAVENDA-MYCIN OCTYL ESTER (Compound 10, Table I): In a 50 ml. three-necked round-bottomed flask equipped with a reflux condenser, flowing argon and a magnetic bar, 7-chloroacetamido-2-formylquinoline-5,8-dione (24) (prepared as described in Example 24) (0.0279 g., 0.10 mmol), L-tryptophan octyl ester (38) (prepared as described in Example 38) (0.0316 g., 0.10 mmol), and 32 ml. of dried and distilled xylene were slowly heated to 100° C. over a six-hour period. This temperature was maintained for an additional 2.5 hours. During the last three hours, a brown precipitate formed. TLC of the mixture indicated the major spot to be the desired product. The mixture was filtered hot to remove the precipitated impurities, and the filtrate was rotoevaporated to dryness affording 0.0301 g. of a dark-red solid which $^1$H NMR indicated was crude product (yield of 53%). The crude product was further purified by recrystallization with ethyl acetate: mp 215–217° C.; $^1$H NMR (CDCl$_3$)*0.88 (3H, t, J=6.8 Hz., (CH$_2$)$_7$$\underline{CH}_3$)), 1.23–1.70 (10'H, ($\underline{CH}_2$)$_5$CH$_3$)), 1.84–1.95 (2H, m, COOCH$_2$$\underline{CH}_2$), 4.29 (2H, s, C—7NHCO$\underline{CH}_2$Cl), 4.48 (2H, t, J=6.8 Hz., COOCH$_2$), 7.39 (1H, dd, J=7.6 Hz., J=7.6 Hz., C—11'H), 7.66 (1H, dd, J=7.6 Hz., J=7.6 Hz., C—10'H), 7.79 (1H, d, J=7.6 Hz., C—9'H), 7.97 (1H, s, C—6H), 8.24 (1H, d, J=7.6 Hz., C—12'H), 8.56 (1H, d, J=8.4 Hz., C—3H), 8.95 (1H, s, C—3'H), 9.21 (1H, d, J=8.4 Hz., C—4H), 9.58 (1H, br s, C—7NH), 11.79 (1H, br s, NH); IR (KBr) $v_{max}$ 3331, 2955, 2926, 2854, 1708, 1680, 1652, 1588, 1519, 1337, 1307, 1264, 1219, 738 cm$^{-1}$; EIMS, m/e (relative intensity) 573 (M$^+$, 1), 538 (10), 496 (35), 382 (53), 366 (30), 340 (base); HRMS, m/e for $C_{35}H_{40}ClN_4O_7S_2$ calculated 727.202696, found 727.200500.

7-N-BUTYRYLLAVENDAMYCIN METHYL ESTER (Compound 11, Table I): In a 25 ml. round-bottomed flask equipped with a reflux condenser, argon-filled balloon, and a magnetic bar, 7-butyramido-2-formylquinoline-5,8-dione (26) (prepared as described in Example 26) (0.0272 g., 0.10 mmol), b-methyltryptophan methyl ester (39) (prepared as described in Example 39) (0.0232 g., 0.10 mmol), and 30 ml. of dried and distilled xylene were slowly heated to 130° C. over a three-hour period. This temperature was maintained for an additional 16 hours, during which a slight amount of a light brown precipitate formed. The completion of the reaction was monitored by TLC. The mixture was filtered hot to remove the precipitate. The filtrate was then concentrated under reduced pressure to the point of crystallization and then allowed to cool. The orange-red solid was filtered and then dried under vacuum. The weight of the solid was 0.0210 g. (a yield of 44%): mp. 270–273° C.; $^1$H NMR (CDCl$_3$)*1.06 (3H, t, J=7.6 Hz., C—7NHCOCH$_2$CH$_2$$\underline{CH}_3$), 1.75–1.90 (2H, m, C—7NHCOCH$_2$$\underline{CH}_2$CH$_3$), 2.52 (2H, t, J=7.6 Hz., C—7NHCO$\underline{CH}_2$CH$_2$CH$_3$), 3.16 (3H, s, Ar—CH$_3$), 4.07 (3H, s, COCH$_3$), 7.36 (1H, dd, J=8.0 Hz., J=8.0 Hz., C—11'H), 7.63 (1H, dd, J=8.0 Hz., J=8.0 Hz., C—10'), 7.70 (1H, d, J=8.0 Hz., C—9'H), 7.92 (1H, s, C—6H), 8.31 (1H, d, J=8.0 Hz., C—12'H), 8.34 (1H, brs, C—7NH), 8.41 (1H, d, J=8.3 Hz., C—3H), 9.01 (1H, d, J=8.3 Hz., C—4H), 11.76 (1H, br s, NH); IR (KBr) $v_{max}$ 3316, 3199, 2959, 2933, 2874, 1724, 1710, 1679, 1646, 1586, 1501, 1335, 1307, 1227 cm$^{-1}$; EIMS, m/e (relative intensity) 482 (M$^+$, base), 466 (11), 450 (13), 422 (32), 380 (9), 352 (35), HRMS, m/e for $C_{27}H_{22}N_4O_5$ calculated 482.159020, found 482.160385.

7-N-BUTYRYLDEMETHYLLAVENDAMYCIN ISOAMYL ESTER (Compound 13, Table I): In a 50 ml. three-necked, round-bottomed flask equipped with a reflux condenser, flowing argon, and a magnetic bar, 7-butyramido-2-formylquinoline-5,8-dione (26) (prepared as described in Example 26) (0.0279 g., 0.10 mmol), L-tryptophan isoamyl ester (37) (prepared as described in Example 37) (0.0274 g., 0.10 mmol), and 30 ml. of dried and distilled xylene were slowly heated to reflux over a four-hour period. This temperature was maintained for an additional 17 hours. A small amount of an orange-brown solid was formed. The completion of the reaction was monitored by TLC. The mixture was filtered hot to remove the precipitate which was not the product. The filtrate was concentrated under reduced pressure to approximately 2 ml. Upon cooling, this solution yielded a bright orange precipitate which weighed 0.0166 g. (32% yield). The mother liquor was evaporated to dryness to yield an additional amount of crude product that weighed 0.0198 g. (38% yield), giving a total yield of 70%: mp. 234–235E C; $^1$H NMR (CDCl$_3$)*1.04 (6H, d, J=6.8 Hz., (CH$_3$)$_2$), 1.06 (3H, t, J=7.4 Hz., C—7NHCOCH$_2$CH$_2$CH$_3$), 1.75–1.95 (5H, m, C—7NHCOCH$_2$CH$_2$, COOCH$_2$CH$_2$CH), 2.53 (2H, t, J=7.4 Hz., C—7NHCOCH$_2$), 4.52 (2H, t, J=6.8 Hz., COOCH$_2$), 7.39 (1H, dd, J=7.8 Hz., J=7.8 Hz., C—11'H), 7.66 (1H, dd, J=7.8 Hz., J=7.8 Hz., C—10'H), 7.74 (1H, d, J=7.8 Hz., C—9'H), 7.99 (1H, s, C—6H), 8.24 (1H, d, J=7.8 Hz., C—12'H), 8.41 (1H, br s, C—7NH), 8.55 (1H, d, J=8.4 Hz., C—3'H), 8.94 (1H, s, C—3'H), 9.18 (1H, d, J=8.4 C—4H), 11.80 (1H, br s, NH); IR (KBr) $v_{max}$ 3369, 3346, 3313, 2960, 2935, 2873, 1728, 1715, 1700, 1681, 1646, 1587, 1494, 1335, 1307, 1261, 1221, 1119, 739 cm$^{-1}$; EIMS, m/e (relative intensity) 524 (69), 454 (6), 410 (base), 394 (5), 340 (22); HRMS, m/e for $C_{30}H_{28}N_4O_5$ calculated 524.205970, found 524.207494.

7-N-BUTYRYLDEMETHYLLAVENDAMYCIN OCTYL ESTER (Compound 14, Table I): In a 50 ml. three-necked, round-bottomed flask equipped with a reflux condenser, flowing argon, and a magnetic bar, 7-N-butyramido-2-formylquinoline-5,8-dione (26) (prepared as described in Example 26) (0.0230 g., 0.085 mmol), L-tryptophan octyl ester (38) (prepared as described in Example 38) (0.0270 g., 0.085 mmol), and 30 ml. of dried and distilled xylene were slowly heated to 85 EC over a five hour period. This temperature was maintained for an additional 16 hours. During this period a small amount of a dark precipitate appeared. The completion of the reaction was monitored by TLC. The mixture was filtered hot to remove the precipitated impurities, and the filtrate was rotoevaporated to dryness affording 0.0386 g. of a dark-red solid which $^1$H NMR indicated was crude product (yield of 80%). The crude product was further purified by recrystallization from ethyl acetate: mp. 166–171E C; $^1$H NMR (CDCl$_3$)*0.86 (3H, t, J=6.8 Hz., (CH$_2$)$_7$CH$_3$), 1.06 (3H, t, J=7.3 Hz., C—7NHCOCH$_2$CH$_2$CH$_3$), 1.20–1.60 (10'h, (CH$_2$)$_5$CH$_3$), 1.65–1.95 (4H, m C—7NHCOCH$_2$CH$_2$, COOCH$_2$CH$_2$), 2.53 (2H, t, J=7.3 Hz., C—7NHCOCH$_2$), 4.47 (2H, t, J=6.8 Hz., COOCH$_2$), 7.36 (1H, dd, J=8.0 Hz., J=8.0 Hz., C—11'H), 7.63 (1H, dd, J=8.0 Hz., J=8.0 Hz., C—10'H), 7.65 (1H, d, J=8.0 Hz., C—9'H), 7.93 (1H, s, C—6H), 8.19 (1H, d, J=8.0 Hz., C—12'H), 8.35 (1H, br s, C—7NH), 8.44 (1H, d, J=8.4 Hz., C—3H), 8.87 (1H, s, C—3'H), 9.08 (1H, d, J=8.4 Hz., C—4H), 11.67 (1H, br s, NH); IR (KBr) $v_{max}$ 3317, 2957, 2926, 2855, 1728, 1704, 1679, 1646, 1587, 1504, 1333, 1307, 1260, 1222, 1118, 739 cm$^{-1}$; EIMS, m/e (relative intensity) 566 (M$^+$, 14), 550 (45), 534 (15), 496 (6), 410 (12), 394 (base), 378 (22), 340 (17); HRMS, m/e for $C_{33}H_{34}N_4O_5$ calculated 566.252921, found 566.251991.

7-N-ACETYLDEMETHYLLAVENDAMYCIN CARBOXAMIDE (Compound 16, Table I): 7-N-Acetamido-2-formylquinoline-5,8-dione (23) (prepared as described in Example 23) (42.3 mg 0.15 mmol), L-tryptophan amide (43) (prepared as described in Example 43) (30.44 mg, 0.015 mmol) and anisole (60 ml) were heated slowly in an oil bath from room temperature to 160° C. over a 2.5-hr. period, and then held 160° C. for 14 hr. The reaction mixture was cooled in the refrigerator for 3 hr. Then it was filtered to give a lemon yellow solid. The solid was washed with hexane and dried to give 39.6 mg., a yield of 62%.

7-N-ACETYLDEMETHYLLAVENDAMYCIN METHYL ESTER (Compound 17, Table I): 7-N-Acetamido-2-formylquinoline-5,8-dione (23) (prepared as described in Example 23) (44.8 mg, 0.2 mmol), L-tryptophan methyl ester (35) (prepared as described in Example 35) (43.6 mg, 0.2 mmol), dry xylene (90 ml) were mixed. The mixture was stirred and slowly heated in an oil bath from room temperature to 140° C. over a 3-hr period and from 140° C. to 154° C. over a 20-hr period. The reaction mixture was allowed to cool to room temperature to give 53 mg (yield of 60%) of a yellow solid.

7-N-ACETYLLAVENDAMYCIN ISOAMYL ESTER (Compound 18, Table I): 7-Acetamido-2-formylquinoline-5,8-dione (23) (prepared as described in Example 23) (44.8 mg, 0.2 mmol), b-methyltryptophan isoamyl ester (36) (prepared as described in Example 36) (57.6 mg, 0.2 mmol) and 64 ml of dry xylene were stirred and heated slowly in an oil bath from room temperature to 140 EC over a 3-hour period and was then kept at 140° C. for 1 hour. The hot reaction mixture was filtered to give an orange solid. The filtrate afforded more product upon cooling. The total weight obtained of the product was 60.2 mg, a 59% yield.

7-N-ACETYLLAVENDAMYCIN N,N-DIMETHYLAMINOETHYL ESTER (Compound 19, Table I): 7-Acetamido-2-formylquinoline-5,8-dione (23) (prepared as described in Example 23) (317 mg, 0.13 mmol) was dissolved in 16 ml of dry anisole and heated to 80° C. b-methyltryptophan N,N-dimethylaminoethyl ester (41) (prepared as described in Example 41) (37.5 mg, 0.13 mmol) was added with stirring, and the stirred mixture was heated at 100° C. for 5.5 hr. The reaction mixture was allowed to cool to room temperature and the solid was filtered. The filtrate was distilled under vacuum to dryness. Ethyl acetate (3 ml) was added, and the mixture was stirred. Upon filtration 24.5 mg (a yield of 36%) of an orange solid was obtained.

7-N-ACETYLDEMETHYLLAVENDAMYCIN ISOAMYL ESTER (Compound 20, Table I): 7-Acetamido-2-formylquinoline-5,8-dione (23) (prepared as described in Example 23) (244 mg, 0.1 mmol), L-tryptophan isoamyl ester (37) (prepared as described in Example 37) (239 mg, 1 mmol) and xylene (64 ml) were mixed. The mixture was stirred and slowly heated in an oil bath from room temperature to 110° C. over a one-hour period, and then from 110° C. to 140° C. over a 3-hr period. The hot reaction mixture was filtered to remove the brown impurity. The filtrate was evaporated under vacuum. The residue was treated with ethyl-acetate/hexane to give an orange solid (213 mg, 42% yield).

7-N-ACETYLDEMETHYLLAVENDAMYCIN n-OCTYL ESTER (Compound 21, Table I):

7-Acetamido-2-formylquinoline-5,8-dione (23) (prepared as described in Examples 23–26) (44.8 mg, 0.2 mmol), L-tryptophan N-octyl ester (38) (prepared as described in Example 38) (63.2 mg, 0.2 mmol) and 64 ml of dry xylene were stirred and slowly heated in an oil bath from room temperature to 150° C. over a 3-hr period and then maintained at 150° C. for 2h. The hot mixture was filtered, and the brown solid was collected. More brown solid was obtained from the filtrate upon treatment with ethylacetate and hexane (total yield 51 mg, 48%).

7-N-ACETYLDEMETHYLLAVENDAMYCIN N,N-DIMETHYLAMINOETHYL ESTER (Compound 22, Table I):

7-Acetamido-2-formylquinoline-5,8-dione (23) (prepared as described in Example 23) (12.2 mg, 0.05 mmol), L-tryptophan N,N-dimethylaminoethyl ester (40) (prepared as described in Example 40) (14 mg, 0.05 mmol) and 18 ml of anisole were heated at 100° C. for 27 h. The mixture was allowed to cool to room temperature and was filtered to remove impurities. The filtrate was evaporated under reduced pressure, and the resulting residue was dissolved in 6 ml of $CHCl_3$ and purified by thick layer chromatography on alumina. A pure orange solid (5 mg, 20% yield) was obtained.

TABLE I

| Compd. | $R^{10}$ | Y | $R^4$ | $R^6$ | Solvent | Hours (° C.) | Yield (%) |
|---|---|---|---|---|---|---|---|
| 1 | $CH_3$ | $CO_2CH_3$ | $CH_3$ | H | Xylene | 19 (reflux) | 78.4 |
| 2 | $CH_3$ | $CO_2H$ | H | H | Anisole | 23.5 (120N) | 1.4 |
| 3 | $CH_3$ | $CH_2CH_2CO_2CH\,CH_2CH_2CH_2$ | H | H | Xylene | 3 (25N-reflux) 1 (reflux) | 59 |
| 4 | $CH_3$ | $CO_2(CH_2)_3CH_3$ | H | $OCH_3$ | Anisole | 6 (70–90N) | 66 |
| 5 | $CH_3$ | $CO_2(CH_2)_3CH_3$ | H | F | Anisole | 5 (120N) | 49 |
| 6 | $CH_3$ | H | H | H | Anisole | 3 (25–160N) 16 (160N) | 54 |
| 7 | $ClCH_2$ | $CO_2CH_3$ | $CH_3$ | H | Xylene | 16 (135N) | 46 |
| 8 | $ClCH_2$ | $CO_2(CH_2)_3CH_3$ | H | H | Xylene | 3 (<76N) 5.75 (76N) | 20 |
| 9 | $ClCH_2$ | $CO_2(CH_2)_2CH(CH_3)_2$ | H | H | Xylene | 5 (#76N) | 43 (crude) |
| 10 | $ClCH_2$ | $CO_2(CH_2)_7CH_3$ | H | H | Xylene | 6 (<100N) 2.5 (100N) | 53 (crude) |
| 11 | $CH_3(CH_2)_2$ | $CO_2CH_3$ | $CH_3$ | H | Xylene | 16 (130N) | 44 |
| 12 | $CH_3(CH_2)_2$ | $CO_2(CH_2)_3CH_3$ | H | H | Xylene | 55 (130N) | 30 |
| 13 | $CH_3(CH_2)_2$ | $CO_2(CH_2)_2CH(CH_3)_2$ | H | H | Xylene | 4 (25N-reflux) 17 (reflux) | 70 (crude) |
| 14 | $CH_3(CH_2)_2$ | $CO_2(CH_2)_7CH_3$ | H | H | Xylene | 5 (<85N) 16 (85N) | 80 (crude) |
| 15 | $(CH_3)_2CH$ | $CO_2(CH_2)_3CH_3$ | H | H | Xylene | 8 (125N) | 65.2 |
| 16 | $CH_3$ | $CONH_2$ | H | H | Anisole | 2.5 (<160N) 14 (160N) | 62 |
| 17 | $CH_3$ | $CO_2CH_3$ | H | H | Xylene | 3 (<140N) 20 (154N) | 60 |
| 18 | $CH_3$ | $CO_2CH_2CH_2CH(CH_3)_2$ | $CH_3$ | H | Xylene | 3 (<140N) 1 (140N) | 59 |
| 19 | $CH_3$ | $CO_2(CH_2)_2N(CH_3)_2$ | $CH_3$ | H | Anisole | 5.5 (100N) 1 (<140N) | 36 |
| 20 | $CH_3$ | $CO_2CH_2CH_2CH(CH_3)_2$ | H | H | Xylene | 1 (140N) 3 (<150N) | 42 |
| 21 | $CH_3$ | $CO_2(CH_2)_7CH_3$ | H | H | Xylene | 3 (<180N) 2 (150N) | 48 |
| 22 | $CH_3$ | $CO_2CH_2CH_2N(CH_3)_2$ | H | H | Anisole | 27 (100N) | 20 |

TABLE II

| Compound | $R^{10}$ | Y | $R^4$ | $R^6$ | $^1H$, NMR | MS | HRMS |
|---|---|---|---|---|---|---|---|
| 1 | $CH_3$ | $CO_2CH_3$ | $CH_3$ | H | 2.38(s, 3H), 3.22(s, 3H), 4.10(s, 3H), 7.42(dd, J=7.6Hz, 1H), 7.68(dd, J=7.6Hz, 1H), 7.77(d, J=8.2Hz, 1H), 8.00(s, 1H), 8.38(d, J=8.2Hz, 1H), 8.44(s, 1H), 8.53(d, J=8.2Hz, 1H), 9.13(d, J=8.2Hz, 1H), 11.88(br s, 1H) | 454($M^+$, 68), 396(14), 394(25), 352(17), 106(36), 91(100), 77(14), 54(14) | $C_{25}H_{18}N_4O_5$ Calc. 454.1277 Found 454.1277 |
| 2 | $CH_3$ | $CO_2H$ | H | H | 2.37(s, 3H), 7.65(dd, 1H), 7.70(dd, 1H), 8.0(s, 1H), 8.13(d, 1H), 8.21(d, 1H), 8.45(br s, 1H), 8.57(d, 1H), 8.62(s, 1H), 9.11(d, 1H), 11.65(br s, 1H) | | |
| 3 | $CH_3$ | $CH_2$—$CH_2$ $CO_2CH\,CH_2$ $CH_2$—$CH_2$ | H | H | 1.66–2.17(m, 10H), 2.37(s, 3H), 5.20(m, 1H), 7.41(dd, 1H), 7.68(dd, 1H), 7.75(d, 1H), 7.98(s, 1H), 8.27(d, 1H), 8.42(br s, 1H), 8.56(d, 1H), | 508($M^+$, 35), 426(12), 382(base), 366(15), 340(25), 312(5), 283(4), | $C_{29}H_{24}N_4O_5$ Calc. 508.174670 Found 508.173290 |

TABLE II-continued

| Compound | $R^{10}$ | Y | $R^4$ | $R^6$ | $^1$H, NMR | MS | HRMS |
|---|---|---|---|---|---|---|---|
| 4 | $CH_3$ | $CO_2(CH_2)_3CH_3$ | H | $OCH_3$ | 8.95(s, 1H), 9.22(d, 1H), 11.8(br s, 1H) 1.04(t, 3H), 1.6–1.85(m, 4H), 2.38(s, 3H), 4.0(s, 3H), 4.35(t, 2H), 7.33(d, 1H), 7.66(d, 1H), 7.67(s, 1H), 7.99(s, 1H), 8.42(br s, 1H), 8.57(d, 1H), 8.93(s, 1H), 9.22(d, 1H), 11.7(br s, 1H) | 256(6), 154(4), 130(4) 512/513($M^+$, base), 412(30), 397(6), 355(8) | $C_{28}H_{24}N_4O_6$ Calc. 512.169585 Found 512.168362 |
| 5 | $CH_3$ | $CO_2(CH_2)_3CH_3$ | H | F | 1.07(s, 3H), 1.89–1.25(m, 4H), 2.37(s, 3H), 4.51(t, 2H), 7.19(s, 1H), 7.92(d, 1H), 7.94(d, 1H), 8.02(s, 1H), 8.45(br s, 1H), 8.62(d, 1H), 8.93(s, 1H), 9.25(d, 1H), 11.88(br s, 1H) | | |
| 6 | $CH_3$ | H | H | H | 2.37(s, 3H), 7.35(dd, 1H), 7.68(dd, 1H), 7.71(d, 1H), 7.99(s, 1H), 8.13(d, 1H), 8.21(d, 1H), 8.45(br s, 1H), 8.61(d, 1H), 8.56(d, 1H), 9.10(d, 1H), 11.64(br s, 1H) | 382/383($M^+$ base), 340(58), 313(24), 284(12), 244(19), 140(10) | $C_{22}H_{12}N_4O_3$ Calc. 340.096026 Found 340.095347 |
| 7 | $ClCH_2$ | $CO_2CH_3$ | $CH_3$ | H | (DMSO) 3.08(s, 3H), 3.97(s, 3H), 4.64(s, 2H), 7.42(dd, J=8.4Hz, 8.4Hz, 1H), 7.69(dd, J=8.4, 8.4Hz, 1H), 7.71(d, J=8.4Hz, 1H), 7.75(s, 1H), 8.40(d, J=8.4Hz, 1H), 8.50(d, J=8.4Hz, 1H), 8.64(d, J=8.4Hz, 1H), 10.58(br s, 1H), 11.94(br s, 1H) | 488/490($M^+$ 2.25/1, 16), 454(96), 412(base), 394(36), 380(20), 352(88), 335(29) | $C_{25}H_{17}ClN_4O_5$ Calc 488.088748 Found 488.087100 |
| 8 | $ClCH_2$ | $CO_2(CH_2)_3CH_3$ | H | H | 1.06(t, 3H), 1.85–1.95(m, 4H), 4.25(s, 2H), 4.50(t, 2H), 7.35–7.45(m, 1H), 7.65–7.73(t, 1H), 7.80–7.84(t, 1H), 8.01(s, 1H), 8.25–8.79(d, 1H), 8.58–8.62(d, J=8.34Hz, 1H), 8.98(s, 1H), 9.23–9.27(d, J=8.38Hz, 1H), 9.62(br s, 1H), 11.8(br s, 1H) | 482($M^+$–Cl+1, 41.2), 466(base), 440(46.6), 424(32.4), 382(30.2), 364(15.3), 352(23.0), 350(7.9), 340(300), 326(25.9), 325(15.0), 281(41.7), 207(94.1), 182(14.3), 181(14.2), 168(59.9), 129(14.9), 117(47.5), 115(21.3) | |
| 9 | $ClCH_2$ | $CO_2(CH_2)_2CH(CH_3)_2$ | H | H | 1.05(d, J=6.3Hz, 6H), 1.76–1.95 (m, 3H), 4.29(s, 2H), 4.52(t, J=6.8Hz, 2H), 7.39(dd, J=8.0, 8.0Hz, 1H), 7.66(dd, J=8.0, 8.0Hz, 1H), 7.78(d, J=8.0Hz, 1H), 7.95(s, 1H), 8.23(d, J=8.0Hz, 1H), 8.54(d, J=8.3Hz, 1H), 8.93(s, 1H), 9.18(d, J=8.3Hz, 1H), 9.56(br s, 1H), 11.76(br s, 1H). | 530/532($M^+$ 2.4/1, 45) 496(58), 480(6), 454(39), 416(83), 382(95), 366(15), 340(base). | $C_{28}H_{23}ClN_4O_5$ Calc 530.135698 Found 530.135781 |
| 10 | $ClCH_2$ | $CO(CH_2)_7CH_3$ | H | H | 0.88(t, J=6.8Hz, 3H), 1.23–1.70(m, 10H), 1.84–1.95(m, 2H), 4.29(s, 2H), 4.48(t, J=6.8Hz, 2H), 7.39(dd, J=7.6, 7.6Hz, 1H), 7.66(dd, J=7.6Hz, 7.6Hz, 1H), 7.79(d, J=7.6Hz, 1H), 7.97(s, 1H), 8.24(d, J=7.6Hz, 1H), 8.56(d, J=8.4Hz, 1H), 8.95(s, 1H), 9.21(d, J=8.4Hz, 1H), 9.58(br s, 1H), 11.79(br s, 1H) | 573($M^+$, 1), 538(10), 496(35), 382(53), 366(30), 340(base) | $M+C_4H_{10}O_2S_2$ $C_{35}H_{40}ClN_4O_5S_2$ Calc 727.202696 Found 727.200500 |
| 11 | $CH_3(CH_2)_2$ | $CO_2CH_3$ | $CH_3$ | H | 1.06(t, J=7.6Hz, 3H), 1.75–1.90(m, 2H), 2.52(t, J=7.6Hz, 2H), 3.16(s, 3H), 4.07(s, 3H), 7.36(dd, J=8.0, 8.0Hz, 1H), 7.63(dd, J=8.0, | 482($M^+$, base) 466(11), 450(13) 422(32), 380(9), 352(35) | $C_{27}H_{22}N_4O_5$ Calc 482.159020 Found 482.160385 |

TABLE II-continued

| Compound | $R^{10}$ | Y | $R^4$ | $R^6$ | $^1$H, NMR | MS | HRMS |
|---|---|---|---|---|---|---|---|
| | | | | | 8.0Hz, 1H), 7.70(d, J=8.0Hz, 1H), 7.92(s, 1H), 8.31(d, J=8.0Hz, 1H), 8.34, (br s, 1H) | | |
| 12 | $CH_3(CH_2)_2$ | $CO_2(CH_2)_3CH_3$ | H | H | 1.10(t, 6H), 1.6(m, 2H), 1.85–2.00(m, 4H), 2.55(t, 2H), 4.50(t, 2H), 7.38(t, 1H), 7.65–7.70(m, 2H), 7.97(s, 1H), 8.20–8.24(d, 1H), 8.39(br s, 1H), 8.50–8.54(d, J=8.3Hz, 1H), 8.92(s, 1H), 9.13–9.23(d, J=8.2Hz, 1H), 11.75(br s, 1H) | 510(M+, 69), 494(21.4), 446(11.8), 417(11.5), 410(base), 394(35.9), 379(10.3), 340(38.4) 339(16.7), 217(130) | $C_{29}H_{26}N_4O_5$ Calc 510.090320 Found 510.091661 |
| 13 | $CH_3(CH_2)_2$ | $CO_2(CH_2)_2CH(CH_3)_2$ | H | H | 1.04(d, J=6.8Hz, 6H), 1.06(t, J=7.4Hz, 3H), 1.75–1.95(m, 5H), 2.53(t, J=7.4Hz, 2H), 4.52(t, J=6.8Hz, 2H), 7.39(dd, J=7.8, 7.8Hz, 1H), 7.66(dd, J=7.8, 7.8Hz, 1H), 7.74(d, J=7.8Hz, 1H), 7.99(s, 1H), 8.24(d, J=7.8Hz, 1H), 8.41(br s, 1H), 8.55(d, J=8.4Hz, 1H), 8.94(s, 1H), 9.18(d, J=8.4Hz, 1H), 11.80(br s, 1H) | 524(69), 454(6), 410(base), 394(5), 340(22) | $C_{30}H_{28}N_4O_5$ Calc 524.205970 Found 524.207494 |
| 14 | $CH_3(CH_2)_2$ | $CO_2(CH_2)_7CH_3$ | H | H | 0.86(t, J=6.8Hz, 3H), 1.06(t, J=7.3Hz, 3H), 1.20–1.60(m, 10H), 1.65–1.95(m, 4H), 2.53(t, J=7.3Hz, 2H), 4.47(t, J=6.8Hz, 2H), 7.36(dd, J=8.0, 8.0Hz, 1H), 7.63(dd, J=8.0, 8.0Hz, 1H), 7.65(d, J=8.0Hz, 1H), 7.93(s, 1H), 8.19(d, J=8.0Hz, 1H), 8.35(br s, 1H), 8.44(d, J=8.4Hz, 1H), 8.87(s, 1H), 9.08(d, J=8.4Hz, 1H), 11.67(br s, 1H) | 566(M+, 14), 550(45), 534(15), 496(6), 410(12), 394(base), 378(22), 340(17) | $C_{33}H_{34}N_4O_5$ Calc 566.252921 Found 566.251991 |
| 15 | $(CH_3)_2CH$ | $CO_2(CH_2)_3CH_3$ | H | H | 1.04(t, J=7.3Hz, 7.32Hz, 3H), 1.33(d, J=6.68Hz, 6H), 2.73(m, J=6.76Hz, 6.88Hz, 1H), 4.49(t, J=6.88, 6.58Hz, 2H), 7.39(d, J=7.3Hz, 1H), 7.41(dd, J=7.3Hz, 1H), 7.73(dd, J=7.3Hz, 1H), 7.99(s, 1H), 8.24(d, J=8Hz, 1H), 8.49(s, 1H), 8.55(d, J=8.4Hz, 1H), 8.94(s, 1H), 9.18(d, J=8.4Hz, 1H), 11.8(br s, 1H) | 510/512(M+, base), 494(37.1), 492(22.4), 469(5.8), 440(6), 410(18.1), 394(35.4), 337(9.7) | $C_{29}H_{26}N_4O_5$ Calc 510.190320 Found 510.188750 |
| 16 | $CH_3$ | $CONH_2$ | H | H | 2.23(s, 3H), 7.39(t, 1H), 7.70(t, 1H), 7.79(d, 1H), 8.46(br s, 1H), 8.57(d, 1H), 9.05(s, 1H), 9.06(d, 1H), 9.61(s, 1H), 9.77(br s, 2H), 10.15(d, 1H), 12.39(br s, 1H) | 425(M+, base), 409(50), 382(23), 366(31), 340(25) | $C_{23}H_{15}N_5O_4$ Calc. 425.112404 Found 425.11150 |
| 17 | $CH_3$ | $CO_2CH_3$ | H | H | 2.38(s, 3H), 4.12(s, 3H), 7.40(dd, 1H), 7.76(dd, 1H), 7.76(d, 1H), 8.03(s, 1H), 8.27(d, 1H), 8.48(br s, 1H), 8.62(d, 1H), 9.03(s, 1H), 9.26(d, 1H), 11.82(br s, 1H) | 443(M+3, base), 441(23), 440(81), 439(14), 438(39) | $C_{24}H_{16}O_5N_4$ Calc. 440.112070 Found 440.111984 |
| 18 | $CH_3$ | $CO_2CH_2CH_2CH(CH_3)_2$ | $CH_3$ | H | 1.06(d, 6H), 1.8–1.9(m, 3H), 2.37(s, 3H), 3.19(s, 3H), 4.53(t, 2H), 7.40(dd, 1H), 7.60(dd, 1H), 7.70(d, 1H), 7.97(s, 1H), 8.36(d, 1H), 8.39(br s, 1H), 8.50(d, 1H), 9.10(d, 1H), 11.80(br s, 1H) | 510(M+68), 396(90), 354(21), 281(16) | $C_{29}H_{26}O_5N_4$ Calc. 510.190320 Found 510.187804 |
| 19 | $CH_3$ | $CO_2CH_2CH_2N(CH_3)_2$ | $CH_3$ | H | 2.37(s, 3H), 2.43(s, 6H), 2.8(t, 2H), 3.2(s, 3H), 4.6(t, 2H), 7.40(dd, 1H), 7.69(dd, 1H), 7.74(d, 1H), 7.97(s, 1H), 8.3(d, 1H), 8.4(br s, 1H), 8.5(d, 1H) 9.10(d, 1H), 11.80(br s, 1H) | 514(M+3+ 20), 425(17), 397(21), 387(16), 355(30), 207(17), 155(51), 147(48), 119(base) | |
| 20 | $CH_3$ | $CO_2CH_2CH_2CH(CH_3)_2$ | H | H | 1.06(d, 6H), 1.8–1.9(m, 3H), 2.38(s, 3H), 4.54(t, 2H), 7.41(dd, 1H), 7.69(dd, 1H), 7.71(d, 1H), 8.01(s, 1H), 8.27(d, 1H), 8.45(br s, 1H), | 496(M+55), 382(100), 340(17) | $C_{28}H_{24}O_5N_4$ Calc. 496.174610 Found 496.175570 |

TABLE II-continued

| Compound | $R^{10}$ | Y | $R^4$ | $R^6$ | $^1$H, NMR | MS | HRMS |
|---|---|---|---|---|---|---|---|
| 21 | $CH_3$ | $CO_2(CH_2)_7CH_3$ | H | H | 8.58(d, 1H), 8.97(s, 1H), 9.22(d, 1H), 11.80(br s, 1H) 0.89(t, 3H), 1.33(m, 10H), 1.95(m, 2H), 2.37(s, 3H), 4.5(t, 2H), 7.43(dd, 1H), 7.70(dd, 1H), 7.73(d, 1H), 8.0(s, 1H), 8.26(d, 1H), 8.44(br s, 1H), 8.6(d, 1H), 8.97(s, 1H), 9.2(d, 1H), 11.8(br s, 1H) | 538($M^+$, 55), 382(100), 366(5), 340(16) | $C_{31}H_{30}N_4O_5$ Calc. 538.221620 Found 538.222007 |
| 22 | $CH_3$ | $CO_2CH_2CH_2N(CH_3)_2$ | H | H | 2.38(s, 3H), 2.47(s, 6H), 2.93(t, 2H), 4.63(t, 2H), 7.44(dd, 1H), 7.69(dd, 1H), 7.70(d, 1H), 7.98(s, 1H), 8.24(d, 1H), 8.42(br s, 1H), 8.5(d, 1H), 8.96(s, 1H), 9.17(d, 1H), 11.79(br s, 1H) | 391(12), 279(10), 167(25), 150(17), 149(base), 113(26) | |

Examples 23–26

Preparation of Quinolinedione Aldehydes

The starting materials for preparing the lavendamycin analogs of Examples 1–22 include the 7-N-acyl-2-formylquinoline-5,8-diones of formula K:

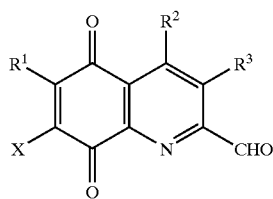

Formula K wherein

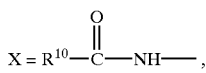

$R^{10}$ is an alkyl or substituted alkyl,
$R^1$=H,
$R^2$=H, and
$R^3$=H.

These aldehydes were prepared by the selenium dioxide oxidation of the corresponding 7-N-acyl-2-methylquinoline-5,8-diones in refluxing dioxane-$H_2O$ as described above. Table III lists four such aldehydes prepared by this method and the reaction times, yields, $^1$H NMR, MS and elemental analysis for these aldehydes. The procedures used to synthesize three of these aldehydes are described in detail below.

7-ACETAMIDO-2-FORMYLQUINOLINE-5,8-DIONE (Compound 23, Table III): A mixture of 7-acetamido-2-methylquinoline-5,8-dione (27) (prepared as described in Example 27) (230 mg, 1 mmol), selenium dioxide (139 mg, 1.25 mmol) in dry dioxane (3.5 mL) and water (0.13 mL) was stirred and refluxed under argon for 9 hours. A fresh grade of 99.9+% of $SeO_2$ (Aldrich) was used. Dioxane was purified and distilled according to the procedure described in Perrin et al., *Purification Of Laboratory Chemicals* (Pergammon Press 1980). Dioxane (7 mL) was added, allowed to reflux for 10 min., and then filtered hot. The residue on the filter paper was added to the reaction flask containing 20 mL of dichloromethane, refluxed for 5 min and filtered. This process was repeated four more times. The filtrates were combined and evaporated to give 222 mg (yield of 91 %) of a yellow solid which was 7-acetamido-2-methyl-quinoline-5,8-dione (23). An analytical sample obtained by sublimation (150–180 EC/0.5 mm): mp 225 EC dec.; IR (KBr) 3346, 3085, 1721, 1687, 1652, 1609, 1504, 1328, 1216, 1124, 1068, 885 $cm^{-1}$; $^1$H NMR ($CDCl_3$)*2.33 (s,3,$COCH_3$), 8.05 (s,1,H—6), 8.31 (d,1,J=8Hz,H—3), 8.43 (br s,1,NH), 8.62 (d,1,J=8Hz,H—4), 10.29 (s,1,CHO); MS m/e (relative intensity) 244 ($M^+$, 81), 216 (19), 202 (51), 175 (37), 174 (21), 97 (19), 85 (20), 71 (30), 68 (18), 57 (34), 43 (100). Elemental analysis calculated for $C_{12}H_8N_2O_4$: C, 59.02; H, 3.30; N, 11.47; Found: C, 58.99; H, 3.38; N, 10.91.

7-CHLOROACETAMIDO-2-FORMYLQUINOLINE-5,8-DIONE (Compound 24, Table III): In a 25 ml. round-bottomed flask equipped with a magnetic bar, water-cooled reflux condenser, and argon-filled balloon, 7-chloroacetamido-2-methylquinoline-5,8-dione (28) (prepared as described in Example 28) (0.529 g., 2 mmol), selenium dioxide (0.255 g., 2.3 mmol), 12 ml of dried, distilled 1,4-dioxane, and 0.25 ml. of water were stirred and slowly heated to reflux over a two-hour period. The reaction was monitored by TLC and allowed to go to completion (29.5 hours). The selenium was allowed to settle, and the supernatant solution was pipetted off and filtered. 1,4-Dioxane (10 ml.) was added to the residue, stirred and refluxed for five minutes. The entire mixture was filtered and the selenium was washed with dichloromethane (10 ml.). All filtrates were combined and stored at 4 EC overnight. Solid precipitate from the chilled mixture was filtered yielding 0.0985 9. of crude product (yield of 18%). This was purified by recrystallization from ethyl acetate/dichloromethane. The original remaining filtrate was diluted with 50 ml of dichloromethane and washed with 3% sodium bicarbonate solution (2×50 ml.). The aqueous layer was then extracted with dichloromethane (2× 20 ml.) The organic layers were dried with magnesium sulfate and rotoevaporated to give a dark orange solid. The product was dried under vacuum overnight and 0.2941 g. of product was obtained (yield of 52%, total 70%). This product could be further purified by flash chromatography and recrystallization from ethyl acetate/dichloromethane: mp 190–192 EC; $^1$H NMR ($CDCl_3$)*4.26 (2H, s, C—7NHCO$CH_2$Cl), 8.04 (1H, s, C—6H), 8.33 (1H, d, J=8.1 Hz, C—3H), 8.62 (1H, d, J=8.1 Hz, C—4H), 9.54 (1H, br. s, C—7NH), 10.28 (1H, s, C—2CHO); IR (KBr)

$v_{max}$ 3310, 3089, 2950, 2852, 1731, 1720, 1678, 1644, 1521, 1118 cm$^{-1}$; EIMS, m/e (relative intensity) 278/280 (M$^+$, 2.7/1, 95), 243 (33), 229 (33), 215 (55), 202 (base), 175 (61), 146 (17); HRMS, m/e for $C_{14}H_9ClN_2O_3$ calculated 278.009435, found 278.008764; analysis for $C_{14}H_9ClN_2O_3$ calculated C, 51.72; H, 2.53; Cl, 12.72; N, 10.05; Found C, 51.81; H, 2.9; Cl, 12.79; N, 9.86.

7-BUTYRAMIDO-2-FORMYLQUINOLINE-5,8-DIONE (Compound 26, Table III): In a 25 ml. round-bottomed flask equipped with a magnetic bar, water-cooled reflux condenser, and an argon filled balloon, 7-butyramido-2-methylquinoline-5,8-dione (30) (prepared as described in Example 30) (0.516 g., 2 mmol), selenium dioxide (0.255 g., 2.3 mmol), 12 ml. of dried, distilled 1,4-dioxane, and 0.25 ml. of water were stirred and slowly heated to reflux over a two-hour period. The reaction was monitored by TLC and found to be complete after 33.5 hours. The selenium metal was allowed to settle, and the supernatant solution was pipetted off and filtered. 1,4-Dioxane (10 ml.) was added to the residue, stirred and refluxed for five minutes. The entire mixture was filtered and the selenium was washed with dichloromethane (10 ml.). All filtrates were combined and stored at 4 EC overnight. This solution was diluted with 50 ml of dichloromethane and washed with a 3% sodium bicarbonate solution (2×50 ml.). The organic layer was dried with magnesium sulfate and rotoevaporated to give a pale yellow product. The solid was dried under vacuum overnight and weighed 0.356 g. (yield of 65%). The product was recrystallized from ethyl acetate: mp. 208–210 E C; $^1$H NMR (CDCl$_3$)*1.02 (3H, t, J=7.4 Hz, C—7NHCOCH$_2$CH$_2$CH$_3$), 1.70–1.89 (2H, m, 7NHCOCH$_2$CH$_2$CH$_3$), 2.52 (2H, t, J=7.4 Hz, 7NHCOCH$_2$CH$_2$CH$_3$), 8.06 (1H, s, C—6H), 8.31 (1H, d, J=8.0 Hz, C—3H), 8.39 (1H, br. s, C—7NH), 8.61 (1H, d, J=8.0 Hz, C—4H), 10.28 (1H, s, C—2CHO); IR (KBr) $v_{max}$ 3299, 3081, 2966, 2935, 2876, 1723, 1694, 1638, 1606, 1505 cm$^{-1}$; EIMS, m/e (relative intensity) 272 (54), 202 (36), 175 (9); HRMS, m/e for $C_{14}H_{12}N_2O_4$ calculated 272.079707, found 272.078696; analysis for $C_{14}H_{12}N_2O_4$ calculated C, 61.76; H, 4.44; N, 10.29; found C, 61.31; H, 4.36; N, 9.94.

Examples 27–30

Preparation of 7-Acetamido-2-Methylquinoline-5,8-diones

The 7-N-acyl-2-methylquinoline-5,8-diones used as starting materials in Examples 23–26 are compounds of formula M:

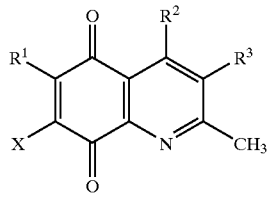

Formula M wherein

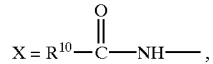

$R^{10}$ is an alkyl or substituted alkyl,
$R^1$=H,
$R^2$=H, and
$R^3$=H.

They were prepared by one of two methods: (1) The oxidation of the corresponding acylamido compounds with potassium dichromate in glacial acetic acid as illustrated in Equation 4 above; or (2) The Diels-Alder condensation of a 1-silyloxy-azadiane with a 2-acetamido-6-bromobenzoquinone as illustrated in Equation 2 above. Table IV lists four 7-N-acyl-2-methylquinoline-5,8-diones, their % yields, melting points, elemental analyses, $^1$H NMR and MS. The following are the detailed procedures used for the preparation of these quinolinediones.

7-ACETAMIDO-2-METHYLQUINOLINE-5,8-DIONE (Compound 27, Table IV):

TABLE III

| Compound | R$^{10}$ | Hr. | % Yield | mp (° C.) | $^1$H, NMR (CDCl$_3$) | MS | Elemental Analysis or HRMS |
|---|---|---|---|---|---|---|---|
| 23 | CH$_3$ | 9 | 91 | 225 (dec) | 2.33(s, 3H), 8.05(s, 1H), 8.31(d, 1H), 8.43(br s, 1H), 8.62(d, 1H), 10.29(s, 1H) | 244(M$^+$, 81), 216(19), 202(51), 175(37), 174(21), 97(19), 85(20), 71(30), 68(18), 57(34), 43(base) | Calc.: C, 59.02; H, 3.30; N, 11.47; Found: C, 58.99; H, 3.38; N, 10.91 |
| 24 | ClCH$_2$ | 29.5 | 70(crude) | 190–192 | 4.26(s, 2H), 8.04(s, 1H), 8.33(d, J=8.1Hz, 1H), 8.62(d, J=8.1Hz, 1H), 9.54(br s, 1H), 10.28(s, 1H) | 278/280(M$^+$, 2.7/1, 95), 248(33), 229(33), 215(55), 202(base), 175(61), 146(17) | $C_{14}H_9ClN_2O_3$ Calc. 278.009435 Found 278.008764 |
| 25 | (CH$_3$)$_2$CH | 20 | 65 | 183–184 | 1.29(d, J=7Hz, 6H), 2.67–2.72(m, J=6.92, 6.88, 6.96Hz, 1H), 8.06(s, 1H), 8.3(d, J=8Hz, 1H), 8.4(s, 1H), 8.6(d, J=8Hz, 1H), 10.29(s, 1H) | 272(M$^+$, Base), 229(4.5), 217(4.1), 203(26.4), 175(4.7) | |
| 26 | CH$_3$(CH$_2$)$_2$ | 33.5 | 65(crude) | 208–210 | 1.02(t, J=7.4Hz, 3H), 1.70–1.89(m, 2H), 2.52(t, J=7.4Hz, 2H), 8.06(s, 1H), 8.31(d, J=8.0Hz, 1H), 8.39(br s, 1H), 8.61(d, J=8.0Hz, 1H), 10.28(s, 1H) | 272(M$^+$, 54), 202(36), 175(9) | $C_{14}H_{12}N_2O_4$ Calc. 272.079707 Found 272.078696 Calc. C: 61.76, H: 4.44, N: 10.29 Found C: 61.31, H: 4.36, N: 9.94 |

This compound was prepared by the oxidation of the corresponding acylamido with potassium dichromate in glacial acetic acid. Into a 1000 ml Erlenmeyer flask, 240 ml of glacial acetic acid, and 5,7-diacetamido-2-methyl-8-acetoxyquinoline (31) (prepared as described in Example 31) (6.3 g, 2.0 mmol) were added. To the resulting suspension, a solution of potassium dichromate (17.64 g) in 200 ml of water was added. This black solution was magnetically stirred at room temperature for 20–24 hours. The solution was then poured into 900 ml of water and extracted with dichloromethane (5×200 ml). The organic extracts were washed with a solution of 5% sodium carbonate in a saturated salt solution (3×300 ml). The organic layer was dried overnight with anhydrous magnesium sulfate. The magnesium sulfate was filtered off, and the solvent was evaporated to leave an orange/yellow solid. The solid 7-acetamino-2-methylquinoline-5,8-dione (27) was dried overnight under vacuum. 2.6 g of product was obtained for a yield of 56%.

7-ACETAMIDO-2-METHYLQUINOLINE-5,8-DIONE (27): 7-Acetamido-2-methylquinoline-5,8-dione (27) was also prepared by Diels-Alder condensation of a 1-silyloxy-azadiene with 2-acetamido-6-bromobenzoquinone. The azadiene was prepared by the reaction of methyl vinyl ketone with t-butyldimethylsilyloxyamine in the presence of molecular sieves as illustrated in Equation 2 above. In a dry 50 mL round-bottomed flask containing 5.7 g of dry molecular sieve 4AN, 1.4 g(0.02 mol) of freshly distilled methyl vinyl ketone in 10 mL dry dichloromethane was placed. Then a solution of the O(tert-butyldimethylsilyl) hydroxylamine (Aldrich) in 5 mL of dry dichloromethane was added. The mixture was stirred at room temperature under argon for 48 h and then filtered off. Evaporation of the solution under reduced pressure and fractional distillation of the residue afforded 2.04 g(51% yield, bp 67–71° C./8 mm) of azadiene. Nuclear magnetic resonance spectroscopy showed the product to be an E/Z mixture (7:3) which was used as such in the next reaction. An analytical sample of the major isomer was obtained by silica gel column chromatography using petroleum ether and then petroleum ether plus ethylacetate (200:1) as solvents. IR (liquid film) 2959, 2931, 2860, 1630, 1581, 1462, 1363, 1251, 1061, 983, 948, 871, 836, 808, 787, 674 cm$^{-1}$; $^1$H NMR (CDCl$_3$)*0.15 (s,6,Si(CH$_3$)$_2$), 0.91 (s,9,C(CH$_3$)$_3$), 1.95 (s,3,C—2CH$_3$), 5.35–5.57 (m,2,=CH$_2$), 6.38–6.52 (m,1,=CH); MS, m/e (relative intensity) 199 (M$^+$, 0.3), 142 (100), 75 (68), 68 (97), 42 (20); Elemental analysis calculated for C$_{10}$H$_{21}$NOSi: C, 60.24; H, 10.62; N, 7.03; found: C, 60.22; H, 10.56; N, 7.10.

Then, 7-acetamido-2-methylquinoline-5,8-dione (27) was prepared. A solution of bromoquinone (317 mg, 1.3 mmol), 1-(tert-butyldimethylsilyloxy)-2-methyl-1-aza-1,3-butadiene (130 mg, 0.65 mmol) in 28 mL dry chlorobenzene was refluxed under argon for 22 h. Chlorobenzene (10 mL) was added and refluxed for another 2 h. The reaction mixture was allowed to cool and then put onto a silica gel column (2×9.5 cm). The column was eluted with ethylacetate/ petroleum ether (2:1), EtoAc and then EtOH. The solvent was removed, benzene was added, heated and filtered. Evaporation of the filtrate gave 99 mg of yellow solid (27) (a yield of 66%). An analytical sample recrystallized from chloroform gave mp 217° C. (dec.); IR (KBr) 3339, 1750, 1714, 1679, 1651, 1609, 1588, 1510, 1370, 1314, 1222, 1131,744, 519 cm$^{-1}$; $^1$H NMR (CDCl$_3$)*2.30 (s,3,COCH$_3$), 2.75 (s,3,ArCH$_3$), 7.55 (d,1,J=8 Hz,H—3), 7.909 (s,1,H—6), 8.29 (d,1,J=8 Hz,H—4), 8.38 (br s,1,NH); MS m/e (relative intensity) 230 (M$^-$, 69), 188 (81), 161 (100), 132 (20), 93 (15), 43 (31). Analysis calculated for C$_{12}$H$_{10}$N$_2$O$_3$: C, 62.61; H, 4.38; N, 12.17; Found: C, 62.52; H, 4.28; N, 11.93.

7-CHLOROACETAMIDO-2-METHYLQUINOLINE-5, 8-DIONE (Compound 28, Table IV): This compound was prepared by the oxidation of the corresponding acylamido with potassium dichromate in glacial acetic acid. In a 500 ml. round-bottom flask equipped with a magnetic bar, 5,7-bis(chloroacetamido)-8-hydroxy-2-methylquinoline (32) (prepared as described in Example 32) (3.42 g., 0.01 mol) was suspended in 122 ml. of glacial acetic acid. A solution of potassium dichromate (8.8 g., 0.03 mol) in 115 ml. of water was added and the resulting dark solution was stirred at room temperature overnight. The solution was extracted with dichloromethane (12×50 ml.). The organic extracts were washed with 3% sodium bicarbonate solution (200 ml.), dried with magnesium sulfate, and rotoevaporated to yield a bright yellow solid. After vacuum drying, the nearly pure product weighed 1.56 g. (yield of 59%). The product was recrystallized from ethyl acetate: mp 196–200 EC (dec.); $^1$H NMR (CDCl$_3$)*2.76 (3H, s, C—2CH$_3$), 4.23 (2H, s, C— 7NHCOC$\underline{H}_2$Cl), 7.56 (1H, d, J=8.1 Hz, C—3H), 7.89 (1H, s, C—6H), 8.30 (1H, d, J=8.1 Hz, C—4H), 9.48 (1H, br. s, C—7NH); IR (KBr) $v_{max}$ 3299, 3078, 2948, 1712, 1683, 1641, 1614, 1588, 1515, 1398, 1384, 1323, 1130 cm$^{-1}$; EIMS, m/e (relative intensity) 264/266 (M$^+$, 2.9/1, 67) 229 (62), 215 (74), 201 (43), 188 (86), 161 (base), 132 (21); HRMS, m/e for C$_{14}$H$_9$ClN$_2$O$_3$, calculated 264.030170, found 264.029824; analysis for C$_{14}$H$_9$ClN$_2$O$_3$ calculated: C, 54.46; H, 3.43; Cl, 13.40; N, 10.58; found: C, 54.19; H, 3.37; Cl, 13.29; N, 10.36.

7-BUTYRAMIDO-2-METHYLQUINOLINE-5,8-DIONE (Compound 30, Table IV): This compound was prepared by the oxidation of the corresponding acylamido with potassium dichromate in glacial acetic acid. In a 500 ml. round-bottomed flask equipped with a magnetic bar, 5,7-dibutyramido-8-butyroxy-2-methylquinoline (34) (prepared as described in Examples 31–34) (3.29 g., 8.25 mmol) was suspended in 122 ml of glacial acetic acid. A solution of potassium dichromate (8.8 g., 0.03 mol) in 115 ml. of water was added and stirred. The stirred suspension began to dissolve but, after two hours, more solid continued to precipitate. Dichloromethane (70 ml.) was added to promote solution. The resulting two-phase solution mixture was stirred at room temperature overnight. The two-phase solution mixture was extracted with dichloromethane (12× 50 ml.). The organic extracts were washed with a 3% sodium bicarbonate solution (200 ml.), dried with magnesium sulfate, and rotoevaporated to yield an orange-yellow solid. After vacuum drying, the solid weighed 1.65 g. (a yield of 77%). The product was recrystallized from ethyl acetate: mp. 188–189 EC; $^1$H NMR (CDCl$_3$)*1.00 (3H, t, J=7.4 Hz, C—7NHCOCH$_2$CH$_2$C$\underline{H}_3$), 1.69–1.82 (2H, m, C—7NHCOCH$_2$C$\underline{H}_2$CH$_3$), 2.48 (2H, t, J=7.4 Hz, C—7NHCOC$\underline{H}_2$CH$_2$CH$_3$), 2.74 (3H, s, C—2CH$_3$), 7.53 (1H, d, J=8.0 Hz, C—3H), 7.90 (1 H, s, C—6H), 8.28 (1H, d, J=8.0 Hz, C—4H), 8.36 (1H, br. s, C—7NH); IR (KBr) $v_{max}$ 3338, 3275, 2964, 2935, 2875, 1711, 1682, 1654, 1644, 1615, 1588, 1502, 1323, 1310, 1133 cm$^{-1}$; EIMS, m/e (relative intensity) 258 (81), 215 (7), 188 (base), 161 (66); HRMS, m/e for C$_{14}$H$_{14}$N$_2$O$_3$ calculated 258.100442, found 258.100227; analysis for C$_{14}$H$_{14}$N$_2$O$_3$ calculated C, 65.11; H, 5.46; N, 10.85; found C, 65.22; H, 5.51; N 10.01.

TABLE IV

| Compound | $R^{10}$ | % Yield | mp (EC) | $^1$H, NMR (CDCl$_3$) | MS | Elemental Analysis or HRMS |
|---|---|---|---|---|---|---|
| 27 | CH$_3$ | 66 | 217 | 2.30(s, 3H), 2.75(s, 3H), 7.55(d, 1H), 7.90(s, 1H), 8.29(d, 1H), 8.38(br s, 1H) | 230(M$^+$, 69), 188(81), 161(100), 132(20), 93(15), 43(31) | Calc. C, 62.61; H, 4.38; N, 12.17<br>Found C, 62.52; H, 4.28; N, 11.93 |
| 28 | ClCH$_2$ | 59 | 196–200 (dec) | 2.76(s, 3H), 4.23(s, 2H), 7.56(d, J=8.1Hz, 1H), 7.89(s, 1H), 8.30(d, J=8.1Hz, 1H), 9.48(br s, 1H) | 264/266(M$^+$2.9/1, 67), 229(62), 215(74), 201(43), 188(86), 161(base), 132(21) | C$_{14}$H$_9$ClN$_2$O$_3$<br>Calc: 264.030170<br>Found: 264.029824<br>Calc.: C, 54.46; H, 3.43; N, 10.58; Cl, 13.40 |
| 29 | (CH$_3$)$_2$CH | 73 | 189–190 (dec) | 1.26(d, J=6.76Hz, 6H), 2.7(m, J=6.76Hz, 1H), 2.75(s, 3H), 7.54(d, J=8Hz, 1H), 7.9(s, 1H), 8.29(d, J=8Hz, 1H), 8.42(br s, 1H) | 258(M$^+$, base), 215(25.9), 189(41.5), 161(266), 108(41.1) | Found: C, 54.19, H, 3.37, N, 10.36; Cl, 13.29 |
| 30 | CH$_3$(CH$_2$)$_2$ | 77 | 188–189 | 1.00(t, J=7.4Hz, 3H), 1.69–1.82(m, 2H), 2.48(t, J=7.4Hz, 2H), 2.74(s, 3H), 7.53(d, J=8.0Hz, 1H), 7.90(s, 1H), 8.28(d, J=8.0Hz, 1H), 8.36(br s, 1H) | 258(M$^+$, 81), 215(7), 188(base), 161(66) | C$_{14}$H$_{14}$N$_2$O$_3$<br>Calc 258.100442<br>Found 258.100227<br>Calc. C, 65.11; H, 5.46; N, 10.85<br>Found: C, 65.22; H, 5.51; N, 10.91 |

Examples 31–34

PREPARATION OF 5,7-DIACYLAMIDO-8-ACETOXY-2-METHYLQUINOLINES

These compounds, which were used as starting materials for the preparation of the 7-N-acyl-2-methyl-quinoline-5,8-diones of Examples 27–30, were prepared by the reduction of 5,7-dinitro-8-hydroxy-2-methylquinoline by molecular hydrogen in the presence of palladium on charcoal (Pd/C) followed by treatment with the desired anhydrides as illustrated in Equation 5 above. Table V lists four 2-methylquinolines prepared by this method, their % yields, melting points, elemental analysis, $^1$H NMR and MS. The following procedures were used to prepare these compounds. Also, the preparation of 5,7-dinitro-8-hydroxy-2-methylquinoline is described; this compound was prepared according to a literature method.

PREPARATION OF 5,7-DIACETAMIDO-2-METHYL-8-ACETOXYQUINOLINE (Compound 31, Table V): Into a 500 ml hydrogenation bottle, 5,7-dinitro-8-hydroxy-2-methylquinoline (47) (preparation described below) (6.03 g, 24.2 mmol), water (100 ml), and concentrated HCl (13 ml) Nere added. To this suspension, 5% Pd/C (2.00 g) was added as a catalyst. This mixture was hydrogenated at 40 psi overnight or until no more hydrogen is absorbed. This reaction takes approximately four hours.

The resultant solution was then carefully vacuum filtered to remove the Pd/C. Note: Do not rinse the Pd/C that is on the filter paper with water. This will dilute the solution which is concentration-sensitive. The filtrate should take up, at most, 130 ml.

The filtrate was transferred to a 500 ml beaker. To the filtrate, sodium sulfite (2.85 g), sodium acetate (3.58 g), and acetic anhydride (2.5 ml) were added with stirring using a magnetic stirrer. Generally, no precipitate formed. After 30 minutes, the same amounts of the above three compounds were added again. The addition of acetic anhydride (7.5 ml) caused an orange/white precipitate to form. Note: If no precipitate forms, remove the solvent under reduced pressure and heat until a small amount of solution is obtained. Add the three compounds (sodium sulfite, sodium acetate, and acetic anhydride) in small quantities (approximately one-quarter of that required in the procedure), and then wait 15 minutes. Next add 5 ml acetic anhydride and stir the mixture vigorously. Add small amounts of sodium sulfite and sodium acetate while vigorously stirring for 10 minutes. Stop the stirring and allow the mixture to stand, the precipitate should then form. This problem can be avoided, however, by following the prescribed procedure exactly as written. The mixture was then vacuum filtered, and the precipitate was washed three times with water (3×100 ml). This process washed the orange color out of the precipitate, and left a white solid on the filter paper. The filtrate was evaporated down to one-quarter of its volume. Any precipitate that formed was filtered and washed, as above. The filtrate was treated with sodium acetate and acetic anhydride again until no more precipitate was formed (Note: The addition of the acetic anhydride is what generally causes more precipitate to form). All washed precipitates were combined and allowed to dry overnight under the hood or on a vacuum pump. The yield was 80% (6.05 g of product, mp 255 EC).

5,7-BIS(CHLOROACETAMIDO)-8-HYDROXY-2-METHYLQUINOLINE (Compound 32, Table V): In a 500 ml heavy-walled hydrogenation bottle, 8-hydroxy-2-methyl-5,7-dinitroquinoline (47) (5.25 g., 0.021 mol) and 5% Pd/C (1.75 g.) were suspended in 90 ml. of water and 9 ml. of concentrated HCl. This mixture was shaken under 30 psi of hydrogen for 20 hours. The catalyst was filtered off, and the dark red solution containing the dihydrochloride salt of 5,7-diamino-8-hydroxy-2-methylquinoline was placed in a 250 ml. rounded-bottomed flask equipped with a magnetic bar. To this stirred solution was added in sequence as quickly as possible, sodium sulfite (12 g.), sodium acetate (16 g.), and chloroacetic anhydride (65 g.). Heat was evolved, and the formation of a light colored, thin precipitate occurred. After 15 minutes of stirring the precipitate dissolved. An additional amount of chloroacetic anhydride (5 g.) was added and the reaction mixture stirred for one hour. The solution was concentrated under reduced pressure until a precipitate appeared. This mixture was poured into a 400 ml beaker containing 100 ml. of ice-water and stirred for 5 minutes. The mixture was vacuum filtered and the product was washed with cold ethanol, dried under vacuum and collected (2.14 g.). The filtrate, upon standing overnight, yielded an additional amount of product (1.47 g.). Total weight of the product was 3.61 g. (a yield of 50%). The product was recrystallized from ethanol and water: mp 194–196° C. (dec.); $^1$H NMR (DMSO-d$_6$)*2.71 (3H, s, C—2CH$_3$), 4.37 (2H, s, COCH$_2$Cl), 4.44 (2H, s, COCH$_2$Cl), 7.43 (1H, d, J=8.8 Hz, C—3H), 8.15 (1H, d, J=8.8 Hz, C—4H), 8.16 (1H, s, C—6H), 9.89 (1H, brs, NH), 10.18 (1H, br s, NH); IR (KBr) v$_{max}$ 3392, 3361, 3262, 3005, 2950, 1680, 1660, 1646, 1557, 1523, 1508, 1456, 1416 cm$^{-1}$; EIMS, m/e (relative intensity) 341/343 (M$^+$, 1.5/1, 52), 305 (60), 292 (base), 264 (28), 250 (7), 228 (60), 214 (10), 200 (12), 188 (70), 173 (11), 160 (17); HRMS, m/e for C$_{14}$H$_{13}$Cl$_2$N$_3$O$_3$ calculated 341.033397, found 341.033888, analysis for C$_{12}$H$_{13}$Cl$_2$N$_3$O$_3$, calculated C, 49.14; H, 3.83; Cl, 20.72; N, 12.28; found, C, 49.24; H, 3.89; Cl, 20.43; N, 12.16.

5,7-DIBUTYRAMIDO-8-BUTYROXY-2-METHYLQUINOLINE (Compound 34, Table V): In a 500 ml heavy-walled hydrogenation bottle, 8-hydroxy-2-methyl-5,7-dinitroquinoline (47) (5.0 g., 0.02 mol) and 5% Pd/C (1.5 g.) were suspended in 100 ml. of water and 12 ml. of concentrated HCl. This mixture was shaken under 30 psi of hydrogen for 15 hours. The catalyst was filtered off, and the dark red solution containing the dihydrochloride salt of 5,7-diamino-8-hydroxy-2-methylquinoline was placed in a 250 ml. round-bottomed flask equipped with a magnetic bar. To this stirred solution, was added in sequence as quickly as possible, sodium sulfite (12 g.), sodium acetate (16 g.), and butyric anhydride (65 ml.). The thick whitish precipitate which continued to form over a 3-hour period was filtered and washed with water. After vacuum drying, the product weighed 7.4 9 (a yield of 93%). Since recrystallization with methanol-water resulted in the hydrolysis of the butyrate, analyses were performed on the crude product: mp. 195–205EC (dec.); $^1$H NMR (DMSO-d$_6$)*0.92 (3H, t, J=8.0 Hz, NHCOCH$_2$CH$_2$CH$_3$), 0.96 (3H, t, J=8.0 Hz, NHCOCH$_2$CH$_2$CH$_3$), 1.08 (3H, t, J=8.0 Hz, OCOCH$_2$CH$_2$CH$_3$), 1.52–1.72 (4H, m, 2 NHCOCH$_2$CH$_2$CH$_3$), 1.73–1.89 (2H, m, OCOCH$_2$CH$_2$CH$_3$), 2.30–2.40 (4H, m, 2NHCOCH$_2$CH$_2$CH$_3$), 2.58 (3H, s, C—2CH$_3$), 2.70 (2H, t, J=8.0 Hz, OCOCH$_2$CH$_2$CH$_3$), 7.37 (1H, d, J=8.8 Hz, C—3H), 8.21 (1H, d, J=8.8 Hz, C—4), 8.24 (1H, s, C—6H), 9.65 (1H, brs, C—5NH), 9.94 (1H, brs, C—7NH); IR (KBr) v$_{max}$ 3343, 3258, 2964, 2935, 2874, 1738, 1693, 1656, 1630, 1541, 1505 cm$^{-1}$.

8-HYDROXY-2-METHYL-5,7-DINITROQUINOLINE (Compound 47): Compound 47 was prepared according to the method described in Boger et al., *J. Org. Chem.*, 50, 5782 (1985). In a 500 ml. Erlenmeyer flask, equipped with a magnetic bar was placed 300 ml. of a 70% (v/v) solution of concentrated nitric acid-sulfuric acid. The solution was stirred and cooled in an ice bath. To this stirred, chilled solution, 8-hydroxy-2-methylquinoline (30.0 g., 0.188 mol) was added in small portions over a ten minute period. Upon addition of the 8-hydroxy-2-methylquinoline, a brownish gas was evolved. The mixture was continually stirred in the ice bath for two hours. The mixture was then poured into a 2 L. beaker containing 1200 ml. ice water (1:2, ice:water) and stirred vigorously with a glass rod. The bright yellow precipitate was vacuum filtered, washed with ethanol (300 ml.), and then washed with ethyl ether (2×300 ml.). The resulting 8-hydroxy-2-methyl-5,7-dinitroquinoline was left to air dry overnight and then further dried under vacuum for 24 hours. The yellow solid weighed 28.1 g. (a yield of 60%): mp. 295–300° C.; $^1$H NMR (DMSO-d6)*2.93 (3H, s, C—2CH$_3$), 8.13 (1H, d, J=9.1 Hz, C—3H), 9.20 (1H, s, C—6H), 9.65 (1H, d, J=9.1 Hz, C—4H); IR (KBr) v$_{max}$ 3067, 1593, 1527, 1336, 1320, 1299, 1259 cm$^{-1}$.

TABLE V

| Compd | R$^{10}$ | % Yield | mpN(C.) | $^1$H NMR (DMSO) | MS | Elemental Analysis or HRMS |
|---|---|---|---|---|---|---|
| 31 | CH$_3$ | 80 | 284 (dec) | 2.14(s, 3H), 2.15(s, 3H), 2.41(s, 3H), 2.60(s, 3H), 7.37(d, 1H), 8.24(d, 1H), 8.31(s, 1H), 9.75(s, 1H), 10.02(s, 1H) | | Calc. C-60.94, H-5.43, N-13.33 Found C-61.15, H-5.39, N-13.27 |
| 32 | ClCH$_2$ | 50 | 194–196 (dec) | 2.71(s, 3H), 4.37(s, 2H), 4.44(s, 2H), 7.43(d, J=8.8Hz, 1H), 8.15(d, J=8.8Hz, 1H), 8.16(s, 1H), 9.89(br s, 1H), 10.18(br s, 1H) | 341/343(M$^+$ 1.5/1, 52), 305(60), 202(base), 264(28), 250(7), 228(60), 214(10), 200(12), 188(70), 173(11), 160(17) | C$_{14}$H$_{13}$Cl$_2$N$_3$O$_3$ Calc 341.033307 Found 341.033888 |
| 33 | (CH$_3$)$_2$CH | 75 (crude) | 245–247 (dec) | 1.12(d, J=6.8Hz, 6H), 1.19(d, J=6.8Hz, 6H), 1.38(d, J=7Hz, 6H), 2.6(s, 3H), 2.84–2.72(m, 2H), 3.04–3.01(m, 1H), 7.4(d, J=8.8Hz, 1H), 8.13(s, 1H) 8.23(d, J=8.8Hz, 1H), 9.62(br s, 1H), 9.92(br s, 1H) | 399(M$^+$, 0.2), 329(base), 286(67.9), 259(39.4), 241(12.9), 188(75.2) | |
| 34 | CH$_3$(CH$_2$)$_2$ | 93 (crude) | 200–208 (dec) | 0.73(t, J=7.0Hz, 3H), 0.76(t, J=7.0Hz, 3H), 1.33–1.55(m, 4H), 2.1–2.3(m, 4H), 2.3(s, 3H), 7.17(d, J=8.8Hz, 1H), 7.82(s, 1H), 7.90(d, J=8.8Hz, 1H), 9.28(br s, 1H), 9.52(br s, 1H) | 329(95), 286(20), 259(98), 241(17), 216(6), 188(base), 161(13) | C$_{18}$H$_{23}$N$_3$O$_3$ Calc. 329.173942 Found 329.173043 |

Examples 35–46

Preparation of Tryptophan Analogs

The tryptophan analogs used for the synthesis of lavendamycin analogs 1–22 are listed in Table VI. They have formula L:

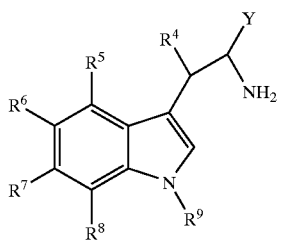

Formula L wherein $R^5$, $R^7$, $R^8$ and $R^9$ are H, and $R^4$, $R^6$ and Y are as given in Table VI below. Tryptophan esters 36, 37, and 44–46 (see Table VI) were synthesized as illustrated in Equation 6 above. Tryptophan esters 40–41 (see Table VI) were synthesized as illustrated in Equation 7 above. The procedures used for the synthesis of all of the tryptophan analogs are described below.

Tryptophan Esters 36, 37 and 44–46 (Table VI): Tryptophan (or $^b$-methyltryptophan) (3 g, 0.015 mol) and dry HCl-saturated isoamyl alcohol (or other alcohols) (180 ml) were stirred and refluxed for 24 hr. The reaction mixture was rotoevaporated to give a white crystal salt. After it was washed with ether, the salt was neutralized with 14% NH$_4$OH in 25 ml ethyl acetate. Then, it was washed with water and dried with anhydrous magnesium sulfate. Finally, it was rotoevaporated to give 33.21 g colorless oil (or crystal) (yield 80–90%).

Tryptophan Esters 40 and 41 (Table VI):

(1) Carbobenzoxy-tryptophan (or Carbobenzoxy-$^b$-Methyltryptophan): A mixture of tryptophan (4.1 g, 0.02 mol) (or $^b$-methyltryptophan), NaOH (2N, 10 ml), water (20 ml), benzylchloroformate (3.4 g., 0.02 mol, in 2.2 ml of toluene) was stirred in an ice bath. Another 5 ml of NaOH (4N) was added dropwise over 20 minutes and stirred for an additional 10 minutes. The mixture was acidified to Congo Red with hydrochloric acid, filtered, washed with cold water and dried to give 5.86 g. product (yield 87%). N-CBZ-$^b$-methyltryptophan was produced in a yield of 93%.

(2) N-CBZ-Tryptophan (or N-CBZ-$^b$-Methyltryptophan) N,N-Dimethylethylamino Ethyl Ester: N-CBZ-tryptophan (3.384 g., 0.01 mol) (or N-CBZ-$^b$-methyltryptophan), N,N-dimethylaminoethylchloride (2.1 N benzene solution, 6 ml), ethyl acetate (20 ml) was stirred and heated. Triethylamine (1.4 ml) was added dropwise, and the mixture was then refluxed 5 hr. and filtered. The filtrate was washed with saturated NaCl in water, 5% NaHCO$_3$ and saturated NaCl in water, dried with anhydrous MgSO$_4$, rotoevaporated to give 1.76 g. of a spongy gel (a yield of 43%). N-CBZ-$^b$-methyltryptophan-N,N-dimethylethylaminoethyl ester was produced in a yield of 81%.

(3) Tryptophan (or $^b$-Methyltryptophan) N,N-Dimethylethylamino Ethyl Ester: A mixture of ammonium formate (125 mg) and N-CBZ-tryptophan-N,N-dimethylethylaminoethyl ester (205 mg, 0.5 mmol) (or N-CBZ-$^b$-methyltryptophan-N,N-dimethylethylaminoethyl ester), DMF (5 ml), 10% Pd/C (100 mg) was stirred under argon at room temperature for 30 minutes and then filtered. The filtrate was rotoevaporated to an oil. Chloroform (10 ml) was added to the oil and filtered again. The filtrate was rotoevaporated to dryness and dissolved in ethyl acetate (25 ml), washed with 3×5 ml saturated NaCl solution, dried over anhydrous MgSO$_4$, evaporated in a vacuum to give 101 mg of the oily product (a yield of 74%). $^b$-methyltryptophan N,N-dimethylethylamino ethyl ester was produced in a yield of 68%.

Tryptophan Analogs 35, 38, 42 and 43 (Table VI): These compounds are commercially available as the hydrochloride salts. They were converted to the free amines by neutralization with 14% ammonium hydroxide, followed by extraction with ethyl acetate.

Tryptophan Ester 39 (Table VI): This compound was made as described in Behforouz et al., *J. Heterocycl. Chem.*, 25, 1627 (1988).

TABLE VI

| Compound | $R^4$ | $R^6$ | Y |
|---|---|---|---|
| 35 | H | H | $CO_2CH_3$ |
| 36 | $CH_3$ | H | $CO_2CH_2CH_2CH(CH_3)_2$ |
| 37 | H | H | $CO_2CH_2CH_2CH(CH_3)_2$ |
| 38 | H | H | $CO_2(CH_2)_7CH_3$ |
| 39 | $CH_3$ | H | $CO_2CH_3$ |
| 40 | H | H | $CO_2CH_2CH_2N(CH_3)_2$ |
| 41 | $CH_3$ | H | $CO_2CH_2CH_2N(CH_3)_2$ |
| 42 | H | H | $CO_2(CH_2)_3CH_3$ |
| 43 | H | H | $CO_2NH_2$ $CH_2$—$CH_2$ |
| 44 | H | H | $CO_2CH$   $CH_2$ $CH_2$—$CH_2$ |
| 45 | H | $OCH_3$ | $CO_2(CH_2)_3CH_3$ |
| 46 | H | F | $CO_2(CH_2)_3CH_3$ |

Example 47

In Vitro Cytotoxicity

The in vitro cytotoxicity of some of the lavendamycin analogs was determined according to the methods described below against a panel of five cell types. A few quinoline diones were also tested for cytotoxicity.

A. Cell Lines and Culture Conditions. Stock cultures of normal rat kidney epithelial (NRKE) cells [De Larco et al., *J. Cell Physiol.*, 94, 335 (1978)] and Lewis lung carcinoma cells [Suguira et al., *Cancer (Phila.)*, 5, 382 (1952)] were obtained from the American Type Culture Collection (ATCC, Rockville, Md.). Both cell lines were grown in antibiotic-free culture medium [Dulbecco's high glucose MEM supplemented with 10% fetal bovine serum]. The cell number of the Lewis lung and NRKE cell lines was expanded by 5 passages, and the cell lines were stored in liquid nitrogen, all according to standard procedures [Freshney, *Culture of Animal Cells: A Manual of Basic Technique*, pages 6, 216–225 (2nd ed. 1987)]. These cryopreserved cells were used for the assays described below. All cell lines were grown using standard cell culture methods. [Freshney, *Culture Of Animal Cells: A Manual Of Basic Technique*, page 127 (2nd ed. 1987)] All cell culture manipulations were done under gold fluorescent light to prevent damage by photooxidation.

B. Selection of Transformed Cells and Oncogene Transfections. NRKE cells transformed by the ras$^K$, ras$^N$, and ras$^H$ oncogenes were used in the panel. Only transformants with a minimal deviation phenotype as compared to NRKE cells were used. Transformants with this phenotype have a low oncogene copy number and in vitro growth characteristics the same as nontransformed NRKE cells. These criteria were chosen so that compounds were evaluated for antitumor activity, rather than anti-growth activity based on the rate of cell division.

The ras oncogene-transformed NRKE cells were prepared as follows. The plasmids pUCEJ6.6 (no. 41028), containing a transforming human $ras^H$ gene, pNRsac (no. 41031) containing a transforming human $ras^N$ gene, pKSma (no. 41048), containing a v-$ras^K$ gene, and the RSVneo gene were obtained from the ATCC. NRKE cells were cotransfected with an oncogene plus the RSVneo gene using standard calcium phosphate coprecipitation and neomycin resistance selection methods. [Davis et al., *Basic Methods In Molecular Biology*, 285 (1985)]. Approximately 14 days after transfection and selection with G-418 antibiotic (Sigma Chemical Co., St. Louis, Mo.), colonies were isolated by the ring cloning procedure. [Freshney, *Culture Of Animal Cells: A Manual Of Basic Technique* (2nd ed. 1987)]. The clones were stored in liquid nitrogen after expansion of their cell number by 4 passages in culture medium with G-418. Approximately 50 clones were evaluated by several criteria for their use in the in vitro cytotoxicity and in vivo antitumor tests described below. The criteria used to select clones were the following: (1) the clone had to have the same growth rate as the parental NRKE cells, (2) the growth rate of the clone must be stable with repeated passage (e.g., up to 100 subcultures), and (3) they must be tumorigenic in immunologically deficient mice. Criteria 1 and 2 are key to assuring the differential cytotoxicity assay selects for compounds that have antitumor activity rather than a general anti-growth activity. Oncogene copy number was determined using standard Southern blotting procedures [*Current Protocols in Molecular Biology*, Chapter 2, Frederick M. Ausuhel et al. eds., 1987–1992]. Cell growth characteristics were evaluated using standard methods (Freshney, *Culture of Animal Cells: A Manual of Basic Technique*, pages 227–244 (2nd ed., 1987)].

The clones K/1-NRKE, transformed by v-$ras^K$ gene, H/1.2-NRKE, transformed by the human $ras^H$ gene, and N/4.2-NRKE transformed by the human $ras^N$ gene, were selected for in vitro cytotoxicity and in vivo antitumor testing. These clones have 3 to 4 oncogene copies that are stably integrated. The in vitro doubling time of these cells is 24 hours, which is the same as NRKE cells.

C. In Vitro Cytotoxicity Assay. Compounds were screened for antitumor activity with an oncogene-based differential cytotoxicity assay. With this assay the cytotoxic action of compounds against oncogene-transformed cells relative to their action against the nontransformed parent epithelial cells was determined. For the evaluation of compounds, the Lewis lung carcinoma was used as a murine reference tumor. This tumor is commonly used in screens for new oncolytics. The differential cytotoxicity assay can identify compounds that interact directly with oncogene proteins, but more importantly it can also find compounds that interfere with the biochemical pathways activated or driven by oncogenes. The inhibitory action in both cases may be specific for a transformed cell.

Briefly, the procedure used for the differential cytotoxicity assay is as follows. Cell suspensions were prepared by trypsin dissociation using standard methods [Freshney, *Culture Of Animal Cells: A Manual Of Basic Technique*, page 132], and 50 cells were seeded into each well of 12-well culture dishes. Groups of triplicate wells were divided into media control, drug vehicle-control and drug treatment groups. One day after seeding, media was replaced with media containing vehicle or drugs, and the cultures were incubated for an additional 5 days.

After exposure to the vehicles or drugs, the cultures were washed, fixed and stained with a modification of Mallory's stain. [Richardson et al., *Stain Technol.*, 35, 313 (1960)]. Colony number and colony area were determined with an Artek model 982 image analyzer (Artek System Corp., Farmington, N.Y.). The cytocidal action of compounds was determined from the colony number as originally described by Puck and Marcus, *J. Exp. Med.*, 103, 653 (1956). Colony areas were normalized for colony number and were used to determine if a compound had a cytostatic action. The concentration giving 50% cell kill ($LC_{50}$) was determined, and a differential index of cytotoxicity was determined by dividing the $LC_{50}$ value for the normal epithelial cells by the $LC_{50}$ value for the tumor cells. The differential index value was used to determine the amount of selective toxicity a compound had for the tumor cells. All data analysis was performed using SAS software [*SAS Users Guide: Statistics* (Version 5 edition, SAS Institute Inc., Cary, N.C. 1985)] on a VAX 8300 computer. The results are shown in Tables VII, VIII and IX.

TABLE VII

| | $LC_{50}$ (:M) | | | |
|---|---|---|---|---|
| Compound | NRKE | K/1 | H/1.2 | 3LL |
| 27; $R^{15}$=NHAc $R^1$, $R^3$=H, $R^{16}$=CH$_3$ | 2.4 | 5.9 | 4.4 | 2.0 |
| 23; $R^{15}$=NHAc $R^1$, $R^3$=H, $R^{16}$=CHO | 1.3 | 2.6 | 2.5 | 1.2 |
| 48; $R^{15}$=NHAc $R^1$, $R^3$=H, $R^{16}$=COOH | >33 | >33 | 31 | 26 |
| 49; $R^{15}$=NHAc $R^1$=H, $R^3$=CH$_3$, $R^{16}$=H | 1.3 | 1.8 | 1.1 | 1 |
| 50; $R^{15}$=NH$_2$ $R^1$=H, $R^3$=CH$_3$, $R^{16}$=H | 0.8 | 1.3 | 0.6 | 0.8 |
| 51; $R^{15}$=NH$_2$ $R^1$, $R^3$=H, $R^{16}$=CHO | 2.4 | 4.3 | 2.2 | 2.3 |
| 52; $R^{15}$=H, $R^1$=NHAc, $R^3$=H, $R^{16}$=CH$_3$ | 21.5 | >33 | 20 | >33 |
| 53; $R^{15}$=OCH$_3$, $R^1$, $R^3$=H, $R^{16}$=CH$_3$ | 6.9 | 11.8 | 4.2 | 7.4 |
| 54; $R^{15}$=O(CH$_2$)$_4$OH, $R^1$, $R^3$=H, $R^{16}$=CH$_3$ | 10.5 | 13.5 | 10.5 | 3.8 |
| 1; $R^{15}$=NHAc, $R^1$, $R^3$=H, $R^{16}$=BC | 0.9 | 0.1 | 0.7 | >33 |
| 55; $R^{15}$=NH$_1$, $R^1$, $R^3$=H, $R^{16}$=BC | 0.1 | 0.2 | 0.1 | 0.5 |

NRKE = Normal Rat Kidney Epithelial Cells.
K/1 = $ras^K$ Transformed NRKE Cells.
H/1.2 = $ras^H$ Transformed NRKE Cells.
3LL = Lewis Lung Carcinoma Cells.

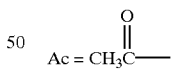

Ac = CH$_3$C—

CC = $^b$-carboline moiety having the formula:

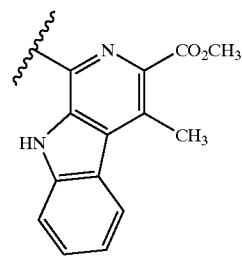

In Table VII, the compounds tested have the following formula:

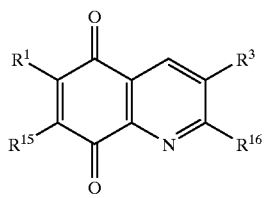

Compounds 1, 23 and 27 were prepared as described in Examples 1, 23 and 27. Compounds 49 and 52 were prepared according to Equation 2. Compound 48 was obtained by the oxidation of 23. Treatment of 27 with methanol in the presence of acid gave 53, and treatment of 27 with tetrahydrofuran in the presence of acid gave 54. Compounds 50, 51 and 55 were obtained by the acid hydrolysis of 49, 23 and 1 respectively.

In Table VIII and IX, the compounds tested have the following formula:

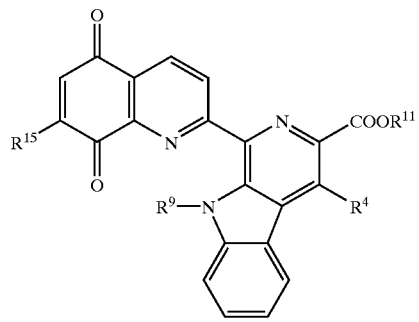

TABLE VIII

| Compound | Substituent | | | LC50 (:M) | | | | |
|---|---|---|---|---|---|---|---|---|
| | $R^{15}$ | $R^{11}$ | $R^4$ | NRKE | H/1.2 | K/1 | N/4.2 | 3LL |
| 1 | NHAc | $CH_3$ | $CH_3$ | 0.90 | 0.70 | 0.10 | N.T. | <33.00 |
| 17 | NHAc | $CH_3$ | H | 0.50 | 0.51 | 0.11 | 0.52 | 0.84 |
| 18 | NHAc | $CH_2CH_2CH(CH_3)_2$ | $CH_3$ | 4.61 | 4.30 | 5.00 | 3.89 | 7.40 |
| 19 | NHAc | $CH_2CH_2N(CH_3)_2$ | $CH_3$ | 0.09 | 0.09 | 0.06 | 0.09 | 0.48 |
| 20 | NHAc | $CH_2CH_2CH(CH_3)_2$ | H | 1.62 | 1.42 | 0.09 | 1.50 | 1.69 |
| 21 | NHAc | $(CH_2)_7CH_3$ | H | >33.00 | 7.60 | 0.25 | 9.00 | <33.00 |
| 22 | NHAc | $CH_2CH_2N(CH_3)_2$ | H | 0.37 | 0.24 | 0.14 | 0.29 | 0.50 |
| 55 | $NH_2$ | $CH_3$ | $CH_3$ | 0.1 | 0.1 | 0.2 | N.T. | 0.5 |

TABLE IX

| Compound | Substituent | | | Differential Index | | | |
|---|---|---|---|---|---|---|---|
| | $R^{15}$ | $R^{11}$ | $R^4$ | H/1.2 | K/1 | N/4.2 | 3LL |
| 1 | NHAc | $CH_3$ | $CH_3$ | 1.29 | 9.00 | — | >0.03 |
| 17 | NHAc | $CH_3$ | H | 0.98 | 4.55 | 0.96 | 0.59 |
| 18 | NHAc | $CH_2CH_2CH(CH_3)_2$ | $CH_3$ | 1.07 | 0.92 | 1.19 | 0.62 |
| 19 | NHAc | $CH_2CH_2N(CH_3)_2$ | $CH_3$ | 1.00 | 1.50 | 1.00 | 0.19 |
| 20 | NHAc | $CH_2CH_2CH(CH_3)_2$ | H | 0.62 | 18.00 | 1.08 | 0.96 |
| 21 | NHAc | $(CH_2)_7CH_3$ | H | >4.3 | >132.00 | >3.66 | >1.00 |
| 22 | NHAc | $CH_2CH_2N(CH_3)_2$ | H | 1.54 | 2.64 | 1.28 | 0.74 |
| 55 | $NH_2$ | $CH_3$ | $CH_3$ | 1.0 | 0.50 | — | 0.20 |

N.T. = Not tested
N/4.2 = ras$^N$ transformed NRK cells
See Table VII for NRK K/1, H/1.2, 3 LL and Ac As shown in Table VIII, the lavendamycin analogs 1 and 17–22 were all toxic to one or more of the tumor cells tested. The lavendamycin analogs also generally showed selective cytotoxicity against the ras$^K$ oncogene bearing cells (see Tables VIII and IX). In particular, lavendamycin analogs 1, 20, and 21 showed unprecedented highly selective toxicity (9-, 18-, and 132-fold, respectively) against ras$^K$ oncogene bearing tumor cells as compared to the normal, non-transformed cells. By comparison, the prior art compound lavendamycin methyl ester 55 has a selective toxicity of 0.5 (Table IX).

Example 48

In Vivo Activity Against Tumors

The antitumor activity of N-acetyl-lavendamycin methyl ester (1), N-acetyldemethyllavendamycin isoamyl and n-octyl esters (20 and 21) and cyclophosphamide (CY) (reference) were evaluated against K/1-NRKE tumor (ras$^K$-transformed NRKE cells) grown as a xenograft in nude mice.

1. The Mice

Female CDI nu/nu nude and female C57B1/6 mice were obtained from Charles Rivers, Inc. Animals were housed in plastic shoebox type cages covered with a microisolator top. All animal feed, water, bedding and cages were sterilized. The animals were provided water (pH 3.0) and Purina mouse diet ad libitum. All animal manipulations were done with sterile procedures in a 100% exhaust, vertical laminar flow, HEPA filtered hood. To maintain consistent tumor growth, only mice between 4 and 6 weeks of age were used.

2. Tumor Implantation and Measurement

Transformed cells obtained by oncogene transfection of NRKE cells as described in Example 47 above were grown as xenograft tumors in the female CD1 nu/nu mice. Transformed cells grown in vitro through passage 7 were used to establish the xenografts. The Lewis lung carcinoma was grown as a syngeneic tumor in C57B1/6 mice as described previously in Merriman et al., *Cancer Research,* 49, 4509–4516 (1989). Tumors were initiated by the subcutaneous implantation of $1\times10^6$ cells approximately 1 cm from the first mammary gland. After implantation, the mice were randomized and divided into treatment groups of 10 mice per group. Starting one day after tumor implantation, the mice were dosed IP with drug daily for 8 days as described in the next section. On day 10, tumor mass was determined as described by Tomayko and Reynolds, *Cancer Chemother. Pharmacol.,* 24, 148–154 (1989) with the following ellipsoid volume equation:

Mg tumor=1/2 (length×width×height)

Percent inhibition of tumor growth was calculated from the ratio of the tumor mass for the drug treated animals relative to the mass for the vehicle treated animals. All animals were weighed at the beginning and end of treatment to determine if inhibition of tumor growth was due to weight loss.

Adenocarcinomas are produced in female CDI nu/nu nude mice approximately 3 days after the subcutaneous implantation of $1\times10^6$ cells. These tumors grow with a doubling time of 24 hours. In contrast, no tumors are produced in nude mice up to one year after the subcutaneous implantation of $10^8$ parent NRKE cells.

3. Drug Treatment

CY was dissolved in isotonic saline, 20 and 21 were dissolved in corn oil, and 1 was dissolved in 10 percent emulphor 620 in Dulbecco's phosphate buffered saline. It should be noted that 1 was poorly soluble in this vehicle. Starting 1 day after tumor implantation, drugs were administered interperitoneally (IP) at the doses given in Table X. CY and compounds 20 and 21 were given once daily for 8 days. Compound 1 was administered in three doses per day at lower dose levels, and the animals were treated for 7 days. On day 10, tumor masses, percent inhibition of tumor growth, and weight changes were determined.

4. Results

The results, presented in Table X, show that the three lavendamycin analogs 1, 20 and 21 gave excellent tumor growth inhibition in vivo. Other investigators have found that a dose of 100 mg/kg/day of lavendamycin and related compounds is lethal, but compounds 1, 20 and 21 showed little or no toxicity even at doses up to 300 mg/kg/day. The weight loss induced by compound 20 may be due to the presence of the isoamyl group, and replacement of this group by groups having an even number of carbons may reduce the slight toxicity. Since compounds 1 and 21 showed no toxicity, use of higher dose levels may increase the inhibition of tumor growth with little or no toxicity.

TABLE X

| Compound | Dose (Mg/Kg/Day) | Number Dead Number Treated | Percent Wt. Change (g) | Percent Inhibition Of Tumor Growth |
| --- | --- | --- | --- | --- |
| 20 | 150 | 0/7 | −11.5 " 0.05 | 88 " 5 |
|  | 300 | 0/7 | −15.7 " 0.08 | 89 " 12 |
| 21 | 150 | 0/7 | +2.0 " 0.12 | 34 " 16 |

TABLE X-continued

| Compound | Dose (Mg/Kg/Day) | Number Dead Number Treated | Percent Wt. Change (g) | Percent Inhibition Of Tumor Growth |
| --- | --- | --- | --- | --- |
|  | 300 | 0/7 | −1.0 " 0.05 | 78 " 13 |
| CY | 60 | 0/7 | −3.0 " 0.09 | 97 " 2 |
| 1 | 10 | 0/7 | +8.4 " 0.68 | 10 " 14 |
|  | 30 | 0/7 | +9 " 0.54 | 26 " 18 |
|  | 100 | 0/7 | +2.5 " 1.70 | 69 " 5 |

Example 49

National Cancer Institute Testing

The following compounds were submitted for testing in the National Cancer Institute's (NCI's) cancer drug discovery and development program: 1, 2, 16, 20, 21, 26, 30, 55, 7-N-formyldemethyllavendamycin octyl ester (56), demethyllavendamycin octyl ester (57), and 6-Chlorolavendamycin methyl ester (58). The preparation and structures of compounds 1, 2, 16, 20, 21, 26 and 30 are provided in Examples 1, 2, 16, 20, 21, 26 and 30, The preparation and structure of compound 55 is provided in Example 47. The preparation and structure of compound 58 is provided in Example 52.

Compound 56 and the intermediate compounds in its preparation were prepared as described above. In the final step, 34.2 mg (0.148 mmole) of 2-formyl-7-formamyl quinoline-5,8-dione and 48.02 mg (0.152 mmole) of tryptophan octyl ester were mixed in a three-neck round bottom flask equipped with reflux apparatus and a magnetic stirrer. The flask was heated in an oil bath; the oil bath temperature was raised from room temperature to 127° C. over three hours and then was maintained at 127° C. for 32 hours. The reaction was stopped after 32 hours, and the solution was hot filtered. A brown-yellow solid was obtained. $H^1$NMR was performed with the result of *0.88 (t, 3H), *1.3 (m, 1 OH), *1.9 (m, 2H), *4.8 (t, 2H), *7.66 (t, 1H), *7.70 (t, 1H), *7.74 (d, 1H), *7.98 (s, 1H), *8.24 (d, 1H), *8.53 (s, 1H), *8.55 (s, 1H), *8.75 (s, 1H), *8.95 (s, 1H), *9.21 (s, 1H), *11.75 (s, 1H).

Compound 57 is identical to 56, except that it has —$NH_2$ at position 7 instead of —NHCOH. It was prepared by acid hydrolysis of 56.

The NCI's cancer drug discovery and development program is described in Grever et al., *Seminars in Oncology,* 19, 622–38 (1992). Compounds chosen for the program are initially tested in an in vitro anticancer screen. A total of fifty-five human tumor cell lines, derived from nine cancer types (lung, colon, melanoma, renal, ovarian, brain, prostate, breast and leukemia), are used in this screen. The tumor cells are inoculated over a series of standard 96-well microtiter plates on day 0. These cells are then preincubated on the microtiter plates for 24 hours. The test compounds are added to the wells in five 10-fold dilutions starting from the highest soluble concentration. Each compound is tested against every cell line in the panel. The compounds are incubated for 48 hours with the tumor cell lines. At the termination of the assay, the cells are fixed in situ, washed, and dried. Sulforhodamine B (SRB), a pink anionic dye that binds to the basic amino acids of trichloroacetic acid-fixed cells, is added. The cells are washed again, and the remaining dye is a function of the adherent cell mass. The bound stain is solubilized and measured spectrophotometrically. The data are entered from automatic reading devices into a computer for subsequent storage and analysis.

The measured effect of each test compound on the cell lines is calculated according to one or the other of the following two expressions:

If (Mean $OD_{test}$−Mean $OD_{tzero}$)≥0, then PG=100×(Mean $OD_{test}$−Mean $OD_{tzero}$)/(Mean $OD_{ctrl}$−Mean $OD_{tzero}$);

or

If (Mean $OD_{test}$−Mean $OD_{tzero}$)<0, then PG=100×(Mean $OD_{test}$−Mean $OD_{tzero}$)/Mean$_{tzero}$;

Where:

PG=percent growth.

Mean $OD_{tzero}$=The average of optical density measurements of SRB-derived color just before exposure of cells to the test compound.

Mean $OD_{test}$=The average of optical density measurements of SRB-derived color after 48 hours exposure of cells to the test compound.

Mean $OD_{ctrl}$=The average of optical density measurements of SRB-derived color after 48 hours with no exposure of cells to the test compound.

The NCI provides the following information about the results of the cancer screen for each test compound. First, a data sheet is provided which lists, for each cell line, the Mean $OD_{tzero}$, the Mean $OD_{ctrl}$, the Mean $OD_{test}$ for each of the five concentrations, the calculated PGs for each concentration, and the response parameters GI50, TGI, and LC50. GI50, TGI, and LC50 are interpolated values representing the concentrations at which the PG is +50, 0, and −50, respectively.

Second, dose-response curves are provided. These curves are created by plotting the PGs against the $\log_{10}$ of the corresponding concentration for each cell line. Horizontal lines are provided at the PG values of +50, 0, and −50. The concentrations corresponding to points where the curves cross these lines are the GI50, TGI, and LC50, respectively.

Third, mean graphs at each of the principal response parameters (GI50, TGI, and LC50) are provided. Bars extending to the right of a vertical line representing the mean for each of these parameters shows sensitivity of the cell line to the test agent in excess of the average sensitivity of all tested cell lines. Since the bar scale is logarithmic, a bar two units to the right implies the compound achieved the response parameter (e.g., GI50) for the cell line at a concentration 1/100 the mean concentration required over all cell lines, and thus the cell line is unusually sensitive to that compound. Bars extending to the left correspondingly imply sensitivity less than the mean. Thus, the mean graphs facilitate visual scanning of data for potential patterns of selectivity for particular cell lines or for particular subpanels with respect to a selected response parameter.

Finally a dose-response matrix is provided for each test compound. It combines some qualities of the dose-response curve with some qualities of the mean graph. Selective effects at the cell line or subpanel levels are visualized as in the mean graph, however, different levels of effect are also depicted simultaneously, as in dose response curves.

The values of $D_{GI50}$, $D_{TGI}$, and $D_{LC50}$ displayed near the bottom of the dose-response matrix are measures of subpanel selectivity based on the response parameters GI50, TGI, and LC50. These values identify whether subpanel-selective effects occur at a high (LC50 or TGI) or moderate (GI50) effect level. Computer simulations suggest that a value of $D_{GI50}$, $D_{TGI}$ or $D_{LC50}$≥50 is statistically significant. To calculate $D_{GI50}$, the percentage of cell lines that achieve GI50 for each subpanel is calculated separately for each concentration. Then three differences are calculated separately for each of the 5 concentrations: (1) the highest subpanel percentage minus the percentage of the remaining cell lines, (2) the percentage for the 2 highest subpanels, taken together, minus the percentage for the remaining cell lines, and (3) the average of the 3 highest subpanel percentages minus the percentage for the remaining cell lines, $D_{GI50}$ is the largest of these 15 differences. The values $D_{TGI}$ and $D_{LC50}$ are the analogous maximum differences relating to TGI and LC50.

The value of $D_H$ at the bottom of the dose-response matrix provides a more general measure of selective effect. The $D_H$ value is given primarily as a means of assigning relative scores of selectivity to the compounds, and the practical significance of this value will be determined empirically. However, computer simulations suggest that values of $D_H$≥75 are statistically significant. To calculate DH, each cell line is ranked 1 to N (where N is the total number of cell line tests which satisfy quality control criteria) from least to most sensitive, by PG value. This is done separately for each concentration. At each concentration, a mean rank is calculated for each subpanel by averaging the individual cell line ranks, and the subpanels are ordered by sensitivity as measured by mean rank. At each of the 5 concentrations, the 3 mean rank differences are calculated: the mean rank for the k (where k=1, 2, 3) most sensitive subpanels, taken together, minus the mean rank of the remaining cell lines. $D_H$ is the largest of these 15 differences, multiplied by 200/N, so that its range is 0–100.

The maximum of $D_{GI50}$, $D_{TGI}$ and $D_{LC50}$ is used to determine whether subpanel-selective cytotoxicity is occurring most markedly at the GI50, the TGI, or the LC50 level, and thus to determine which of the three corresponding mean graphs to display on the dose-response matrix. The $MGD_H$ value is a measure of subpanel selectivity similar to $D_H$, but relating to this chosen mean graph. Each cell line is ranked, from least to most sensitive, by the mean graph bar extension. $MGD_H$ is the maximum difference in mean rank between the most and least sensitive subpanels, which are maximized over the choice of 1, 2, or 3 subpanels to be the most sensitive, and multiply by 200/N, just as in the calculation of $D_H$. The $MGD_H$ value is given primarily as a means of assigning relative scores to the mean graphs of the compounds. However, computer simulations indicate that values exceeding 75 are statistically significant.

Numerous patterns of cellular responsiveness are generated by the many substances that are tested in the NCI cancer screen. Grever et al., *Seminars in Oncology*, 19, 622–38 (1992) reports that application of computerized programs and neural network analysis of the primary in vitro screening data have provided evidence that it is identifying compounds with some biological relevance.

From the above discussion, it can be seen that the data provided by the NCI for each compound is substantial and complicated. Consequently, no attempt will be made here to present all of the data for the ten compounds submitted to the NCI for testing. Instead, Table XI below provides a summary of the activity of each of the ten compounds against the nine types of cancer. Also, Table XII lists those compounds which showed selectivity toward particular types of cancer.

In particular, compounds 16 and 55 exhibited unexpected selectivity for renal cancer and non-small cell lung cancer, respectively. The complete package of data received from the NCI and more information about the calculation and interpretation of the data will be filed as part of an information disclosure statement during the prosecution of this application.

Compound 55 does not come within the scope of the formulas of the claimed compounds of the invention. However, it may be utilized to treat cancer in the same manner described above for the claimed compounds, i.e., it may be made into suitable pharmaceutical compositions,

TABLE XI

| | Activity (Average PG for highest dose tested)* | | | | | | | | |
|---|---|---|---|---|---|---|---|---|---|
| Compound | Leukemia | Non-Small Cell Lung Cancer | Colon Cancer | CNS Cancer | Melanoma | Ovarian Cancer | Renal Cancer | Prostate Cancer | Breast Cancer |
| 1 | +36.3 | +42.6 | +80.0 | +60.2 | +80.3 | +70.0 | +63.0 | +89.5 | +47.9 |
| 2 | −34.7 | −27.9 | −43.6 | −26.6 | −53.7 | −62.7 | −74.6 | −45.5 | −32.6 |
| 16 | −28.3 | −52.3 | −52.1 | −60.4 | −78.4 | −55.5 | −72.9 | −18.0 | −45.1 |
| 20 | −4.0 | −19.1 | −53.0 | −49.5 | −75.2 | −42.2 | −56.1 | −70.5 | −38.6 |
| 21 | +20.3 | +13.0 | +62.3 | +59.3 | +58.6 | +47.0 | +67.5 | +69.5 | +62.9 |
| 26 | −10.8 | −50.9 | −17.9 | −61.0 | −79.0 | −63.2 | −93.0 | −81.5 | −35.0 |
| 30 | −21.7 | −71.1 | −66.6 | −93.8 | −85.1 | −86.7 | −92.0 | −79.0 | −62.7 |
| 55 | +30.0 | −60.8 | −20.0 | −39.3 | −53.0 | −43.5 | −63.8 | −31.0 | −43.8 |
| 56 | −29.7 | −28.8 | −30.0 | −36.8 | −39.9 | −57.3 | −51.3 | +14.0 | −42.3 |
| 57 | +90.8 | +89.8 | +100.3 | +81.0 | +89.4 | +89.3 | +68.7 | +94.5 | +96.0 |
| 58 | −14.6 | −69.3 | −84.9 | −52.2 | −86.1 | −39.3 | −73.7 | −63.0 | −58.7 |

*See above for calculation of PG. The average PG was calculated by summing the PGs for individual cell lines and dividing the sum by the number of cell lines. A PG below +100% indicates activity.

TABLE XII

| Compound | Selectivity |
|---|---|
| 16 | One of the seven renal cancer cell lines was about 100 times more sensitive to compound 16 than the average sensitivity of the fifty-five cell lines at one or more dose levels (i.e., at GI50, TGI and/or LC50).* |
| 55 | One of the seven non-small cell lung cancer cell lines was about 100 times more sensitive to compound 55 than the average sensitivity of the fifty-five cell lines at one or more dose levels (i.e., at GI50, TGI and/or LC50).* |

*A bar two units to the right of the mean line on the mean graphs indicates this level of sensitivity (see above).

As part of the NCI's cancer drug discovery and development program, certain compounds shown to have antitumor activity in the cancer screen are referred to the Biological Evaluation Committee for Cancer Drugs (BEC/Cancer) for secondary in vitro and in vivo investigations that are critically important to determining whether they have the potential for becoming actual anticancer drugs. The BEC/Cancer reviews the in vitro antitumor data, determines the further secondary testing that is required, and initiates the in vivo evaluations to assess the therapeutic index (i.e., an assessment of the antitumor effects in conjunction with the observed toxic effects).

As a result of its performance in an initial and a repeat cancer screen, compound 55 has been selected for in vivo testing. Compound 55 was chosen primarily because of its selectivity for non-small cell lung cancer. To date, toxicity studies have been performed, and the maximum tolerated dose in mice has been determined to be 400 mg/kg.

Also, compounds 2, 16, 26 and 30, which were submitted to the NCI much later than compound 55, were selected for repeat testing in the cancer screen. As a result of this repeat cancer screen, compounds 16, 26 and 30 are being considered by the BEC for in vivo testing. It should be noted that in the repeat screen compound 16 did not exhibit the selectivity for renal cancer seen in the initial screen and compound 30 showed selectivity for leukemia.

may be administered, and effective dosages may be determined, all as described above for the claimed compounds.

Example 50

Activity Against Leshmania

Leishmania are parasitic protozoa (family Trypanosomatidae) which are the causal agents of leishmaniasis in mammals. Three 7-N-acetyllavendamycin esters were tested for activity against *Leishmania major*. The three compounds tested were 1, 20 and 21 (for preparation and structure of these compounds, see Examples 1, 20 and 21).

An in vitro assay was performed as follows. *L. major* promastigotes were incubated at $1 \times 10^6$ promastigotes per ml in 5 ml of culture medium (medium 199 containing 20% heat-inactivated fetal bovine serum) for three days at 26 EC in the presence of 0.5 to 10.0 FM of compound 1, 20 or 21 or of pentamidine isethionate (1,5-bis[p-amidinophenoxyl]-pentane bis[2-hydroxyethane sulfonate]; Sigma, product number P0547). Pentamidine isethionate is a widely used anti-leishmanial therapeutic drug. The drugs were initially solubilized in alcohol, DMSO or saline and then diluted in fresh culture medium to the desired concentration. Control cultures received diluent only.

After the three days of culture, viable parasites were counted on a hemocytometer using a light microscope. Multiple counts of duplicate wells were made. The results are presented in FIG. 1A. The percent survival was calculated as:

$$\frac{\text{Number of cells in culture with drug}}{\text{Number of cells in culture without drug}} \times 100$$

Figure 1B:
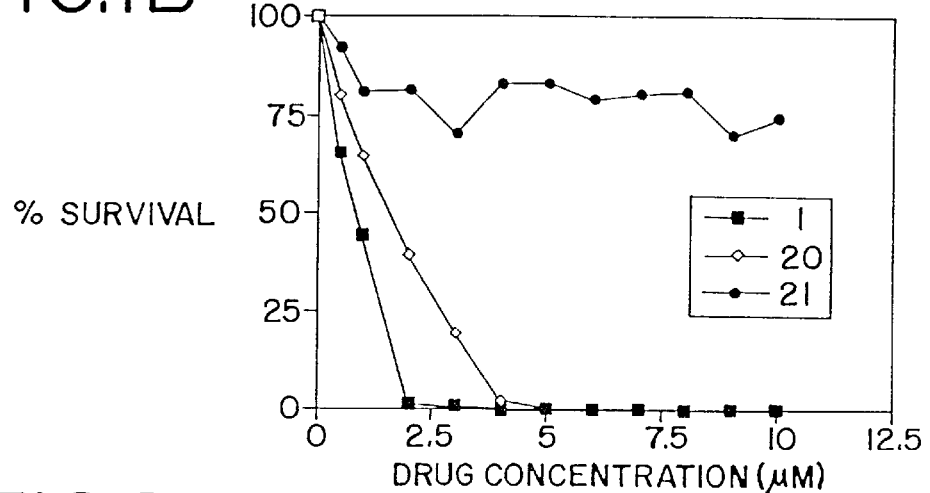

The cells were then washed by centrifuging them at 1200 rpm. Fresh culture medium was added, and the cells were incubated for an additional three days as described above. Viable promastigotes were counted as before, and the results are presented in FIG. 1B.

Compound 1 dissolved in corn oil was administered intraperitoneally to Balb/c mice (Ball State University colony) at 80 mg/kg/day for seven days beginning one day prior to injection of $5\times10^6$ *L. major* promastigotes in medium 199 in the hind foot. Control mice received an equivalent amount of corn oil and L. major. Beginning on day 8, the thickness of the footpads top to bottom was measured using a vernier caliper. Footpad swelling indicates progression of the disease. The percent increase in footpad size was calculated as:

$$\frac{\text{Infected Footpad Size} - \text{Normal Footpad Size}}{\text{Normal Footpad Size}} \times 100$$

Figure 2:
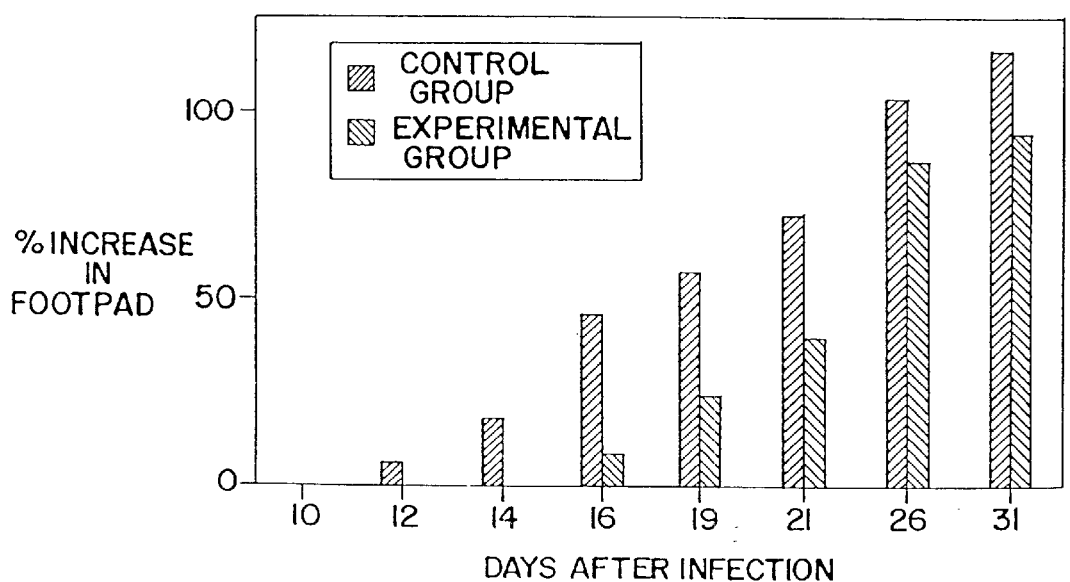
FIG. 2: Graph of percent increase in footpad size versus time.

The results are presented in FIG. 2. The percent increase in footpad size is for triplicate mice in the control group and duplicate mice in the treated group. Finally, the mice did not appear to be adversely affected by the administration of compound 1 as measured by weight loss.

Example 51

In Vitro Cytotoxicity

Lavendamycin analogs 2–16 and 58–61, quinolinediones 23–30 and lavendamycin methyl ester (55) were screened for antitumor activity as described in Example 47. The preparation and structures of lavendamycin analogs 2–16 are set forth in Examples 2–16. The preparation and structures of quinolinediones 23–30 are set forth in Examples 23–30. The preparation of lavendamycin methyl ester (55) is described in Example 47. Lavendamycin analogs 58–61 were prepared from the corresponding aldehydes and tryptophans as described above. For experimental conditions and yields, see Table XIII below. For analytical data, see Table XIV below. The results of the screening are presented in Tables XV and XVI below.

TABLE XIII

| Compd. | $R^{10}$ | Y | $R^4$ | $R^5$ | Solvent | Hours (° C.) | Yield (%) |
|---|---|---|---|---|---|---|---|
| 58 | $(CH_3)_2CH$ | $CO_2CH_3$ | H | H | Xylene | 3 (25–130°) 4 (130°) | 62.7 |
| 59 | $CH_3$ | $CH_2OH$ | H | H | Anisole | 3 (room-160 N) | 48 |
| 60 | $CH_3$ | $CO_2CH_2C_6H_5$ | H | H | Xylene | 3 (25–130°) 16.5 (130–135°) | 58 |
| 61 | $CH_3$ | $CO_2CH_2CH_3$ | H | H | Xylene | 6 (25–167 N) 32 (107°) | 54.8 |

TABLE XIV

| Compound | $R^{10}$ | Y | $R^4$ | $R^6$ | $^1$H, NMR | MS | HRMS |
|---|---|---|---|---|---|---|---|
| 58 | $(CH_3)_2CH$ | $CO_2CH_3$ | H | H | 1.4(d, 6H), 2.75(xt, 1H), 4.09(s, 3H), 7.41(dd, 1H), 7.81–7.67(m, 2H), 7.82(s, 1H), 8.0(s, 1S), 8.38(dd, 1H), 8.50(d, 1H), 8.97(s, 1H), 9.06(d, 1H), 11.37(s br, 1H) | 468(40), 452(100), 394(45) | $C_{26}H_{20}N_7O_5$ Calc 468.14471 Found 468.14229 |
| 59 | $CH_3$ | $CH_2OH$ | H | H | (DMSO) 2.30(s, 2H), 3.75–4.1(AB, 2H), 7.13(d, 1H), 7.31(t, 1H), 7.45(d, 1H), 7.68(d, 1H), 7.81(s, 1H), 8.49(d, 1H), 8.61(d, 1H), 10.3(s, 1H), 11.2(s, 1H) | 415(M+3$^+$, 60), 414(M+2$^+$, 55), 413(M+1$^+$, 70), 412(M$^+$, 100) | |
| 60 | $CH_3$ | $CO_2CH_2C_6H_5$ | H | H | 2.35(s, 3H), 5.5(s, 2H), 7.26(s, 5H), 7.43(t, 1H), 7.61(d, 1H), 7.70(t, 1H), 7.97(s, 1H), 8.22(s, 1H), 8.40(s br, 1H), 8.51(d, 1H), 8.96(s, 1H), 9.17(d, 1H) | | |
| 61 | $CH_3$ | $CO_2CH_2CH_3$ | H | H | 1.52(t, 3H), 2.31(s, 3H), 4.53(q, 2H), 7.34(d, 1H), 7.64–7.61(2H), 7.91(s, 1H), 8.18(d, 1H), 8.34(s, 1H), 8.46(d, H), 8.89(s, 1H), 9.10(d, 1H), 11.69(s br, 1H) | | $C_{25}H_{18}N_4O_5$ Calc 454.1277 Found 454.1255 |

TABLE XV

| Compound | LC50 (:M) | | | | |
|---|---|---|---|---|---|
| | NRKE | K/1 | H/1.2 | N/4.2 | 3LL |
| 2 | 0.15 | 0.07 | 0.11 | 0.10 | 0.40 |
| 3 | 0.70 | 0.40 | 0.69 | 0.70 | 1.0 |
| 4 | 2.5 | 2.2 | 2.1 | 2.2 | >3.3 |
| 5 | 0.62 | 0.33 | 0.70 | 0.84 | 2.1 |
| 6 | 0.40 | 0.44 | 0.40 | 0.49 | 3.0 |
| 7 | 0.58 | 0.79 | 0.58 | 0.76 | 2.0 |
| 8 | 0.96 | 0.52 | 0.74 | 1.05 | 2.3 |
| 9 | 1.35 | 0.56 | 1.32 | 1.2 | 3.2 |
| 10 | >33.0 | 15.0 | >33.0 | >33.0 | >33.0 |
| 11 | 0.32 | 0.33 | 0.40 | 0.42 | 0.82 |
| 12 | 0.66 | 0.50 | 0.41 | 0.70 | 2.3 |
| 13 | 1.0 | 0.6 | 0.37 | 0.65 | 2.4 |
| 14 | >33.0 | 3.3 | 16.0 | 15.0 | 16.0 |
| 15 | 0.90 | 0.40 | 0.61 | 0.50 | 0.9 |
| 16 | 0.90 | 0.35 | 0.23 | 0.22 | 0.21 |
| 23 | 5.0 | 12.5 | 5.5 | 7.0 | 3.7 |
| 24 | 3.6 | 5.8 | 3.4 | 3.2 | 2.1 |
| 25 | >3.3 | 2.15 | >3.3 | >3.3 | 1.0 |
| 26 | 3.0 | >3.3 | 3.3 | >3.3 | 2.5 |

TABLE XV-continued

| | LC50 (:M) | | | | |
|---|---|---|---|---|---|
| Compound | NRKE | K/1 | H/1.2 | N/4.2 | 3LL |
| 27 | 4.6 | 14.0 | 5.0 | 5.7 | 2.6 |
| 28 | 3.2 | 6.6 | 2.8 | 3.4 | 2.3 |
| 29 | 1.5 | 7.5 | 1.45 | 1.15 | 0.71 |
| 30 | 2.0 | >3.3 | 2.7 | >3.3 | 2.2 |
| 55 | 0.1 | 0.03 | 0.11 | 0.06 | 0.25 |
| 56 | >3.3 | 2.1 | >3.3 | 2.2 | 3.2 |
| 58 | 0.70 | 0.50 | 0.66 | 0.64 | 1.3 |
| 59 | 0.25 | 0.20 | 0.20 | 0.22 | 0.40 |
| 60 | 9.50 | 9.50 | >10.0 | >33.0 | >33.0 |
| 61 | 0.30 | 0.04 | 0.36 | 0.20 | 3.2 |

TABLE XVI

| | Differential Index | | | |
|---|---|---|---|---|
| Compound | K/1 | H/1.2 | N/4.2 | 3LL |
| 2 | 2.14 | 1.36 | 1.50 | 0.38 |
| 3 | 1.75 | 1.01 | 1.00 | 0.70 |
| 4 | 1.14 | 1.19 | 1.14 | <0.75 |
| 5 | 1.88 | 0.88 | 0.74 | 0.29 |
| 6 | 0.91 | 1.00 | 0.82 | 0.13 |
| 7 | 0.73 | 1.00 | 0.76 | 0.29 |
| 8 | 1.85 | 1.30 | 0.91 | 0.42 |
| 9 | 2.41 | 1.02 | 1.13 | 0.42 |
| 10 | >2.2 | i1.0 | i1.0 | i1.0 |
| 11 | 0.97 | 0.80 | 0.76 | 0.39 |
| 12 | 1.32 | 1.61 | 0.94 | 0.29 |
| 13 | 1.67 | 2.70 | 1.53 | 0.42 |
| 14 | >10.0 | >2.06 | >2.2 | >2.06 |
| 15 | 2.25 | 1.48 | 1.80 | 1.00 |
| 16 | 2.57 | 3.91 | 4.09 | 4.29 |
| 23 | 0.4 | 0.9 | 0.7 | 1.35 |
| 24 | 0.6 | 1.06 | 1.125 | 1.7 |
| 25 | >1.5 | ~1.0 | ~1.0 | >3.3 |
| 26 | <0.9 | 0.9 | <0.9 | 1.2 |
| 27 | 0.3 | 0.9 | 0.8 | 1.8 |
| 28 | 0.48 | 1.1 | 0.9 | 1.4 |
| 29 | 0.2 | 1.03 | 1.3 | 2.1 |
| 30 | <0.6 | 0.7 | <0.6 | 0.9 |
| 55 | 3.33 | 0.9 | 1.67 | 0.4 |
| 56 | >1.57 | i1.00 | >1.5 | >1.03 |
| 58 | 1.40 | 1.07 | 1.09 | 0.54 |
| 59 | 1.25 | 1.25 | 1.14 | 0.63 |
| 60 | 1.00 | <0.95 | <0.29 | <0.29 |
| 61 | 7.5 | 0.83 | 1.5 | 0.09 |

NRKE = Normal Rat Kidney Epithelial Cells.
K/1 = ras$^K$ Transformed NRKE Cells.
H/1.2 = ras$^H$ Transformed NRKE Cells.
N/4.2 = ras$^N$ transformed NRK cells
3LL = Lewis Lung Carcinoma Cells.

Example 52

Synthesis of 6-Chlorolavendamycin Methyl Ester (58)

7-N-Acetyllavendamycin methyl ester (AA) in 60 ml dried methanol was stirred and heated in a 60° C.–65° C. oil bath. While a stream of dry hydrogenchloride was being passed through the solution for 21 hrs. (See Equation 10 below) The reaction mixture was immediately rotaryevaporated to dryness to give 64.3 mg (88%) of an orange solid. Mp: 270° C. (dec). 1H NMR (CDCl$_3$) :11.88(s, 1H), 9.09 (d,1H), 8.60(d, 1H), 8.37(d, 1H), 7.79(d, 1H), 7.77(s, 1H), 7.65(t, 1H), 7.40(t, 1H), 4.07(s, 3H), 3.21(s, 3H).

Equation 10

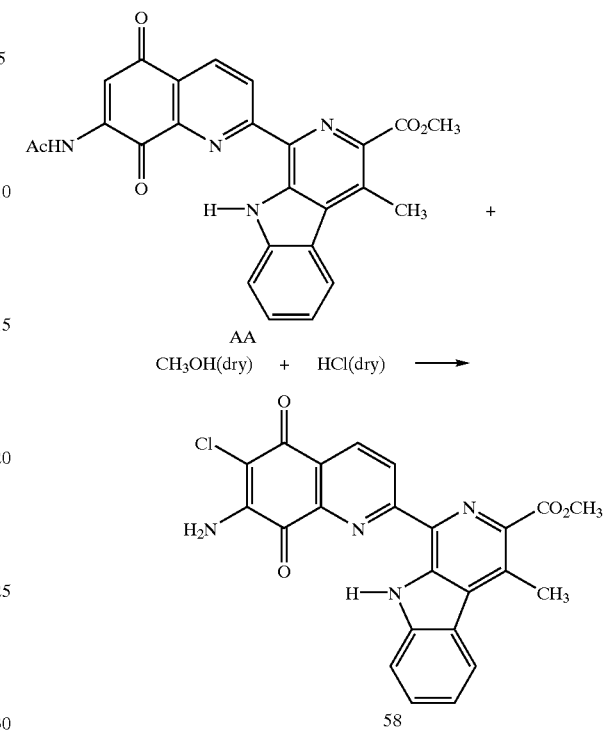

This compound 58 was tested in the NCI In Vitro Screening described in Example 49 above and also in the NCI Hollow Fiber Assay For Preliminary In Vivo Testing described in Example 55 below.

Example 53

Synthesis of 7-Amino-6-Chloro-2-Methylquinoline-5,8-Dione (59)

A slow stream of hydrogen chloride gas was passed through a solution of 7-acetamido-2-methylquinoline-5,8-dione (6, 230 mg, 1 mmol) in dry methanol (15 ml)at 60° C. for 48 h. (See Equation 11 below) The resulting acidic solution was neutralized with 2% sodium bicarbonate (10 ml), extracted with CH2Cl2 (5×30 ml) and dried over sodium sulfate (2.0 g, 20 min). Evaporation of the solvent in vacuo afforded 98 mg (42%) of pure (59) as red crystals: mp 270° C. (Dec.,MeOH); $^1$H NMR (CDCl3) δ8.31 (1H, d, J=8.0 Hz, H—4), 7.47 (1H, d, J=8.0 Hz, H—3), 5.70 (2H, br s, NH$_2$), 2.68 (3H, s, CH$_3$); IR (KBr) V$_{max}$ 3471, 3329, 3191, 3085, 2960, 2924, 1649, 1605, 1587, 1573, 1382, 1370, 1326, 1273, 1259, 1164, 737 cm–$^1$; EIMS, m/e (relative intensity) 223 (M+1, 100), 189 (4.1), 133 (0.4), 81 (0.8), 69 (1.2); EIMS, m/e (relative intensity) 224 (M+2, 27.3), 222 (M+, 97.2), 195 (7.4), 187 (M–Cl, 100), 166 (5.3), 131 (10.4), 104 (12.1), 77 (14.9), 64 (10.5); HRMS, m/e for C$_{10}$H$_7$ClN$_2$O$_2$ calcd 222.0196, found 222.0194.

Equation 11

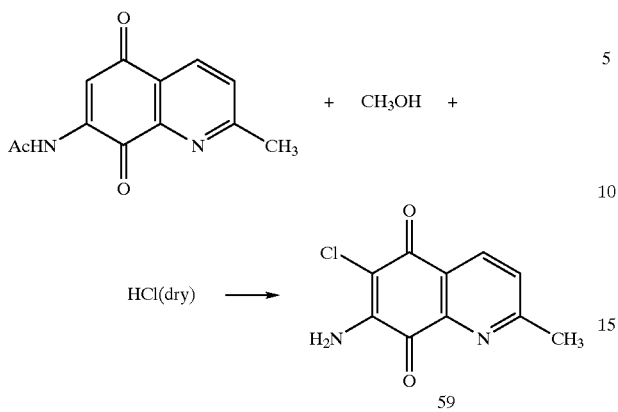

Example 54

Synthesis of 6-Chloro-7-Amino-2-Formylquinoline-5,8-Dione (60)

A stirred mixture of 6-Chloro-7-amino-2-methylquinoline (2) (267.6 mg, 1.2 mmol) and $SeO_2$ (213 mg, 1.92 mmol) in dry dioxane (40 ml) and water (0.18 ml) under Ar was heated at reflux for 23 hrs. (See Equation 12 below) The mixture was not filtered and the residue on the filter paper was washed with 40 ml chloroform. Evaporation of the filtrate gave a red residue. This residue was dissolved in 480 ml of chloroform, washed with 4×60 ml sodium chloride saturated solution and dried with anhydrous $MgSO_4$. After evaporation it gave a red solid (3) 209 mg (74%). Mp:. 211° C (dec), $^1H$ NMR ($CDCl_3$): 10.24(s, 1 H), 8.63(d, 1H), 8.25(d, 1H), 5.6–6.0(broad, NH).

Equation 12

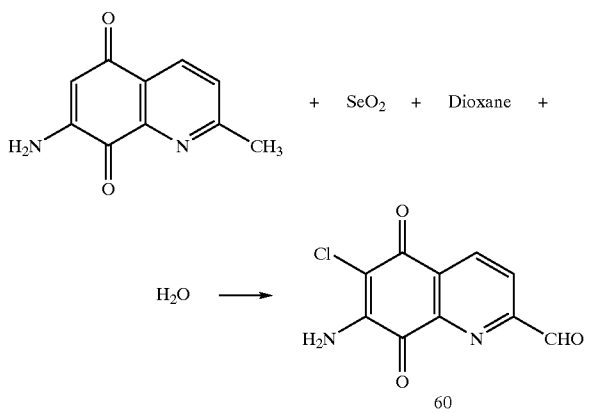

Example 55

Synthesis of Demethyllavendamycin Octyl Ester

The following compound (61) was synthesized by acid hydrolysis of compound 21 and then characterized by spectroscopic methods.

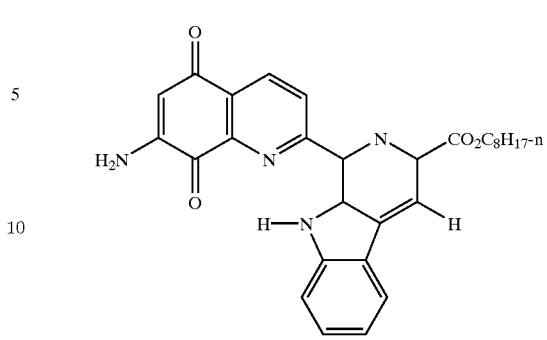

Example 56

NCI Hollow Fiber Assay for Preliminary in Vivo Testing

The biological Testing Branch of the Developmental Therapeutics Program of the National Cancer Institute has adopted a preliminary in vivo screening tool for assessing the potential anticancer activity of compounds identified by the large scale in vitro cell screen. For these assays, human tumor cells are cultivated in polyvinylidene fluoride (PVDF) hollow fibers, and a sample of each cell line is implanted into each of two physiologic compartments (intraperitoneal and subcutaneous) in mice. Each test mouse receives a total of 6 fibers (3 intraperitoneally and 3 subcutaneously) representing 3 distinct cancer cells lines. Three mice are treated with potential antitumor compounds at each of 2 test doses by the intraperitoneal route using a QD×4 treatment schedule. Vehicle controls consist of 6 mice receiving the compound diluent only. The fiber cultures are collected on the day following the last day of treatment. To assess anticancer effects, viable cell mass is determined for each of the cell lines using a formazan dye (MTT) conversion assay. From this, the % T/C can be calculated using the average optical density of the compound treated samples divided by the average optical density of the vehicle controls. In addition, the net increase in cell mass can be determined for each sample as a sample of fiber cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as % T/C for each of the 2 compound doses against each of the cell lines with separate values calculated for the intraperitoneal and subcutaneous samples.

Compounds are selected for further in vivo testing in standard subcutaneous xenograft models on the basis of several hollow fiber assay criteria. These include: (1) a % T/C of 50 or less in 10 of the 48 possible test combinations (12 cell lines×2sites×2compound doses); (2) activity at a distance (intraperitoneal drug/subcutaneous culture) in a minimum of 4 of the 24 possible combinations; and/or (3) a net cell kill of 1 or more cell lines in either implant site. To simplify evaluation, a points system has been adopted which allows rapid viewing of the activity of a given compound.

For this, a value of 2 is assigned for each compound dose which results in a 50% or greater reduction in viable cell mass. The intraperitoneal and subcutaneous samples are scored separately so that criteria (1) and (2) can be evaluated. Compounds which meet the guidelines of the Biological evaluation Committee for Cancer Drugs (BEC/C) for Further Testing, namely a combined IP+SC score $\geq$20, a SC score $\geq$8 or a net cell kill of one or more cell lines, are referred for evaluations in subcutaneous human tumor xenograft assays. These criteria were statistically validated by comparing the activity outcomes of >80 randomly selected compounds in the hollow fiber assay and in the xenograft testing. This comparison indicated that there was a very low probability of missing an active compound if the hollow fiber assay were used as the initial in vivo screening tool. In addition to these criteria, other factors (e.g. unique structure, mechanism of action) may result in referral of a compound for standard xenograft testing without the compound meeting these criteria.

Compound 58 (6-chlorolavendamycin methyl ester) was submitted to this test and received the following scores:

IP Score: 10
SC Score: 4
Total Score: 14
Cell Kill: N

Example 57

Anti-HIV Reverse Transcriptase Activity

Compound Nos. 1, 2, 12, 16, 17, 20, 21 and 61 were tested for anti-HIV reverse transcriptase activity. In addition, lavendamycin methyl ester (Compound B above) and streptonigrin (Compound G above) were likewise tested. The inhibition of HIV-RT activity was measured by a modification of the methods of Hoffman et al (1985), Take et al (1989) and Robbins et al (1994). Hoffman, A.: Bananpour, B.; Levy, J. Characterization of the AIDS-associated retrovirus reverse transcriptase and optimal conditions for its detection in virions. *Virology*, 1985, 147, 326. Take, Y.; Inouke, Y.; Nakamura, S.; Comparative studies of the inhibitory properties of Antibiotics on human immunodeficiency virus and cellular DNA polymerases. *Journal of Antibiotics* 1989, 42, 107. Robbins, B.; Rodman, J.; McDonald, C,; Srinivas, R.; Flynn, P.; Fridland, A.; Enzymatic Assay for the measurement of Zidovudine Triphosphate in peripheral blood mononuclear cells. *Antimicrobial Agents and Actions* 1994, 38, 115.

The procedure was as follows: The reaction mixture (100 $\mu$l) consisted of 100 mM Tris-HCL(pH 8.0), 5 mM dithiothreiotol, 5 mM MgCl$_2$, 60 mM NaCl, 4$\mu$g/ml poly (rA)-oligo(dt)$_{12-18}$, 0.2 mM[$^3$H]TTP and 1.0 units/ml of HIV-RT (Worthington Biochemical).

The samples to be tested were initially dissolved in DMSO at no more than 1 mg/ml and then serially diluted with distilled water to provide different concentrations of test solutions. A mixture of assay solution containing all the above reactants, buffers and salts in 8×concentration was added to each test solution to give the final reaction mixture in a total of 300 $\mu$l. For each test solution this reaction mixture was divided into three aliquots of 100 $\mu$l each and incubated on a 96 well flat-bottom microtiter plate at 37° C. for 1 hour. The reaction was terminated with 25 $\mu$l of 0.1 M EDTA on ice and 30 $\mu$l from each test well was spotted on 1 cm square of DE 81 ion exchange paper (Whatman). Each filter paper square was then washed 3 times with 5% TCA-NaHPO$_4$. 12H$_2$O and then one time each with dd H$_2$O and 95% ethanol. The squares were washed sequentially in beakers for 18–20 minutes with swirling. Streptonigrin (3 $\mu$g/ml) or AZT-TriPO$_4$ (1 $\mu$g/ml) was used as positive inhibitory controls. As a negative control, no enzyme was added to the reaction mixture. The squares were then dried and added to vials with scintillation fluid and the amount of radioactive uptake measured on a Beckman liquid scintillation counter.

The inhibitory capacity of each analog at each of the three enzyme concentrations mentioned above was determined at 4 different drug concentrations ranging from 15 to 0.125 $\mu$g/ml by comparing the mean enzymatic incorporation of [$^3$H]TTP in the presence of each drug to the mean incorporation in the absence of the drug. The concentration at which 50 percent of the enzymatic activity is inhibited (IC$_{50}$) was determined by simple linear interpolation from this data for each enzyme concentration. These IC$_{50}$ determinations were repeated three times at least and evaluated for validity against our positive standards. The results are shown in Table XVII below:

TABLE XVII

| Compound | IC$_{50}$ for HIV-RT (mM) |
| --- | --- |
| 21 | 10.62 |
| 12 | 12.28 |
| 20 | 18.54 |
| 2 | 22.39 |
| 1 | 26.84 |
| 16 | 27 |
| 17 | >30 |
| 61 | 18.19 |
| B | >30 |
| Streptonigrin | 21.35 |

In order to determine any possible additive or synergistic inhibitory activity which the lavendamycin analogs might have when combined with AZT, a range of concentrations of both 3'-azido-3'-deoxythymidine 5'-triphosphate (AZT-TP) and a lavendamycin analog at levels equal or below the IC$_{50}$ concentration for either drug alone were tested as described above. AZT-TP was used for these in vitro studies since AZT is naturally phosphorylated in vivo.

The results of these tests are given in Table XVIII and XIX below, where the percent inhibition of HIV-RT activity is reported for three different trials and then averaged in the seventh column. For those experiments which used a combination of AZT-TP and a lavendamycin analog, the eighth column shows the average percent inhibition measured for the combination minus the average percent inhibition for the same concentration of each of the compounds singly. Thus, a positive number in this column shows a synergistic effect, namely the combination produced a higher percent inhibition than the sum of the compounds alone.

Likewise, a negative number shows an antagonistic effect.

TABLE XVIII

| Drug | LA Conc. (mM) | AZT-TP Conc. (mM) | % inh. Trial 1 | % inh. Trial 2 | % inh. Trial 3 | % inh. ave. | Compared to Add. |
|---|---|---|---|---|---|---|---|
| AZT-TP | 0 | 0.05 | 51 | 52 | 49 | 50.7 | |
| AZT-TP | 0 | 0.01 | 27 | 27 | 29 | 27.7 | |
| 16 | 6.0 | 0 | 26 | 33 | 30 | 29.7 | |
| 16 | 3.0 | 0 | 0 | 3 | 12 | 5.0 | |
| 16 | .5 | 0 | 0 | 0 | 0 | 0.0 | |
| AZT-TP + 16 | 6.0 | 0.05 | 70 | 67 | 69 | 68.7 | −11.7 |
| AZT-TP + 16 | 3.0 | 0.05 | 70 | 67 | 69 | 68.7 | 13.0 |
| AZT-TP + 16 | 0.5 | 0.05 | 53 | 62 | 58 | 57.7 | 7.0 |
| AZT-TP + 16 | 6.0 | 0.01 | 55 | 51 | 50 | 52.0 | −5.3 |
| AZT-TP + 16 | 3.0 | 0.01 | 47 | 47 | 30 | 41.3 | 8.7 |
| AZT-TP + 16 | .5 | 0.01 | 48 | 40 | 42 | 43.3 | 15.7 |

TABLE XIX

| Drug | LA Conc. (mM) | AZT-TP Conc. (mM) | % inh. Trial 1 | % inh. Trial 2 | % inh. Trial 3 | % inh. ave. | Compared to Add. |
|---|---|---|---|---|---|---|---|
| AZT-TP | 0 | .05 | 56 | 48 | 50 | 51.3 | |
| AZT-TP | 0 | 0.01 | 18 | 17 | 14 | 16.3 | |
| 20 | 0.5 | 0 | 0 | 5 | 6 | 20 | 10.3 |
| 21 | 0.5 | 0 | 13 | 6 | 28 | 15.7 | |
| 2 | 0.5 | 0 | 12 | 5 | 17 | 11.3 | |
| AZT-TP + 20 | 0.5 | 0.05 | 63 | 59 | 66 | 62.7 | 1.0 |
| AZT-TP + 21 | 0.5 | 0.05 | 64 | 69 | 63 | 65.3 | −1.7 |
| AZT-TP + 2 | 0.5 | 0.05 | 69 | 69 | 70 | 69.3 | 6.7 |
| AZT-TP + 20 | 0.5 | 0.01 | 41 | 42 | 50 | 44.3 | 17.7 |
| AZT-TP + 21 | 0.5 | 0.01 | 50 | 55 | 44 | 49.7 | 17.7 |
| AZT-TP + 2 | 0.5 | 0.01 | 59 | 47 | 46 | 50.7 | 23.0 |

As seen above, some combinations of the lavendamycin analogs with AZT-TP resulted in RT inhibition which reflected simply an additive effect of the two drugs acting independently to inhibit the enzymatic activity. These combinations resulted in a total combined activity which was approximately +/−5% of the expected additive effect.

A few of the combinations resulted in synergistic activity where the combined activity significantly exceeded the additive effect of either drug alone, namely >5% of the expected additive effect.

In general, the best combined activity with lavendamycin analogs was observed at concentrations of AZT-TP lower than the $IC_{50}$ dose. At higher levels of AZT-TP, the drug combinations appeared to interact antagonistically giving less than an additive effect.

We claim:

1. A compound having the following formula:

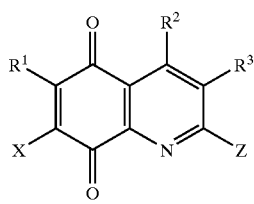

wherein,

X is 

$R^1$ is H, a halogen atom, $NO_2$, CN, $OR^{13}$, $SR^{13}$, $N(R^{13})_2$,

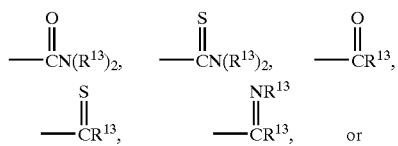

an alkyl, aryl, cycloalkyl, alkenyl, alkynyl, or heteroalkyl, heterocyclic, heteroalkenyl or heteroalkynyl residue, each of which may be substituted or unsubstituted, with the proviso that when x is $NH_2$, $R_1$ is not $OR^{13}$, alkyl or heteroalkyl, $R^2$ is H, $R^3$ is H or $CH_3$, $R^{10}$ and $R^{13}$, which may be the same or different, each is independently H or an alkyl, cycloalkyl, alkenyl, alkynyl, aryl or heterocyclic residue, each of which may be substituted or unsubstituted, and Z is $CH_3$, and pharmaceutically acceptable salts thereof.

2. The compound of claim 1 wherein $R^1$ is Cl.

3. A compound having the following formula:

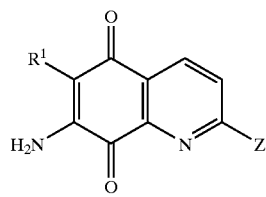

wherein $R^1$ is a halogen atom, and

Z is $CH_3$.

4. The compound of claim 3 wherein $R^1$ is Cl.

5. A method of treating an animal suffering from cancer comprising administering to the animal suffering from cancer an effective amount of the compound of claim 1, 2, 3 or 4.

6. The method of claim 5 wherein the cancer is selected from the group consisting of ovarian, colon, breast, cervical, esophageal, glioblastoma, neuroblastoma, stomach, kidney, skin, lung, pancreatic, seminoma, melanoma, bladder, thyroid, myeloid and lymphoid.

* * * * *